(12) United States Patent
Squillace

(10) Patent No.: US 7,658,706 B2
(45) Date of Patent: Feb. 9, 2010

(54) VASCULAR GRAFT STERILIZATION AND DECELLULARIZATION

(75) Inventor: Donna Squillace, Gainesville, FL (US)

(73) Assignee: RTI Biologics, Inc., Alachua, FL (US)

( * ) Notice: Subject to any disclaimer, the term of this patent is extended or adjusted under 35 U.S.C. 154(b) by 235 days.

(21) Appl. No.: 11/634,436

(22) Filed: Dec. 5, 2006

(65) Prior Publication Data

US 2007/0260109 A1    Nov. 8, 2007

Related U.S. Application Data

(60) Provisional application No. 60/742,828, filed on Dec. 5, 2005.

(51) Int. Cl.
*A61F 2/04* (2006.01)
(52) U.S. Cl. ....................... 600/36
(58) Field of Classification Search ............ 600/36; 623/1.38, 1.39, 1.4; 128/897, 898; 435/289.1
See application file for complete search history.

(56) References Cited

U.S. PATENT DOCUMENTS

| | | | |
|---|---|---|---|
| 4,144,744 A * | 3/1979 | Hill | 73/49.1 |
| 5,415,619 A * | 5/1995 | Lee et al. | 600/36 |
| 5,460,962 A | 10/1995 | Kemp | |
| 5,792,603 A | 8/1998 | Dunkelman et al. | |
| 5,890,489 A * | 4/1999 | Elden | 128/898 |
| 5,899,936 A | 5/1999 | Goldstein | |
| 5,993,844 A | 11/1999 | Abraham et al. | |
| 5,997,575 A * | 12/1999 | Whitson et al. | 623/1.1 |
| 6,121,042 A | 9/2000 | Peterson et al. | |
| 6,312,474 B1 | 11/2001 | Francis et al. | |
| 6,334,872 B1 | 1/2002 | Termin et al. | |
| 6,432,712 B1 | 8/2002 | Wolfinbarger, Jr. | |
| 6,482,584 B1 | 11/2002 | Mills et al. | |
| 6,509,145 B1 | 1/2003 | Torrianni | |
| 6,533,767 B2 * | 3/2003 | Johansson et al. | 604/507 |
| 6,561,970 B1 | 5/2003 | Carpentier et al. | |
| 6,572,650 B1 | 6/2003 | Abraham et al. | |
| 6,689,161 B2 | 2/2004 | Chen et al. | |
| 6,734,018 B2 | 5/2004 | Wolfinbarger, Jr. et al. | |
| 6,866,686 B2 | 3/2005 | Ollerenshaw et al. | |
| 6,878,168 B2 | 4/2005 | Carpentier et al. | |
| 6,893,653 B2 | 5/2005 | Abraham et al. | |
| 7,008,763 B2 * | 3/2006 | Cheung | 435/1.1 |
| 2003/0027125 A1 * | 2/2003 | Mills et al. | 435/1.1 |
| 2003/0180268 A1 | 9/2003 | Atala | |
| 2003/0219417 A1 | 11/2003 | Wolfinbarger | |
| 2004/0076657 A1 | 4/2004 | Wolfinbarger et al. | |
| 2005/0203636 A1 | 9/2005 | McFetridge | |

OTHER PUBLICATIONS

Demasi, R.J. and S.O. Snyder, The current status of prosthetic-vein composite grafts for lower extremity revascularization. Surg Clin North Am, 1995. 75(4): p. 741-52.

Benedetti-Valentini, F., Gossetti, B., Irace, I., Martinelli, O., Gattuso, R., Composite grafts for critical ischemia. Cardio Vasc Surg, 1996. 4(3): p. 372-376.

Delaurentis, D., Freidmann, P., Arterial reconstruction about and below the knee: another look. Am J Surg, 1971. 121(April): p. 392-397.

Linton, R.R., Wirthlin, L.S., Femoropopliteal composite Dacron and autogenous vein bypass grafts. Arch Surg, 1973. 107: p. 748-753.

Promotion, N.C.f.C.D.P.a.H., Diabetes: Disabling, Deadly, and on the Rise. 2002, Centers for Disease Control and Prevention.

Hepatitis C virus transmission from an antibody negative organ and tissue donor—United States, 2000-2002. MMWR Weekly, 2003. 52(13): p. 273-276.

Silverstein, R.L., The Vascular Endothelium, in Inflammation: Basic Principles and Clinical Correlates, J.I. Gallin and R. Snyderman, Editor. 1999, Lippincott Williams & Wilkins: Philadelphia. p. 207-225.

Allaire, E., et al., Cell-free arterial grafts: morphologic characteristics of aortic isografts, allografts, and xenografts in rats. J Vasc Surg, 1994. 19(3): p. 446-56.

Madden, R., et al., Decellularized cadaver vein allografts used for hemodialysis access do not cause allosensitization or preclude kidney transplantation. Am J Kidney Dis, 2002. 40(6): p. 1240-3.

Kasimir, M.T., et al., Comparison of different decellularization procedures of porcine heart valves. Int J Artif Organs, 2003. 26(5): p. 421-7.

Block, S.S., Disinfection, Sterilization, and Preservation. Fifth ed. 2001, Philadelphia: Lippincott Williams & Wilkins.

Guidance on the Content and Format of Premarket Notification [510(k)] Submissions for Liquid Chemical Germicides, U.S.D.o.H.a.H. Services, Editor. 1996.

Kenyon, D.E., A mathematical model of water flux through aortic tissue. Bull Math Biol, 1979. 41(1): p. 79-90.

Wang, D.M. and J.M. Tarbell, Modeling interstitial flow in an artery wall allows estimation of wall shear stress on smooth muscle cells. J Biomech Eng, 1995. 117(3): p. 358-63.

Conte, M.S., The ideal small arterial substitute: a search for the Holy Grail? Faseb J, 1998. 12(1): p. 43-5.

Conklin, B.S., et al., Development and evaluation of a novel decellularized vascular xenograft. Med Eng Phys, 2002. 24(3): p. 173-83.

Stillman, R.M., Excerpt from infrainguinal occlusive disease, eMedicine.

(Continued)

*Primary Examiner*—Samuel G Gilbert
(74) *Attorney, Agent, or Firm*—McAndrews, Held & Malloy, Ltd.

(57) ABSTRACT

The present technology is related to the field of sterilization and decellularization of allografts or xenografts, specifically to processes that achieve effective removal of the cells contained within a vascular tissue matrix and an effective reduction in potential harmful organisms to create grafts suitable for human implantation. In some embodiments, vascular grafts, vascular tissue and/or blood vessels are contacted with cleaning solution under conditions suitable conditions to reduce immune reaction in patients. More specifically, the present technology is directed to sterilization and decellularization of vascular grafts.

10 Claims, 41 Drawing Sheets

OTHER PUBLICATIONS

Prager, M., Holzenbein, T., Aslim, E., Domenig, C., Muhlbacher, F., Kretschmer, G., Fresh arterial homograft transplantation: a novel concept for critical limb ischemia. Eur J Vasc Endovasc Surg, 2002. 24: p. 314-321.

Timaran, C., Goldman, MH, Saphenous vein allografts for infrainguinal arterial reconstruction: current role as vascular conduits. Adv Vasc Surg, 2002. 10: p. 183-197.

Bader, A., et al., Engineering of human vascular aortic tissue based on a xenogeneic starter matrix. Transplantation, 2000. 70(1): p. 7-14.

Administration, U.S.F.a.D., Human Cells, Tissues, and Cellular and Tissue-Based Products. 2004.

Bastounis, E., et al., PTFE-vein composite grafts for critical limb ischaemia: a valuable alternative to all-autogenous infrageniculate reconstructions. Eur J Vasc Endovasc Surg, 1999. 18(2): p. 127-32.

Lord, J.W., Jr., et al., New technique for construction of coposite Dacron vein grafts for femoro-distal popliteal bypass in the severely ischemic leg. Ann Surg, 1975. 181(5): p. 670-5.

Oppat, W.F., et al., Natural history of composite sequential bypass: ten years' experience. Arch Surg, 1999. 134(7): p. 754-7; discussion 757-8.

Promotion, N.C.f.C.D.P.a.H., 1999 Diabetes Surveillance Report. 1999, Centers for Disease Control and Prevention.

Alexander, J.J., Wells, K.E., Yuhas, J.P., Piotrowski, J.J., The role of composite sequential bypass in the treatment of multilevel infrainguinal arterial occlusive disease. Am J Surg, 1996. 172: p. 118-122.

Castier, Y., et al., Early experience with cryopreserved arterial allografts in below-knee revascularization for limb salvage. Am J Surg, 1999. 177(3): p. 197-202.

Faries, P.L., Logerfo, F.W., Arora, S., Pulling, M.C., Rohan, D. I., Akbari, C.M., Campbell, D.R., Gibbons, G.W., Pomposelli, F.B., Arm vein conduit is superior to composite prosthetic-autogenous grafts in lower extremity revasculariztion. J Vasc Surg, 2000. 31(6): p. 1119-1126.

Londrey, G.L., Ramsey, D.E., Hodgson, K.J., Barkmeier, L.D., Sumner, D.S., Infrapopliteal bypass for severe ischemia: comparison of autogenous vein, composite, and prosthetic grafts. J Vasc Surg, May 1991. 13(5): p. 631-636.

Fung, Y.C. and S.Q. Liu, Determination of the mechanical properties of the different layers of blood vessels in vivo. Proc Natl Acad Sci U S A, 1995. 92(6): p. 2169-73.

McClurken, M., Lipson, D., Collagen shrinkage and vessel sealing. 2001, TissueLink Medical, Inc.: Dover.

Gupta, B.S., Kasyanov, V.A., Biomechanics of human common carotid artery and design of novel hybrid textile compliant vascular grafts. J Biomed Mater Res., 1997. 34(3): p. 341-349.

Gabriel, M., Kostrzewa, A., Sobieska, M., Immune response after cryopreserved aortic allograft replacement for major vascular infection. Transplant Proceedings, 2002. 34: p. 713-714.

Bowman, F.O., et al., Further evaluation of aortic valve homografts sterilized by electron-beam energy. Circulation, 1969. 39(supp I): p. 57-60.

Control, C.f.D., Update: allograft-associated bacterial infections—United States. MMWR Weekly Report, 2002. 51: p. 207-210.

Invasive Streptococcus pyogenes after allograft implantation—Colorado, 2003. MMWR Weekly, 2003. 52(48): p. 1173-1176.

Reller, L.B., et al., Bacterial endocarditis caused by Oerskovia turbata. 1975. 83(5): p. 664-666.

Pukacki, F., et al., The mechanical properties of fresh and cryopreserved arterial homografts. Eur J Vasc Endovasc Surg, 2000. 20(1): p. 21-4.

Bellon, J.M., et al., Arterial damage induced by cryopreservation is irreversible following organ culture. Eur J Vasc Endovasc Surg, 1999. 17(2): p. 136-43.

Galambos, B., et al., Preservation of vein allograft viability during long-term storage. Eur Surg Res, 2005. 37(1): p. 60-7.

Pascual, G., et al., Effect of the thawing process on cryopreserved arteries. Ann Vasc Surg, 2001. 15(6): p. 619-27.

Lin, P.H., Brinkman, W.T., Terramani, T.T., Lumsden, A.B., Management of infected hemodialysis access grafts using cryopreserved human vein allografts. Am J Surg, 2002. 184: p. 31-36.

Mirelli, M., Stella, A., Faggioli, G.L., Scolari, M.P., Iannelli, S., Freyrie, A., Buscaroli, A., De Santis, L., Resta, F., Bonomini, V., D'Addato, M., Immune response following fresh arterial homograft replacement for aortoiliac graft infection. Eur J Vasc Endovasc Surg, 1999. 18: p. 424-429.

Davies, M.G., et al., Functional and histological differences in autogenous and allogenic vein grafts: two different vasculopathies? J Surg Res, 1997. 69(1): p. 14-22.

Ketchedjian, A., et al., Recellularization of decellularized allograft scaffolds in ovine great vessel reconstructions. Ann Thorac Surg, 2005. 79(3): p. 888-96; discussion 896.

End-Stage Kidney Disease, MedlinePlus. p. Medical dictionary.

Hawkins, J.A., et al., Immunogenicity of decellularized cryopreserved allografts in pediatric cardiac surgery: comparison with standard cryopreserved allografts. J Thorac Cardiovasc Surg, 2003. 126(1): p. 247-52; discussion 252-3.

Grauss, R.W., et al., Decellularization of rat aortic valve allografts reduces leaflet destruction and extracellular matrix remodeling. J Thorac Cardiovasc Surg, 2003. 126(6): p. 2003-10.

Hilbert, S.L., et al., Explant pathology study of decellularized carotid artery vascular grafts. J Biomed Mater Res A, 2004. 69(2): p. 197-204.

Teebken, O.E., et al., Tissue engineering of vascular grafts: human cell seeding of decellularised porcine matrix. Eur J Vasc Endovasc Surg, 2000. 19(4): p. 381-6.

Schaner, P.J., et al., Decellularized vein as a potential scaffold for vascular tissue engineering. J Vasc Surg, 2004. 40(1): p. 146-53.

Huynh, T., et al., Remodeling of an acellular collagen graft into a physiologically responsive neovessel. Nat Biotechnol, 1999. 17(11): p. 1083-6.

Lu, Q., et al., Novel porous aortic elastin and collagen scaffolds for tissue engineering. Biomaterials, 2004. 25(22): p. 5227-37.

Courtman, D.W., B.F. Errett, and G.J. Wilson, The role of crosslinking in modification of the immune response elicited against xenogenic vascular acellular matrices. J Biomed Mater Res, 2001. 55(4): p. 576-86.

Sievers, H.H., et al., Decellularized pulmonary homograft (SynerGraft) for reconstruction of the right ventricular outflow tract: first clinical experience. Z Kardiol, 2003. 92(1): p. 53-9.

Samouillan, V., et al., Thermal analysis characterization of aortic tissues for cardiac valve bioprostheses. J Biomed Mater Res, 1999. 46(4): p. 531-8.

Rieder, E., et al., Decellularization protocols of porcine heart valves differ importantly in efficiency of cell removal and susceptibility of the matrix to recellularization with human vascular cells. J Thorac Cardiovasc Surg, 2004. 127(2): p. 399-405.

Cho, S.W., et al., Vascular patches tissue-engineered with autologous bone marrow-derived cells and decellularized tissue matrices. Biomaterials, 2005. 26(14): p. 1915-24.

Horowitz, B. and E. Ben-Hur, Strategies for viral inactivation. Curr Opin Hematol, 1995. 2(6): p. 484-92.

Huang, Q., et al., Use of peracetic acid to sterilize human donor skin for production of acellular dermal matrices for clinical use. Wound Repair Regen, 2004. 12(3): p. 276-87.

Pruss, A., et al., Validation of the sterilization procedure of allogeneic avital bone transplants using peracetic acid-ethanol. Biologicals, 2001. 29(2): p. 59-66.

Pruss, A., et al., Effect of gamma irradiation on human cortical bone transplants contaminated with enveloped and non-enveloped viruses. Biologicals, 2002. 30(2): p. 125-33.

Horowitz, B., et al., Solvent/detergent-treated plasma: a virus-inactivated substitute for fresh frozen plasma. Blood, 1992. 79(3): p. 826-31.

Van Bueren, J., D.P. Larkin, and R.A. Simpson, Inactivation of human immunodeficiency virus type 1 by alcohols. J Hosp Infect, 1994. 28(2): p. 137-48.

Acosta-Gio, A.E., J.L. Rueda-Patino, and L. Sanchez-Perez, Sporicidal activity in liquid chemical products to sterilize or high-level disinfect medical and dental instruments. Am J Infect Control, 2005. 33(5): p. 307-9.

Hodde, J. and M. Hiles, Virus safety of a porcine-derived medical device: evaluation of a viral inactivation method. Biotechnol Bioeng, 2002. 79(2): p. 211-6.

Koivunen, J. and H. Heinonen-Tanski, Inactivation of enteric microorganisms with chemical disinfectants, UV irradiation and combined chemical/UV treatments. Water Res, 2005. 39(8): p. 1519-26.

Hodde, J.P., et al., Retention of endothelial cell adherence to porcine-derived extracellular matrix after disinfection and sterilization. Tissue Eng, 2002. 8(2): p. 225-34.

Reinhart, D., Control of odors from construction and demolition (C&D) debris landfills. 2004, University of Florida: Gainesville.

Scheffler, S.U., et al., Biomechanical comparison of human bone-patellar tendon-bone grafts after sterilization with peracetic acid ethanol. Cell Tissue Bank, 2005. 6(2): p. 109-15.

Mazzola, P.G., T.C. Penna, and A.M. Martins, Determination of decimal reduction time (D value) of chemical agents used in hospitals for disinfection purposes. BMC Infect Dis, 2003. 3(1): p. 24.

Prosi, M., et al., Mathematical and numerical models for transfer of low-density lipoproteins through the arterial walls: a new methodology for the model set up with applications to the study of disturbed lumenal flow. J Biomech, 2005. 38(4): p. 903-17.

Tada, S. and J.M. Tarbell, Fenestral pore size in the internal elastic lamina affects transmural flow distribution in the artery wall. Ann Biomed Eng, 2001. 29(6): p. 455-66.

Ander, S., et al., Pressure-induced vector transport in human saphenous vein. Ann Biomed Eng, 2005. 33(2): p. 202-8.

Henzler, T. and E. Steudle, Transport and metabolic degradation of hydrogen peroxide in Chara corallina: model calculations and measurements with the pressure probe suggest transport of $H(2)O(2)$ across water channels. J Exp Bot, 2000. 51(353): p. 2053-66.

International Search Report dated Oct. 11, 2007 for PCT/US06/46514.

* cited by examiner

A.

B.

| Treatment | % Tissue Stained | CI (95%) | N | p-value |
|---|---|---|---|---|
| Untreated | 21.6 | 3.37 | 5 | |
| 0 mm Hg | 20.6 | 10.6 | 3 | 0.881 |
| 70 mm Hg | 4.16 | 3.71 | 6 | 0.000* |
| 160 mm Hg | 9.43 | 6.19 | 6 | 0.011* |

VASCULAR GRAFT STERILIZATION AND DECELLULARIZATION

CROSS-REFERENCE TO RELATED APPLICATION

This application claims priority to U.S. Provisional Application No. 60/742,828, filed on Dec. 5, 2005, entitled "Vascular Graft Sterilization and Decellularization", which is incorporated by reference herein in its entirety.

FIELD OF THE INVENTION

The present technology is related to the field of sterilization and decellularization of allografts or xenografts, specifically to processes that achieve effective removal of the cells contained within a vascular tissue and an effective reduction in potentially harmful organisms to create grafts suitable for human implantation. More specifically, the present technology is directed to methods to treat vascular allografts or xenografts to reduce immune reaction. Even more specifically, the present technology is directed to sterilization and decellularization of vascular grafts.

BACKGROUND OF THE INVENTION

Vascular disease is one of the most common diseases worldwide and, with the increasing age and longevity of the American population, will remain a major public health priority (Conte, 1998). The mainstay of therapy for patients with coronary and peripheral occlusions is surgical bypass grafting with the patient's own (autograft) saphenous vein or internal mammary artery. This procedure offers benefits to the patient but incurs significant economic cost on the national level. Commonly, insufficient autograft material is available and a patient may receive cadaver tissue (allograft). However, allograft conduits have poor patency rates resulting in numerous revision surgeries, amplifying the economic impact. A reduction in graft patency is a result of an immunological response to cellular material contained within and on the allograft leading to intimal hyperplasia and eventual graft occlusion.

Allografts can have complications leading to early stenosis and graft failure thought to be related to an immune reaction similar to graft rejection. Adaptation of vein allografts to the arterial environment has been studied extensively in animal models and also in humans, to a lesser degree (Conte, 1998). After implantation, the conduits undergo structural changes characterized by intimal hyperplasia and overall wall thickening (Conte, 1998). Cellular events that occur after implantation can affect the patency by occluding the conduit. Occlusion or stenosis in coronary or peripheral circulation is a common clinical occurrence present in small-caliber applications that necessitates an additional intervention (Conte, 1998). Problems that cause occlusion of a graft are thrombosis and neointimal hyperplasia (Conklin, 2002; DeMasi, 1995). Thrombosis occurs when platelets in circulating blood adhere to certain surfaces, then release chemicals to attract more platelets to form a large aggregate that generates thrombin (Stillman). Grafts most commonly fail due to the development of fibrous intimal hyperplasia where there is an excess proliferation of smooth muscle cells. This flow-restricting lesion may occur diffusely throughout the graft or, more commonly, at focal sites near anastomoses, particularly in compliance mismatched synthetic grafts (Conte, 1998).

Current processing methods only treat the tissue without removing a substantial amount of endogenous material that may harbor contaminants, such as blood and lipids, as well as antigen containing cells and cellular debris that elicit an immune reaction. Processing methods and cryopreservation preserve and retain endothelial cells and smooth muscle cells (SMC), both containing antigens that may require matching blood types for vascular reconstructions. Patients in need of an allograft must wait for a matching donor, and the waiting time for a compatible (ABO relevant) graft depends on the rarity of the recipient's blood type (Prager, 2002).

Rejection plays a significant role in failure and leads to allosensitization (Timaran, 2002). Therefore, a great deal of effort is placed in determining an ABO-compatible donor as well as lymphocyte cross-matching (Prager, 2002). The intimal layer of the conduit contains the antigen-present endothelial cells responsible for ABO relevancy. Stripping this layer of cells from the conduit removes the need for donor matching, but it is believed by some that a lack of surviving cells and endothelial integrity may play a role in graft degeneration and early and late patency (Prager, 2002). If injured and subconfluent endothelial cells line the lumen, thrombosis and SMC growth is promoted leading to intimal hyperplasia (Bader, 2000). Thus there is a need for a process which decellularizes grafts to eliminate the need for blood-typing, reduce platelet activation, and prevent smooth muscle cell proliferation that leads to neointimal hyperplasia resulting in thrombosis.

In the case of multiple revisions, insufficient autograft material, or infection due to synthetic material, a vascular allograft or xenograft is a medical necessity for life and/or limb saving operations. Currently, the demand for vascular allografts far exceeds the supply. Allograft tissue is generally obtained from cadavers and processed under aseptic conditions. Current processing methods such as using an antimicrobial soak can result in a substantial discard rate due to positive first and final cultures from bacterial and fungal contamination resistant to the cocktail aimed at achieving sterility. Additionally, the risk of transmission of viruses and other pathogens can be reduced but not eliminated through donor screening. Therefore, vascular transplantation carries some risk of disease transmission to the recipient considering the occurrence of false negative test results, human errors in screening and processing, and virological testing within the window period of contraction and detection of diseases. Over the last several years multiple examples of donor to host disease transmission have been documented. These examples include transmission of hepatitis C, bacteria, and fungi, and have resulted in serious morbidity and even mortality (Kainer, 2002). Traditional methods of sterilization, such as irradiation and ethylene oxide, have significant deleterious effects on tissue integrity that limit or preclude their use on allograft tissue.

Surgeons acknowledge that there are inherent risks in dealing with human tissue and tend to first use autograft material (DeMasi, 1995). However, patients who do not have sufficient or acceptable autografts, or are unable to receive synthetic grafts are must use allografts. To that end, the FDA has taken a recent interest in how human tissue might be held to a higher standard (Administration, 2004). This would increase the availability of allograft by reducing the discard rate and provide a safe alternative to autograft.

Factors that indicate a successful graft include one or more of the following: no aneurysms or dilations, no immunological reaction, no disease transmission, no infection and long-term patency (Bastounis, 1999; Benedetti-Valentini, 1996; DeLaurentis, 1971; Lord, 1975; Oppat, 1999). Once placed in arterial circulation, it must be capable of withstanding long-term hemodynamic stress without mechanical failure. A failure of this type could be catastrophic and lead to morbidity, such as loss of limb, or even mortality. The availability, suturability, and simplicity of handling for a graft are desirable for minimizing operating time, risk and expense as well as long-term durability. Postimplantation, the graft should be fully biocompatible, resistant to thrombosis and infection and be completely incorporated by the body to yield a neovessel resembling the native artery in structure and function (Conte, 1998; Timaran, 2002). The graft should be porous enough to permit ingrowth of tissue, but still durable and suitable to maintain anastomosis integrity.

In view of the foregoing considerations, there has been a long felt need for vascular grafts that meet the above criteria. It is an object of this invention to provide a process that creates an inert scaffold out of allograft or xenograft veins (e.g. human saphenous veins). By removal of endogenous materials the antigenicity of the graft is reduced and recipient cell repopulation is promoted following implantation, bypassing the initial graft rejection response typically seen in allograft or xenograft use. It is an additional object to provide sterile grafts by achieving an acceptable reduction in harmful organisms.

BRIEF SUMMARY OF THE INVENTION

The present technology is related to the field of sterilization and decellularization of allografts or xenografts, specifically to processes that achieve effective removal of the cells contained within a vascular tissue matrix and an effective reduction in potential harmful organisms to create grafts suitable for human implantation. As a non-limiting example, human saphenous vein samples are introduced to a sequence of chemicals with optional mechanical stimulation which provides effective sterilization and decellularization of the tissue. Since it is difficult to predict frequencies and concentrations of pathogens and infection windows may exceed the time between contraction and the time of death, inactivation of a highly resistant spore is used to determine sterility assurance. The level of decellularization is demonstrated with an immunohistochemistry stain for antigens located on the cell membranes within the tissue. The processing conditions of the present technology leave a neutralized scaffold with minimal detrimental biochemical effects on the extracellular matrix, no need for blood typing, and optimal biological functionality.

In one aspect of the present technology, a vascular graft is processed at a temperature effective for decellularization in combination with predetermined concentrations of cleaning agents (e.g. enzymes and detergents) to provide effective decellularization with minimal tissue damage. In an additional embodiment, a chelating agent is also used to enhance cell removal.

In another aspect, a vascular graft is processed at a temperature and in concentrations of cleaning agents (e.g. oxidants) effective to inactivate harmful organisms. For example, in at least one such embodiment, a process is provided for making a vascular graft more suitable for implantation into a recipient, the process comprising contacting a vascular graft with an oxidizing sterilant; and contacting the vascular graft with a cleaning solution, wherein the contacting steps are performed at a temperature less than about 45° C. and for a total contact time less than about 8 hours. In an additional embodiment, sonication is also used to enhance the process. A preferred embodiment is a 6 log reduction in harmful organisms (as demonstrated by a biological indicator). The present technology encompasses a novel process that achieves an effective level of sterility in a time that is decreased as compared to current processes.

In a further aspect, a process comprises distending vascular tissue, such as by providing a pressure gradient across a wall of the vascular tissue. Distension of venous tissue by pressurizing the lumen can be used to expand the pore volume and allow more efficient penetration of cleaning agents. This distension also reduces the amount of time used to reach effective graft decellularization. For example, in at least one such embodiment, a process is provided for preparing a vascular graft comprising at least one blood vessel, the process comprising providing a pressure gradient across a wall of the blood vessel, and contacting the blood vessel with one or more cleaning agents.

As yet another aspect of the present technology, a process comprises increasing pore volume in a vascular tissue while maintaining physiological temperatures and contacting the vascular tissue with one or more cleaning agents. For example, in at least one such embodiment, a process is provided for preparing a vascular graft from a vascular tissue, the process comprising increasing pore volume in the vascular tissue, and contacting the vascular tissue with one or more cleaning agents.

DETAILED DESCRIPTION OF THE INVENTION

Figure 1:
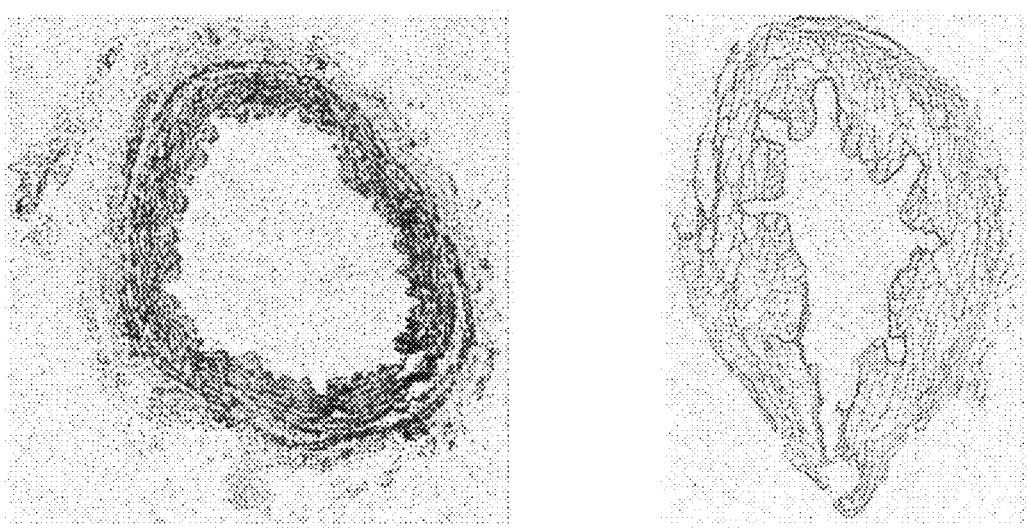
FIG. 1 is a view of positive (left) and negative (right) control samples for measurement of decellularization.

The present technology provides processes for sterilizing and/or decellularizing vascular tissue to render it suitable for use as a vascular allograft or xenograft. The processes achieve effective removal of the cells contained within a vascular tissue matrix and an effective reduction in potentially harmful organisms to create grafts suitable for human implantation. The processes can be used to treat allograft implants or xenograft implants to reduce immune reaction. The processes can be used to substantially sterilize and/or substantially decellularize vascular grafts.

Vascular tissue refers to a blood vessel, a portion thereof, one or more valves dissected from a blood vessel, a valve retained within a portion of a blood vessel, an aortic or pulmonary valve dissected and free of non-valve tissue, an aortic or pulmonary valve retained within a dissected blood vessel or cardiac tissue, or any other vascular tissue that may be suitable for use as a prosthesis. Blood vessels may include arteries and veins, portions thereof, and vascular beds containing arteries or veins. Examples of vascular tissue include, but are not limited to, small caliber vascular grafts with inner diameters of less than about 5 or 6 mm. Vascular grafts refer to any material implanted in a recipient which comprises vascular tissue and/or is used to replace vascular tissue in the recipient, such as a graft derived from, or inserted into, the vascular system of a patient. Vascular grafts may include synthetic and/or natural material or any combination thereof including, but not limited to, sterilized and/or decellularized vascular tissue.

A decellularized tissue has had the cellular component of the tissue removed, leaving the extracellular matrix of the native tissue. A decellularized tissue may include elastin, collagen, fibrin, and other extracellular proteins or non-proteinaceous compounds found in tissue.

Small caliber grafts are used in bypass and revascularization procedures in the coronary and lower extremity circulation and for arteriovenous access for hemodialysis and cancer patients. Patients most affected with reconstructions are those with End Stage Renal Disease (ESRD) requiring vascular access. The prevalence and numbers of patients that required hemodialysis has risen steadily over the past two decades. The 1999 annual report of US Renal Data System (USRDS) reported more than 30,000 ESRD patients in the US undergo maintenance hemodialysis annually (Lin, 2001). It is the most common vascular operation in the country today with the leading cause of morbidity in ESRD patients related to vascular access placement and resultant complications. Multiple access operations are often required as a result of the poor overall patency rates of hemodialysis access.

A traditional coronary artery bypass graft (CABG) surgery is estimated to be over $20,000 and within ten years, it is estimated that nearly half of saphenous vein grafts will require retreatment (Insight, 2001; Mizell, 1997). In the U.S., 20% of CABG procedures are re-operations, often due to use of unsuitable saphenous vein allografts (CryoLife, 2002). In 2001, about 80% of bypass grafts were left internal thoracid artery-LAD plus saphenous vein, 5 to 10% were bilateral internal thoracic arteries plus saphenous vein, and 1% was all-arterial conduits.

In the lower extremities, critical limb ischemia is a result of femoropopliteal occlusive disease that obstructs the blood flow into the lower limbs (Benedetti-Valentini, 1996; DeLaurentis, 1971; Linton, 1973; Prager, 2002; Stillman). It affects 10% of the population in the U.S. over 70 and 1 to 2% from 37 to 69 years of age (Stillman). About 82,000 people a year have diabetes-related leg and foot amputations which accounts for almost half of the non-traumatic amputations in the U.S. (Promotion, 1999; Promotion, 2002). The average cost for primary amputation is approximately $40,000 with an additional $30,000 for rehabilitation and related medical surgical care (Clark, 1998). Femoropopliteal disease is caused by atherosclerosis, which is a form of arteriosclerosis. Occlusion occurs in the distal common artery (34%), distal popliteal artery (14%), or tibial arteries (Stillman). The vessels eventually become thrombosed due to turbulent flow (Alexander, 1996; Stillman).

At early stages, occlusion forces blood to perfuse the limb via collateral pathways, thus, compromising the circulation. Blood flow is sufficient at rest, but as activity increases, the supply of oxygen to leg muscles is inadequate causing intermittent claudication (Stillman). As the disease progresses, outflow may be impaired even at rest, resulting in severe ischemia pain, tissue necrosis (gangrene) or claudication resulting in the need for intervention (Alexander, 1996; Castier, 1999; DeLaurentis, 1971; DeMasi, 1995; Faries, 2000; Linton, 1973; Londrey, May 1991; Lord, 1975; Oppat, 1999; Prager, 2002).

Approximately 100,000 vascular reconstructive procedures for limb salvage are performed yearly in the United States (Stillman). Numerous studies show the effectiveness of infrainguinal revascularization in producing long-term patency and improved limb salvage rates (Faries, 2000). The procedure involves increasing pathways and runoff for inflow from the common femoral artery to lower limb vessels (DeLaurentis, 1971). The different procedures involve above knee bypasses from the common femoral to the popliteal artery, or below knee bypasses from the common femoral artery to either the popliteal or tibial artery or from the superficial femoral artery to the popliteal artery (Bastounis, 1999; DeLaurentis, 1971). The choice of an above or below knee bypass procedure depends on the extent of the popliteal artery disease (Oppat, 1999). Autologous saphenous vein is the graft of choice for critical limb ischemia, but up to 45% of the patients do not possess usable veins (Faries, 2000; Prager, 2002; Timaran, 2002). The need for alternative conduits has become increasingly evident considering the number of multiple procedures performed to salvage a single extremity (DeLaurentis, 1971; Faries, 2000; Timaran, 2002).

Anatomy and Physiology

Blood vessel walls consists of three layers of which the proportions vary according to the size of the vessel The inner most layer is known as the intima or tunica interna and is made up of an endothelial layer and basal lamina. The endothelial layer lines the lumen with the underlying connective tissue containing variable amounts of elastic fibers (Fung, 1993; Martini, 2001). The layer of epithelium consists of flat cells that are metabolically active and produce a number of compounds that affect the vascular lumen diameter and control activation of platelets (Fung, 1993). The cells act as a barrier that controls the entry of substances into the wall, but allows some to pass via transport system. The compounds secreted control blood coagulation and relaxation and contraction of the smooth muscle cells in the middle layer. The basal lamina (basement membrane) is a thin layer of noncellular material with a filamentous texture underlying the epithelium. The principal component of this connective tissue is collagen, typically type IV (Fung, 1993). Separating the intima from the middle layer are elastic fibers called the internal elastic membrane (Martini, 2001).

The middle layer of the blood vessel wall is the media or tunica media. It is the thickest layer of the arteries and is smaller in their vein counterparts. It mostly contains smooth muscle cells oriented in concentric sheets within connective tissue. This layer is involved in the contracting and relaxing of the tissue and contains elastic sheets and bundles of collagen fibrils, each of which contributes to the mechanical behavior of the vessels (Fung, 1993). The amount of each substance affects the ultimate mechanical properties and distinguishes arteries from veins. The collagen fibrils are made up mostly of type III with some type I and a trace of type V.

The outermost layer of the blood vessel wall is the adventitia or tunica externa. It forms a connective tissue sheath around the vessel connecting it to the body forming the vascular network. The outer layer is divided from the media by the external elastic membrane which is a thin band of elastic fibers (Fung, 1993; Martini, 2001). The outermost layer mainly contains collagen fibers (similar types and proportions as the media) and ground substance with scattered bands of elastin fibers (Fung, 1995; McClurken, 2001). Also contained within the tissue layer are fibroblasts, macrophages, minute blood vessels (vasa vasorum), myelinated and non-myelinated nerves.

Similarities and differences in veins and arteries can be seen in Table 1. The relative wall thickness of veins is lower than in arteries. While the media is the largest layer in the arteries, the adventitia is the largest layer in the veins with a large amount of collagen, networks of elastic fibers and bundles of smooth muscle cells. The vein media is thin with relatively few muscle cells and very little elastic tissue (Fung, 1993; Martini, 2001). The intimal layer of veins contains valves to prevent backflow since the pressure in the veins is so low they cannot oppose gravity.

TABLE 1

Features of typical arteries and veins (Martini, 2001).

| Feature | Typical Artery | Typical Vein |
|---|---|---|
| General appearance in sectional view | Usually round, relatively thick wall | Usually flattened or collapsed with relatively thin wall |

TABLE 1-continued

Features of typical arteries and veins (Martini, 2001).

| Feature | Typical Artery | Typical Vein |
| --- | --- | --- |
| Intima | | |
| Endothelium | Usually rippled due to vessel constriction | Often smooth |
| Internal elastic membrane | Present | Present may be poorly developed |
| Media | Thick, dominated by smooth muscle and elastic fibers | Thin, dominated by smooth muscle and collagen fibers |
| External elastic membrane | Present | Absent |
| Adventitia | Collagen and elastic fibers | Collagen, elastic, smooth muscle fibers |

The muscular and elastic components permit controlled alterations in the diameter of the vessel as blood pressure or blood volume changes. Arteries have thicker walls with the media containing more smooth muscle and elastic fibers. The collagen fibers are crimped while the elastic fibers recoil and restrict the lumen when not opposing pressure generated by the pumping of the heart to retain its cylindrical shape. The endothelial lining shows pleats in a sectional view since it cannot contract along with the elastin. Veins have larger diameters and thinner walls than their corresponding arteries. Due to the lesser amount of elastin present the walls of the veins collapse when excised.

Bypass Grafts

Autograft:

Autograft refers to tissue transplanted from one part of the body to another in the same individual. The saphenous vein is the most common small-caliber (<5 mm) graft for coronary bypass, arteriovenous access (AV), and lower-extremity reconstructions. According to Deweese, the advantage of autograft is its long-term patency even despite poor outflow conditions. It is believed this may be attributed to the smooth inner lining or pseudointima, which appears almost immediately in vein autografts as opposed to allografts and, to a lesser degree, synthetic grafts (Alexander, 1996; DeLaurentis, 1971; DeWeese, 1994). Lower extremity, long-term results for infrapopliteal and even pedal arteries are excellent with patency at 5 years of 50 to 80% (Bastounis, 1999; Conte, 1998; Linton, 1973).

However, up to 45% of patients seen with critical limb ischemia do not possess usable greater saphenous vein and require postoperative revision surgery in four to five years (Alexander, 1996; Bastounis, 1999; Benedetti-Valentini, 1996; Conte, 1998; DeLaurentis, 1971; DeMasi, 1995; Faries, 2000; Linton, 1973). Some problems that preclude the use of an all-autogenous graft are a possible size mismatch between the donor site vessel and the vessel to be repaired, insufficient length or diameter, prior use, previous graft problems such as infection in that site, fibrosis, or venous disease.

As the number of procedures increase, as do for patients with atherosclerosis and ESRD, the supply of autograft is greatly reduced. Many patients lacking suitable autograft tissue with recurrent coronary disease are considered inoperable and those with distal lower extremity disease may suffer loss of limb (Conte, 1998). Therefore, graft failure and conduit availability are limitations to autograft uses. Possible alternatives to autograft use include, but are not limited to prosthetics, composite prosthetic and autogenous grafts, allografts, and xenografts.

Synthetic:

Patients without adequate autologous tissues may be considered for an all-synthetic or a prosthetic-vein composite replacement, with materials such as polyurethanes, Dacron (polyethylene tetephthate) or expanded polytetraflourethylene (ePTFE) (Conklin, 2002; Gupta, 1997). Synthetic material has the advantage of being an off-the-shelf product and is not a limited supply. For large-caliber arterial reconstructions, the long-term results for replacement of common femoral arteries for either aneurismal or occlusive disease with available synthetics are generally good. However, prosthetic grafts have proved to be unfavorable as small-caliber arterial substitutes in demanding, low-flow environments resulting in occlusions (Conklin, 2002; Conte, 1998). Synthetics nave been used with moderate success in lower extremity bypasses to the popliteal artery and some success to tibial vessels, but the effectiveness of below knee revascularization is inferior to all-autogenous grafts used in a majority of studies (Faries, 2000; Gupta, 1997). The four year patency rate for ePTFE is only 12 to 14% in infrapopliteal and aorta-coronary bypass and are reconstructed twice as often as autologous for arteriovenous (AV) access (Gabriel, 2002). PTFE grafts for arteriovenous (AV) access are reconstructed twice as often as autologous (Lin, 2001). Complications, such as infection and occlusion, lead to the need of graft removal, intravenous antibiotic treatment, debridement and drainage, placement of a catheter or an AV graft replacement. Due to multiple revisions in hemodialysis patients for AV access, available sites in the upper extremities become scarce.

Some synthetics show good biocompatibility, strength and deformation but eventually creep and lead to the development of an aneurysm (Gupta, 1997). The most common failure modes for synthetic grafts are thrombosis due to the adhesive nature of cells to the synthetic surface and development of focal anastomotic strictures because of neointimal hyperplasia resulting from compliance mismatch and material properties, and poor outflow (Conklin, 2002; DeMasi, 1995; Lin, 2001; Linton, 1973). In general, the grafts never completely heal and have limited re-endothelialization mostly in the area of pannus ingrowth adjacent to anastomoses (Conte, 1998). Additionally, infection is a common problem with synthetics which causes sensitization and precludes the patient from revisions with synthetics. A major clinical problem with infection is it leads to high mortality rates, excessive bleeding, aortointestinal fistulas, and major amputations of limbs (Gabriel, 2002).

Allograft:

Allograft is tissue taken from a donor of the same species. Vascular allografts are often deemed to be a medical necessity for patients who need revision surgery and either do not have sufficient saphenous autografts, or are unable to receive synthetic grafts due to sensitization or risk of renal failure. In the early days of vascular surgery, allografts were used but were soon abandoned for poor long-term success due to the high rate of aneurysm formation and dissections of vessels with secondary dilatation and calcification due to biodegeneration (Castier, 1999; Conte, 1998; Prager, 2002). However, improvements in recovery techniques, storage, and cryobiology have revived the use of allograft tissue. Allografts provide the advantage over autografts of reduced operating and anesthesia time, reduced operative trauma, limited incisions and reduced wound complications, all of which should be considered, especially in elderly patients (Prager, 2002; Timaran, 2002).

Hemodialysis patients frequently need a replacement graft as treatment for an infected arteriovenous (AV) access graft (Lin, 2001). Additionally, saphenous vein (SV) allografts have been used to save limbs in below knee revascularizations due to flexibility, compliance matching, size matching, and resistance to infection (Castier, 1999). Vascular allografts have been promoted by some studies as the best alternative conduit for infrainguinal arterial reconstruction in infected fields when autologous veins are unsatisfactory or unavailable (Timaran, 2002). For the coronary circulation, the internal mammary artery (IMA) and the radial artery are used as bypass allografts. The IMA has been shown to have long-term patency, but availability is severely limited due to its short lengths and difficulty in recovery (Conte, 1998).

As mentioned above, two potential disadvantages to the use of allograft tissue are the risk of contamination or disease transmission and early to late occlusions. Good tissue banking practices utilized to prevent an occurrence include intensive screening of all potential donors, including medical and social history and various required data to determine if the donor is acceptable. Additionally, tissue and blood samples are screened with microbiological testing and serological testing, respectively. The blood samples are virologically screened for HIV, hepatitis B, hepatitis C, and CMV (Prager, 2002). Tissue samples follow the grafts through all of the processing steps in order to detect potential tissue infection following recovery. The contamination problem of vascular allografts is centered on recovery, sterilization, and storage. Incidents of contamination can occur at recovery if the barrier to the digestive tract is compromised. Preparation and evaluation of the tissue for implantation requires extensive handling under aseptic conditions which adds opportunities for contamination. Several previous methods for sterilization of allografts such as antimicrobial solutions, gamma-irradiation and ethylene oxide have proven to be inefficient or too destructive (Almond, 1966; Beach, 1972; Bolooki, 1972; Bowman, 1969; Innes, 1971).

Xenograft:

Xenograft is tissue taken from a donor of a different species. Xenografts provide the same advantages over autografts as allografts (i.e. operating and anesthesia time, reduced operative trauma, limited incisions and reduced wound complications). These grafts also require processing to remove antigens and decellularize the graft. However, due to the fact that the antigens may not be native to the recipient species, these grafts may require more extensive processing conditions. For example, Conklin investigated decellularization of a small-caliber xenograft with a porcine common carotid artery model (Conklin, 2002). This group followed cell lysis with multiple enzymatic digestions and detergent washes while agitated. In general, previous methods for sterilization of xenografts have also proven to be inefficient (time-consuming) and/or too destructive to the tissue.

Allograft and Xenograft Processing: Sterilization and Disinfection

The active surveillance activities and the outbreak investigation carried out by CDC during 2002 highlights the fact that the spectrum of bacterial pathogens associated with allograft-associated infections include Gram positive (*S. aureus* and *Enterococcus*) and Gram-negative bacteria. The importance of validating any sterilization technique against a mixture of pathogens is underscored by the fact that 19% of the allograft-associated infections ascertained during the active case finding period were polymicrobial. The frequencies and concentrations of various pathogens in polymicrobial infections remain unknown and will vary from recipient to recipient and are unpredictable.

Current disinfection methods use an antimicrobial soak in which the tissue is aseptically processed with antimicrobial and sometimes antifungal cocktail. A study to evaluate the effectiveness of the antibiotic cocktails used by a tissue bank for disinfection of human tissue was conducted by a testing laboratory (AppTec, Marietta, Ga.) that is compliant with both Good Laboratory Practices (GLP) and Good Manufacturing Practices (GMP), which are regulations set forth by the Food and Drug Administration (FDA) that requires manufacturers of human drugs and biological products, animal drugs, medical devices, and food additives to demonstrate safety and utility of their product. Saphenous vein samples were inoculated with 106 of aerobic, anaerobic and a mixture of test organisms suggested by the CDC for validation. The result was a one log reduction or less with absolutely no effect detected in the *Clostridium* species (Alexander, 2004).

Patients are generally protected from contaminated tissue since the donor tissue will be discarded if representative samples tests positive for contaminants, but in the past some methods for testing sterility have been shown to be flawed (Waterworth, 1974). Specifically, residual antibiotics from the treatment process have been shown to inhibit growth in post-treatment surveillance cultures producing false-negative results leading to cases of septic arthritis, hepatitis C transmission, *Streptococcus pyogenes* (GAS), and *Clostridium* spp. (Hepatitis, 2003). Of note, cases of soft tissue allograft-associated disease transmission by spore-forming organisms that are resistant to antimicrobial solutions have been reported within the last few years (Hepatitis, 2003). These tissues have predominately been cartilage used in joint repairs, but investigations prompted by these events have revealed transmissions and infections resulting from other soft tissue grafts such as tendons and saphenous veins. Vascular tissue is less prone to infection than cartilage, but it is still vulnerable to organisms (including fungi and viruses) inherent in the donor or transmitted during recovery or processing that are resistant to some antimicrobials currently used for allograft disinfection. Additionally, infection can occur and, in some cases, the rapid onset of infection and the infecting organism itself suggest that graft to host disease transmission was responsible rather than infection from some other source implementing the graft as the carrier (Clark, 1998; Reller, 1975; Silver, 1971). More recently, analysis of the infecting organism's DNA has provided even more convincing evidence that donor to host transmission of infection has occurred.

Preservation of graft tissue is also a necessity. The primary goal of a preservation technique is to increase vein graft availability by extending its shelf-life. In the process, the graft should have minimal antigenicity while viably functional and maintain structural integrity similar to native vein (Lin, 2001; Timaran, 2002). The use of cryopreservation of vascular conduits for long-term storage has been used as a means of viral inactivation in addition to reducing antigenicity, but a process that has even greater effectiveness and smaller risk of viral disease transmission is desirable.

Cryopreserved veins are commercially available from various sources including RTI Cardiovascular (Birmingham, Ala.). The common method for preserving graft tissue is to place the vessels in a buffered solution containing cryoprotectants, such as DMSO, and then store in the vapor phase of liquid nitrogen (−110° C. to −196° C.) (Lin, 2001; Timaran, 2002). An antimicrobial solution may be used initially to disinfect the tissue prior to storage. As the tissue is transferred from the disinfectant solution to the freezing solution, representative samples are removed for sterility testing according to United States Pharmocoepia (USP) standards. The tissue is frozen in a controlled manner from +4° C. to −80° C. or below at an average rate between 0° C. minute and 5° C./minute. The cryopreserved vessels are then stored in freezers with the vapor phase of liquid nitrogen. Thawing and rinsing are performed aseptically. The rinsing procedure must be performed immediately after the thawing procedure. The allograft package is first thawed at room temperature and then in warm saline (32° C. to 42° C.). The saline step is supposed to rapidly thaw the tissue without adversely affecting cellular viability (Lin, 2001; Timaran, 2002). The graft is then aseptically removed from packaging, flushed and soaked with a series of solutions to remove cryosolution components before implanting.

Freezing with cryoprotectants prevents the intracellular vapor phase gradient that is created when the extracellular matrix freezes. The cytoplasm remains in liquid form and causes cellular membrane disruption, which supposedly produces a nonviable graft. The cryoprotectant protects the matrix from structural damage by replacing the water and preventing ice crystal formation (Lin, 2001). Without cryoprotectants, saphenous vein allografts have been associated with high graft failure rates in infrainguinal bypass procedures (Timaran, 2002). At the same time, an ideal method of cryopreservation has not been determined. Experimental and clinical data suggests that current cryopreservation protocols may make allografts more brittle and could induce early graft rupture or dilatation. Cryopreserved veins are prone to fissuring during thawing which degrades the strength and performance of the graft. Therefore, aneurismal degeneration continues to be a matter of concern. This may be due to preservation of the endothelial antigenic properties as wells as inadequacy of the structural and functional media characteristics (elasticity and compliance) (Timaran, 2002).

Investigations on cryopreserved vessels show evidence of antigenicity and rejection. The development of intimal hyperplasia that leads to graft failure is compounded and accelerated by immune-mediated inflammatory response secondary to rejection, the effect of cryoprotectants, surgical injuries and Theological mismatch (Timaran, 2002). Explanted tissue has shown cellular infiltrates that correlates with wall hemorrhage and necrosis (Timaran, 2002). Venous allografts appeared to induce anti-HLA antibodies post implantation and an associated humoral immune response contributing to failure. Most inflammatory cells are activated by cytotoxic T cells, expressing CD3, CD8 and HLA-DR antigens. On the other hand, when compared to an acellular graft, PTFE, cryopreserved saphenous vein allograft showed no significant difference in T-cell subpopulations or lymphocytotoxic antibodies (Lin, 2001). Immunohistochemical examination showed minimal mononuclear cell infiltration in adventitial layer indicating no significant immunological activation or clinical rejection. Contradictory results on the preservation of the endothelial layer and smooth muscle layer show improvement in patency rates in animal studies while no clear benefit in humans has been discovered (Lin, 2001; Timaran, 2002). This is most likely due to the freshness and young age of the tissue in an animal study compared to the older population of human donor tissue that may take as long as 24 hours to recover.

The ultimate immune response may also be directed against smooth muscle cells when the endothelial layer is absent or subconfluent. Allosensitization occurs due to expression of class I and II major histocompatibility complex (MHC) antigens present on preserved endothelial cells as well as non-MHC antigens that stimulate T-cell mediated rejection response (Lin, 2001; Timaran, 2002). Immunologic mechanisms have been implicated in early thrombotic occlusion and poor patency rates in lower extremity revascularization with cryopreserved allograft (Castier, 1999; Conte, 1998; Prager, 2002). There has been evidence of the development of intimal hyperplasia and late graft failure due to the replacement of the smooth muscle cell layer by fibrotic layers after implantation (Lin, 2001; Timaran, 2002). Additionally, the structural integrity can be compromised with remodeling by structural reorganization of the graft and thickening of the intima from smooth muscle cell proliferation. This is followed by a gradual decrease in compliance from fibrosis in the layers as well as immediate disintegration of immunocompetent cells and release of proteases that probably cause elastin degradation (Gabriel, 2002). Elmore et al. found similar contractile characteristics and graft patency rates but some cellular differences when comparing noncryopreserved to cryopreserved grafts in canine femoral arteries (Lin, 2001). There was a decrease in smooth muscle cell relaxation response to nitric oxide (NO) in cryopreserved grafts as well as decreased relaxation to phenylephrine and endothelin (Lin, 2001; Timaran, 2002). Other studies have found pathophysiological processes develop in the walls and gradually lead to stenosis, mainly at anastomosis, and segmental dilation and believe that chronic transplant rejection reaction is responsible.

A disadvantage to cryopreservation is related to the second issue raised with the occlusion of allograft veins that is most likely due to an immune reaction similar to a graft rejection response. Since endothelial cells, smooth muscle cells and fibroblasts contain antigens on their cell membranes, preservation of these components could theoretically have deleterious consequences by mediating immunological reactivity (Castier, 1999). Additionally, preserving these cells creates the need to consider ABO-compatibility and lymphocyte cross-matching (Prager, 2002). Since there is a limited availability of allograft arteries, a long waiting list may be a problem limiting widespread use.

Blood typing is used for vascular grafts to prevent rejection since simply inactivating contaminants is not sufficient protection. There is a limited availability of vein allografts due to ABO relevancy and a depletion in inventory because of positive cultures (Prager, 2002; Timaran, 2002). ABO matching contributes to this deficiency, but only ABO compatibility has been evaluated in most studies (Timaran, 2002). Simply matching blood type is not sufficient to prevent an immune response. Human leukocyte antigens (HLA), proteins found on most cells, are used by the immune system to distinguish between endogenous and foreign cells. Additionally, there are many HLA antigens, so HLA matching is not feasible for clinical applications and the role of matching HLA and ABO for humans has not been determined (Prager, 2002; Timaran, 2002). Again, removing the cells from the graft would alleviate the problems with finding the appropriate donor.

It is believed that the difference in allograft healing compared to autograft healing is mainly due to this immunologic response. This contributes to the low patency rates seen in allograft use. Graft rejection is a response to class I and class II MHC antigens laden on the membranes of endothelial cells (Lin, 2002). This layer is in immediate contact with inflammatory cells in blood such as neutrophils, monocytes, and macrophages (Martini, 2001; Mirelli, 1999). Rejection plays a significant role in failure and leads to allosensitization (Timaran, 2002). Other studies have found pathophysiological processes develop in the walls and gradually lead to stenosis, mainly at anastomosis, and segmental dilatation that may be a result of chronic transplant rejection.

Some studies suggest that an intact endothelium may be a prerequisite for improved long-term patency of autologous and alloplastic bypass grafts (Prager, 2002). The endothelium is an active barrier that allows permeability to fluid and macromolecules while limiting entry of inflammatory cells (polymorphonuclear cells and monocytes) and immune effector cells (B and T lymphocytes). It is involved in inflammation as well as maintaining a nonthrombogenic surface by maintaining normal platelet activation (Silverstein, 1999). Under normal conditions, this cellular response creates a nonthrombogenic surface preventing inappropriate platelet activation. Cryopreserved veins boast at the most approximately 70% viability, leaving an insufficient endothelium that is not fully functional. When dysfunction in the endothelium occurs, pathological processes result, leading to endothelial cell activation and thrombus formation. There is an injury response with inflammation and wound healing where thrombin and fibrin are generated and platelets are activated. The graft begins to occlude with loss of patency and early graft failure. Hence, there is a need to remove as well as inactivate infectious agents without damaging the allograft tissue itself.

Chronic rejection also affects the vascular wall with medial destruction where the arterial wall dilates and possibly ruptures (Allaire, 1994). Davies compared the healing response of allograft to autograft in a rabbit model with a common carotid artery bypass (Davies, 1997). They found there were two phases in the response. The first phase consisted of significant thickening of the intima and media compared to autograft. The second phase showed a 51% decrease in the intimal thickening and a maintained medial thickening of 97% compared to autograft. The allograft had an exaggerated medial response while the autograft had an exaggerated intimal response. Overall, there was a net increase of 17% in allograft wall thickness compared to autograft. Even so, the lumen between the two sets of grafts was not significantly different after 28 days.

A similar medial response was seen in an abdominal aortic graft model in rats but the lumen appeared to occlude. There was medial cell loss and matrix degeneration, adventitial inflammation, and intimal hyperplasia. The lumen narrowed by intimal cell proliferation that was found to express α-actin, a marker for smooth muscle cells and fibroblasts. The smooth muscle cells were destroyed and the elastic lamina became dislocated and fibrosis was noted (Allaire, 1994; Ketchedjian, 2005; Wilson, 1995). The inflammation in the adventitia disappeared along with the removal of the SMCs. This gives credence to the antigen induced response by both the endothelial cells and SMCs (Allaire, 1994; Ketchedjian, 2005).

Though the inventor does not intend to be bound by theory, it is submitted that cell viability may not be entirely beneficial since it maintains its antigenicity which has led to the use of short term immunosuppressant and anticoagulation therapies (Prager, 2002; Timaran, 2002). The use of immunosuppression and anticoagulation therapies, along with cryopreservants with controlled freezing, has been shown to improve patency and graft acceptance to combat cryopreserved conduits more thrombotic behavior early on (Lin, 2001).

Posner et al. showed improved one year patency with infrainguinal arterial reconstruction with low-dose immunosuppression treatment (Posner, 1996). They also showed a substantial number of allograft-related complications with early degeneration, pseudoaneurysm formation, and hemorrhaging. An improvement in graft patency in animal models and human arterial allograft patency is seen with high-dose immunosuppressive treatment, whereas, the low-dose regimens were not enough to curtail the allogeneic response (Timaran, 2002). The more potent treatment may be effective, but the toxicity level may not be tolerated by older patients with multiple comorbidities as well as increasing the risk of infection, with reduced graft rejection, but disturbed wound healing, and possibly gangrene (Prager, 2002). Therefore, patients with infected tissue necrosis, an indication for surgery, would be at greater risk if the immune system is compromised with treatment. One study where patients received high-dose immunosuppression for kidney transplants did not prevent rejection (Timaran, 2002). A histological and immunohistochemical analysis of the renal arterial allografts of the failed kidney transplants showed evidence of chronic rejection and intimal hyperplasia in the vessel walls. Most patients with critical limb ischemia will have reduced renal function. Exposing them to therapy may lead to further reduction of renal function (Prager, 2002). In one study, treatment was discontinued in 12% of the patients due to gastrointestinal bleeding (Timaran, 2002). These conditions preclude a large population of the patients needing revascularization from receiving cryopreserved grafts if immunosuppression is required.

Experimental and clinical studies on cryopreserved veins show that many functional features of the endothelial cells and smooth muscle cells are preserved (Lin, 2001; Timaran, 2002). These properties are prostacyclin and endothelin production, fibrinolytic activity, thrombotic properties, platelet deposition, and metabolic mechanisms. However, after implantation some studies show the presence of an intact endothelial layer while numerous animal studies and some clinical studies shows moderate endothelial denudation to complete loss of endothelial cells after implantation (Lin, 2001). It seems in some preservation protocols the endothelial layer may no longer be bound to the graft and is removed in the circulatory flow negating the efforts made to maintain and preserve that layer. The loss of the lining and smooth muscle cells are due to the inability of the preservation process to maintain complete cell viability resulting in a loss of adherence to the basement membrane. This is presumably due in part to a more rapid accumulation of low-density lipoprotein cholesterol compared with noncryopreserved human saphenous vein grafts (Lin, 2001; Prager, 2002; Timaran, 2002). Other possible factors are toxicity of the preserving agents (particularly with antibiotics), cryopreservation events, spontaneous cell death, or destruction of the surviving cells by immunocompetent host immune cells (Prager, 2002). Additionally, the ischemic time for allograft tissue varies up to a 24 hour period resulting in variable cell viability prior to cryopreservation.

Thus a potential disadvantage of the use of allograft is its biologically active components containing antigens, which could lead to allosensitization, resulting in an immune reaction and rejection. Cryopreserved grafts retain viable or nonviable cells which still contain the antigenicity present in the protein structure of the cell surface. This has led to the investigation of decellularized conduits for vascular reconstruction. There is a general consensus among investigators that removing, instead of merely inactivating, the cellular content may reduce or prevent an immunological response.

Biologically active endothelial cells express class I and class II major histocompatibility complex antigens that result in an immunological response (Madden, 2002). Human studies using antibiotics and cryopreservation to process allografts have demonstrated a panel of these reactive antigens, some of which caused a broad recipient allosensitization (Hawkins, 2000; Madden, 2002). This is of particular interest in patients with end-stage renal disease awaiting a kidney transplant. The presence of alloantibody could preclude renal transplant due to cross-match since these patients are already immune compromised with decreased functioning of white blood cells (Madden, 2002).

There is controversy in the literature as to the allosensitization of cryopreserved grafts. The levels of panel reactive antigens (PRA) in patients whom received cryopreserved vein grafts showed allosensitization within approximately 3 months with an 84.1% increase (Madden, 2002). Although, when compared to decellularized grafts (SynerGraft, CryoLife, Inc.) there was no significant difference in primary, assisted primary or secondary patency. A study of cryopreserved saphenous (SV) allograft in lower extremity revascularization yielded poor patency rates that was believed due to immunological reactions. These, and other recent studies demonstrated venous tissue expresses class I and class II major histocompatibility (MHC) antigens present on the preserved endothelial cells as well as non-MHC antigens that stimulate T-cell mediated rejection response (Hawkins, 2003).

If injured or subconfluent endothelial cells that line the lumen are present, thrombosis and smooth muscle cell (SMC) growth is promoted leading to intimal hyperplasia (Bader, 2000). This is likely due to the major antigenic determinants, class I and class II MHC, present on the SMC. Therefore a denuded vessel leaves no protection from an immune reaction. It has been shown that the endothelial cells of cryopreserved vessels are not fully viable or confluent and slough off into the blood stream after implantation.

Rejection plays a significant role in failure and leads to allosensitization. Allosensitization was demonstrated in patients who received cryopreserved allografts in a SynerGraft (CryoLife, Inc) study. Blood tests showed an increase in PRA levels partly due to exposure to the allogeneic antigens on the preserved endothelial cells. A study of cryopreserved saphenous vein allografts in lower extremity revascularization yielded poor patency rates that were likely due to immunological reactions. Another study using aortic valve allografts (AVA) showed early failure caused by donor-specific immune response (Grauss, 2003). Preserved vessels used for hemodialysis access caused allosensitization with increased PRA levels. This can be a potentially serious problem for kidney transplant recipients since the presence of alloantibody could preclude a renal transplant due to cross-match incompatibility (Madden, 2002).

Chronic rejection can cause vascular wall destruction making the graft unsuitable for long-term applications. The medial layer is destroyed with altered extracellular matrix leading to wall dilatation and rupture (Allaire, 1994; Wilson, 1995). This event could be catastrophic in a coronary site that may lead to morbidity or mortality. The cellular events that occur was modeled in abdominal aortic grafts in a rat model by several researchers and summarized by Allaire (Allaire, 1994). There is medial cell loss and matrix degradation, adventitial inflammation, and intimal hyperplasia. This is a typical response for immune injury in arterial allografts (Allaire, 1994). Through the response, the media is thinned and the elastic lamina is dislocated (Allaire, 1994; Wilson, 1995). Smooth muscle cells are destroyed while inflammatory cells invade the adventitia, most likely due to the antigens present on the SMC since the inflammatory cells disappeared when the SMCs disappeared (Allaire, 1994; Ketchedjian, 2005; Wilson, 1995). The response results in degradation of the matrix, fibrosis and functional failure. Additionally, the graft is occluded by narrowing of the lumen caused by the intimal cell proliferation thickening the vascular wall. Current strategies to reduce or prevent this cascade of events are immunosuppressives drugs or reducing the antigenicity of the graft with cross-linking agents, such as gluteraldehyde, or by sequential chemical treatments that promotes tissue decellularization.

Decellularization involves the removal of major immunogenic components such as cells and their lipid membranes, membrane associated antigens and soluble proteins, and other lipids and more soluble glycosaminoglycans (Kasimir, 2003; Wilson, 1995). Primarily present on the endothelial cells and also present on SMCs are class I and class II major histocompatibility complex antigens. A 10 and 20 week sheep study with an allograft patch model showed only 1 out of 8 sheep with a decellularized graft demonstrated a positive elevation in PRA levels to MHC I and none to MHC II. In the classically cryopreserved group, ⅔ of the sheep showed an elevation (Ketchedjian, 2005). The resulting graft is an acellular scaffold with only insoluble structural proteins, such as collagen for strength and elastin for distensibility (Hilbert, 2004; Kasimir, 2003).

Decellularized grafts have been evaluated histologically, immunohistochemically, mechanically and with both animal studies and clinical studies. Hilbert evaluated the morphologic characteristics in a small-diameter freeze-dried decellularized carotid artery of a goat decellularized with a non-ionic detergent solution. Histological analysis showed complete endothelial cell removal while preserving the basement membrane. Additionally, no cells were seen in the intima, media or adventitia, although, there were remnants of smooth muscle cells in the media without nuclei. The extracellular matrix seemed well preserved, but oval to circular spaces were occasionally noted in the media. The internal elastic lamina remained intact, as well as the layered elastic laminae in the media (Hilbert, 2004).

In an animal study conducted by Hilbert, all allografts had patency upon explantation with no significant dimensional changes or aneurism formation. The autografts showed a luminal surface lined with a layer of endothelial cells while the allograft showed a discontinuous layer. Even in these regions of incomplete endothelialization thrombi were not observed. Both types of grafts showed myofibroblasts, collagen and proteoglycans that may be indicative of incorporation (Hilbert, 2004).

The allograft appeared relatively acellular in the media with focal cellular regions among the dense collagen and elastic lamellae containing infiltrated myofibroblasts of the hosts. The authors believe that the number of host myofibroblasts in the media may have been significantly limited by the presence of the dense collagen bundles and smooth muscle cell remnants. Host cell migration was most apparent close to the anastomoses and was rich in proteoglycans. It appeared to occur in the adventitia along the length of the grafts. Histologically, there was no evidence of calcification and inflammatory cells were not present in the graft wall. Electron microscopy did show calcification of minute remnants of cell membranes. Ingrowth of host blood vessels were not observed after 6 to 7 months (Hilbert, 2004).

Conklin investigated decellularization of a small-caliber xenograft with a porcine common carotid artery model (Conklin, 2002). This group followed cell lysis with multiple enzymatic digestions and detergent washes while agitated. Histology and electron microscope showed complete removal of cellular components while the extracellular matrix appears to remain intact. Hematoxylin and eosin (H&E) stain showed no signs of remaining nuclear material in the walls of the vessels and TEM showed complete removal of cellular material from the media layers. Histology showed an intact internal elastic lamina along with elastin lamellae in the media. TEM showed the basic extracellular microstructure remained intact after processing.

In addition to reducing immune reactions and decreasing the thrombogenicity of the luminal surface by decellularization, the Conklin group wanted to ensure that the process would maintain a graft with similar mechanical properties to the native vessel, high strength and good handling characteristics. Processing with chemicals or treating with a cross-linker may affect the integrity of the matrix in focal regions leading to aneurysm post implantation; weakening of the graft, or making it stiffer and more brittle. They investigated the compliance and burst strength of the vessels on a custom-built system that measures the diameter changes while increasing the intraluminal pressure. The compliance is expressed as the percentage diameter change per mm Hg change in pressure normalized to the compliance of fresh vessels. The average compliance was calculated as the slope of the linear regression line in the physiological pressure range (70-130 mm Hg).

The mechanical analysis was performed on decellularized vessels, decellularized and heparin-treated vessels, fresh vessels, alcohol preserved vessels, and ePTFE prosthetic grafts. The ePTFE grafts were the least compliant ($\Delta D$/mm Hg 0.024%) and the decellularized grafts were slightly more compliant ($\Delta D$/mm Hg 0.181%) than the fresh vessels ($\Delta D$/mm Hg 0.172%). Alcohol caused the tissue to stiffen some (0.160%) while Heparin treatment produced a much stiffer graft (0.0975%). During burst testing, none of the fresh vessels burst within the limit of the pressure transducer (2300 mm Hg). One out of four of the decellularized vessels burst within the limit at 1654 mm Hg. Although there may be some strength loss measured in that one vessel, there still is a high safety margin over ten times the physiologic pressure. Only four samples were tested in this group.

This group examined their decellularized process with heparin cross-linking on a carotid artery bypass in dogs. At 24 days, fibroblast-like cells appeared to densely populate the media and there were few endothelial-like cells lining the lumen. After two months, dense $\alpha$-actin staining suggested smooth muscle cells densely populated the vessel wall and Factor VIII staining confirmed that endothelial cells lined the lumen.

Teebken et al. developed an acellular vascular xenograft matrix from porcine thoracic aortas for the purpose of seeding with human cells (Teebken, 2000). This group decellularized with enzymatic cell extractions using biological enzymes trypsin, ribonuclease (RNase) and deoxyribonuclease (DNase). It is contemplated that these enzymes are capable of removing cell components as well as cellular antigens, lipids and to some extent glycosaminoglycans with limited toxicity. Light microscopy showed no cell nuclei or intracellular components in cross-sections of the aortic wall after processing. Immunohistochemical stains for fibroblasts and endothelial cells were all negative. SEM showed extracellular matrix fibers with openings of 1 to 10 μm.

Schaner studied the composition and strength of decellularized human greater saphenous vein specimens to determine their potential as a vascular tissue-engineering scaffold (Schaner, 2004). This group used a detergent, sodium dodecyl sulfate (SDS), as a decellularizing agent. Transmural cell removal was found to be nearly complete (>94%) at a concentration of 0.075% SDS. The luminal surface appeared completely devoid of endothelial cells at all concentrations tested. The collagen morphology appeared unchanged, the basement membrane remained intact and the elastin staining decreased only slightly.

This group also performed mechanical testing to evaluate the effects of the process on the burst strength and suture retention strength. It was noted that the vessels had normal consistency and good handling characteristics. The burst strength of the decellularized graft was similar to the fresh vein (2480±460 mm Hg vs. 2380±620 mm Hg (p>0.05)) as well as the suture-holding strength (185±30 gm vs. 178±66 μm (p>0.05)). The functionality was examined by placing decellularized canine jugular veins into a carotid interposition model. Each canine received an autograft and either an allograft or a decellularized allograft on the contralateral side. After two weeks, all grafts were assessed by Duplex imaging to have patency with no significant dilation, rupture or anastomotic false aneurysm.

CryoLife, Inc. (Kennesaw, Ga.) is said to have developed a decellularization process on veins and heart valves called SynerGraft (Hawkins, 2003; Madden, 2002). This process involves cell lysis in hypotonic sterile water, followed by equilibration in a buffer. The tissue is then treated by an enzymatic digestion of the nucleic acids with a combined solution of RNase and DNase. The grafts are then cryopreserved for storage. Results on the CryoValve SG have been said to show approximately 99% reduction in staining of the endothelial cells and interstitial cellular elements (Hawkins, 2003).

In a clinical study by Hawkins, 14 children (8.5±7.9 years) received decellularized, cryopreserved allografts (CryoLife, Inc.), 6 were patch insertions and 8 with valved pulmonary allografts (Hawkins, 2003). These groups were compared to 20 historical control subjects (1.7±2.4 years), 8 with valves and 12 with allograft patch insertions. There was no attempt to match ABO blood types in either group. The effect on the immunogenicity was measured at 1, 3 and 12 months by the frequency of HLA alloantibodies PRA: class I (HLA-A, HLA-B and HLA-C) and class II (HLA-DR/DQ). Antibody levels were slightly higher from preoperative levels for both classes at all time points. The antibody levels were significantly lower in the decellularized allograft group. There was a marked reduction in staining for class I and class II histocompatibility antigens. However, there was no work done in this study to determine whether reduced immunogenicity will truly allow tissue ingrowth and improved long-term durability in patients.

Madden performed a clinical study of 20 patients with an upper extremity SynerGraft cadaver vein allograft for hemodialysis access (Madden, 2002). The first 17 patients were matched (ABO) for blood types while the 3 remaining patients were intentionally given ABO-incompatible SynerGraft allografts. Allosensitization was quantified using the PRA assay (American Society for Histocompatibility and Immunogenetics laboratory protocol) on peripheral blood samples. None of the SynerGraft patients became allosensitized (PRA>10%) at 10 months with a mean PRA of 3.2% (0-7%). All patients in the historic cryopreserved group became allosensitized by 3.1 months with a mean PRA of 84.1%. All three patients with ABO-incompatible SynerGraft allografts showed no allosensitization or acute rejection-type reactions. Typically, removal of viable donor endothelial cells is believed to lead to increased thrombogenicity and decreased infection resistance. There was no significant difference between the groups in the primary, assisted primary or secondary patency rates and no grafts were lost to infection.

Decellularization:

Allograft tissue has an advantage over synthetic implants due to its ability to be innervated by host cells and be fully accepted. The starting material is similar to the native tissue in its structure and function with the geometry and components for cell differentiation. The same is true for xenograft tissue, to a somewhat lesser degree. Allograft or xenograft tissue provide the possibility of autologous cell infiltration creating a biologically active matrix with phenotypically appropriate cells. This allows for reparative and functional characteristics not inherent in synthetic prosthetics. A disadvantage to allograft or xenograft tissue is its biologically active components containing antigens that could lead to sensitization and chronic rejection.

A traditional method for allograft storage utilizes cryopreservation. The intent is to produce a viable construct with minimal antigenicity with optimal biologic functionality and structural integrity. Cryopreservation has been shown to yield improved patency rates over fresh and synthetic grafts in hemodialysis access. The authors of one study believe that it is infection resistant with a large portion of the endothelial cells viable at engraftment (Madden, 2002). At the same time, clinical and experimental data suggest that cryopreservation may be responsible for rendering allografts more brittle and could induce early graft rupture or dilatation. Additionally, the viable cells remaining on the endothelium and within the vascular wall contain the antigens that in this instance may lead to the rejection response seen in allografts.

Acellular Allografts:

The limitations with conventional cryopreserved small-diameter vascular grafts due to immunogenicity and rupture illustrates the need for decellularized vascular grafts. Fixing the tissue with cross-linkers is used to reduce the immunogenicity, but can be toxic or lead to aneurism formation. Decellularization involves the removal of major immunogenic components leaving an acellular scaffold with only insoluble structural proteins, such as collagen and elasin (Hilbert, 2004; Kasimir, 2003).

CryoLife, Inc. (Kennesaw, Ga.) has developed a decellularization process on veins and heart valves called SynerGraft (Hawkins, 2003; Madden, 2002). This process involves cell lysis in hypotonic sterile water, followed by equilibration in a buffer. The tissue is then treated by an enzymatic digestion of nucleic acids with a combined solution of ribonuclease (RNase) and deoxyribonuclease (DNase). The grafts are then cryopreserved for storage. Results on the CryoValve SG showed approximately 99% reduction in staining of the endothelial cells and interstitial cellular elements (Hawkins, 2003).

Maintaining the similarities to the native tissue of the biological composition and geometric design is desirable to promote re-endothelialization and cell migration (Hilbert, 2004; Ketchedjian, 2005; Lu, 2004; Teebken, 2000). The basement membrane on the luminal surface consists of type IV collagen with ligands for firm endothelial cell and myofibroblast attachment and retention (Hilbert, 2004; Schaner, 2004; Wilson, 1995). Preservation of this structure facilitates re-endothelialization to reduce thrombogenicity and promotes migration of myofibroblasts into the vascular wall (Allaire, 1994; Hilbert, 2004; Uchimura, 2003). An insoluble extracellular matrix has been shown to promote fibroblast proliferation and elastin synthesis and organization into fibers (Allaire, 1994). Another study showed the importance of complete cell removal where host myofibroblasts in the media appeared to have been significantly reduced by the presence of collagen bundles and smooth muscle cell remnants that restricted migration (Hilbert, 2004).

One concern is that removal of the viable endothelial cells could result in thrombogenicity and decreased infection resistance. It is believed by some investigators that a lack of surviving cells and endothelial integrity may play a role in graft degeneration and early and late patency (Prager, 2002). Madden showed no significant differences in patency or infection rates when comparing CryoLife's SynerGraft to their own cryopreserved grafts (Madden, 2002). Virtually all cryopreserved homografts are acellular within a year of implantation (though it is believed that this is acellularization prelude to recellularization). It has been shown that after implantation cellular grafts become acellular over time while decellularized grafts have a time-dependent recellularization during the same period (Ketchedjian, 2005). A cellular aortic allograft conduit transplanted into a rat showed a complete loss of smooth muscle cells in the media after 21 days (Grauss, 2003). Inflammation along with the lack cellular function limits tissue ingrowth, performance and reparation. The tissue typically scars and then mineralizes (Grauss, 2003; Ketchedjian, 2005). A cryopreserved allograft pulmonary trunk implanted as a patch was found to become acellular over a 20 week period (Ketchedjian, 2005). A fibrous sheath developed consisting of layers of fibroblasts that line the luminal side and encapsulate the adventitia. This event may represent the same foreign body response seen in surgical implants. At the same time points, the decellularized tissue displayed time-dependent recellularization. Thus, the decellularized scaffold appeared to have an advantage over the cellularized graft with faster repopulation and remodeling due to bypassing the in vivo decellularization step.

With traditionally cryopreserved methods, the endothelial cells slough off and the interstitial cells are removed before the lumen is relined with cells. These series of events could prevent or slow down the remodeling process by exposing the cellularized venous wall, sparking an immune response that proceeds faster than the repopulation of the endothelium. At the same time, transanastomotic endothelialization has been limited in humans despite the success in animal models and is an ongoing challenge in the development of vascular grafts. A four year study in a canine model with iliac and carotid arteries placed in the femoral and carotid positions showed complete endothelialization of the flow surface (Wilson, 1995). The same group with the same model compared arteries to autograft saphenous vein and showed no evidence of endothelialization in the allografts after 6 months while the autografts had substantial endothelial cell coverage. In another study by the same group all grafts retained patency at four weeks (Courtman, 2001). Therefore, results can be variable and unpredictable and appear to be time-dependent. Although, 4 of the 9 decellularized allografts had patency compared to 4 out of 7 cellular autografts. Cell repopulation in humans rarely occurs, but again may be attributed to the presence of necrotic cell debris or even apoptotic cells that block specific cell signals that cause autologous cell repopulation (Ketchedjian, 2005). Other studies have looked at the compressed nature of the media after decellularization with dense collagen and elastin fiber networks reducing the porous network and preventing complete migration passed the intima (Lu, 2004).

Therefore, effective removal of antigens is anticipated to decrease the immunological response, thus, reducing the need for immunosuppressants and favorably impacting the durability of the graft (Bader, 2000; Kasimir, 2003; Ketchedjian, 2005; Uchimura, 2003; Wilson, 1995). Remnants of cells in the arterial or venous wall may promote increased innate and cellular immune responses with inflammation and consequential scarring, contributing to failure of organized migration of phenotypically appropriate cells. Additionally, cell remnants have been attributed to calcification of veins and valves (Courtman, 1994; Hilbert, 2004; Huynh, 1999; Ketchedjian, 2005). A sheep model showed calcification occurred in the classically cryopreserved tissue while decellularized tissue stained negative except around the suture (Ketchedjian, 2005).

Cell Removal Assessment:

The decellularization process in the literature generally follows three main steps, although the specifics of each step vary. The first step in the process is to osmotically lyse the cells contained within the tissue. This has been performed with sterile water, a hypotonic solution or a detergent solution (Conklin, 2002; Hawkins, 2003; Huynh, 1999; Madden, 2002; Schaner, 2004; Sievers, 2003). The cell inactivation is followed by enzymatic digestion of nucleic acids. Some groups use detergents and some prefer biological enzymes with the intention of protecting the matrix for re-endothelialization as well as limited toxicity. Additionally, the methods use mechanical stripping such as shaking. The final cleansing step involves a wash out to remove any residual cellular elements and chemicals. The methods also used multiday processing to achieve greater than 90% decellularization.

The most common detergents used were sodium dodecyl sulfate (SDS), octylphenol ethoxylate (Triton-X 100) and sodium deoxycholate. SDS is a highly ionic detergent with an anionic hydrophobic ligand (Samouillan, 1999). It lyses cell membranes and is believed to be uniform within all layers of vascular tissue (Schaner, 2004). It only requires a low concentration to remove endothelial cells, but removal of smooth muscle cells is dose-dependent. It is an amphipatic molecule that associates with proteins via its hydrophobic domain, leaving the hydrophilic region exposed. This possibly creates an altered internal charge state that leads to swelling of tissue by increased water binding. Collagen has more hydrophilic sites than elastin, thus has an affinity for water. Decreased thermal stability of collagen is due to the disruption of hydrogen bonding (Courtman, 1994; Samouillan, 1999).

Krasovakaya showed the hydrolysis of elastin with pancreatic elastase was markedly accelerated if pretreated with SDS (Courtman, 1994). Due to the elastin being predominantly hydrophobic, SDS reduces its hydrophobicity, thus exposing it to an aqueous environment and making it more susceptible to elastases (Courtman, 1994; Samouillan, 1999). Additionally, SDS is difficult to rinse from the fibers, so it could alter the mechanical properties by binding to the polypeptide chains within the fibers or binding into the interfiber spaces of the outer surfaces of the fibers (Samouillan, 1999).

Residual amounts of SDS in the tissue can also be toxic to cell seeding in vivo and in vitro. Investigators have shown that porcine aortic roots treated with SDS were surrounded by nonviable endothelial cell fragments that were seeded onto the matrix (Rieder, 2004). Within 24 hours of incubation there was extensive cell lysis with patchy cell distribution. SDS has been shown to be effective in cell removal, but can cause detrimental structural changes (Courtman, 1994; Kasimir, 2003). Courtman abandoned further use of SDS after witnessing a significant drop in the shrinkage temperature of bovine pericardium, as well as a three-fold increase in tissue thickness likely due to swelling (Courtman, 1994). A study with pulmonary porcine valve conduits decellularized in 0.1% SDS showed complete decellularization but at the cost of a significantly disintegrated matrix at as early as 24 hours incubation time (Kasimir, 2003). Thermogravimetric analysis (TGA) and differential scanning calorimetry (DSC) was used by Samouillan to analyze the effects of detergents on the extracellular matrix of pulmonary aortic roots. They found that SDS had a destructive effect with destabilizing the collagen triple helix and swelling of the elastin network (Samouillan, 1999). Schaner, on the other hand, showed no significant alterations with their decellularization method (Schaner 2004). These authors studied the composition and strength of a decellularized human greater saphenous vein specimen to determine its potential as a vascular tissue-engineering scaffold. Transmural cell removal was found to be nearly complete (>94%) at a concentration of 0.075% SDS. The luminal surface was completely devoid of endothelial cells at all concentrations tested, but the cell removal in the vascular wall appeared to be concentration-dependent. Histology showed the collagen morphology was similar, the basement membrane was intact and the elastin staining only decreased slightly. To assess the effects on the structure of the vein, this group performed mechanical testing. The burst strength of the decellularized graft was similar to the fresh vein (2480±460 mm Hg vs. 2380±620 mm Hg) as well as the suture-holding strength (185±30 gm vs. 178±66 gm). The decellularized vessels were placed as carotid interposition grafts and assessed by Duplex imaging after two weeks. All grafts had patency with no significant dilatation or rupture. No work was done to look at the inflammatory reaction or the recellularization of the grafts.

Nonionic detergents have been found, in most cases, to be effective in cell removal while maintaining the extracellular matrix (Kasimir, 2003). Triton-X 100 is an excellent detergent and emulsifying agent that has an effective performance across broad temperature ranges, is soluble in water and biodegradable (Surfactants). Additionally, it is compatible with anionic, cationic and other nonionic surfactants which makes if favorable to combine with other agents for a synergistic effect. Courtman chose 1% Triton-X 100 to decellularize canine iliac and carotid arteries to be used in femoral interposition bypass grafting (Courtman, 2001). After four weeks, angiogram showed that all grafts had patency. Further analysis showed no thrombus formation and no aneurism formation. There was no evidence of inflammatory cells except in small areas at the anastomoses. There were some cells on the lumen consistent with endothelial cells and some mesenchymal cells in the adventitia, but the media was completely acellular. There was a pannus ingrowth of smooth muscle cell at each anastomosis. Triton-X 100 showed no change in cellularity in a rat AVA at 1% and little change at 5% for 24 hours (Grauss, 2003). Samouillan also looked at the effects of Triton on the extracellular matrix with TGA and DSC and they found it had no effect on the structural integrity and the collagen helix remained stable (Samouillan. 1999). Cho achieved complete cell removal with 0.5% Triton and successful seeding of bone-marrow derived cells resulting in the typical cobblestone morphology visible in scanning electron microscopy (Cho, 2005). This was confirmed with van Wildebrand factor and CD31 staining, which are phenotypic markers for mature endothelial cells.

Triton was combined in several studies with sodium deoxycholate, resulting in complete decellularization with preservation of the matrix (Kasimir, 2003). Kasimir found that pulmonary valve conduits could become completely acellular incubated for 24 hours at concentrations as low as 0.25%. Kasimir added EDTA to the solution, which may have improved cell removal. The matrix appeared well preserved with minimal structural alterations. Reider, a co-author with Kasimir's study, found incomplete removal of porcine aortic roots and pulmonary roots at the same conditions but employed intensive washing to remove the residual chemicals (Rieder, 2004). When this group seeded the matrix, it found that the treatment enabled host recellularization with a confluent layer of endothelial cells on the lumen surface. This was an improvement to their cell seeding on the grafts decellularized with SDS (Rieder, 2004).

Detergent residuals can be cytotoxic and inhibit cell adhesion, migration and proliferation (Ketchedjian, 2005; Uchimura, 2003). SDS and Triton have been shown to be difficult to remove even after extensive washing. Regarding the toxicity issue, biological enzymes have been investigated. Trypsin is a natural enzyme with limited toxicity, but has been found to only achieve partial decellularization and produce severe structural alterations (Bader, 2000; Kasimir, 2003). Although, other authors have shown preservation of the matrix in human and porcine aortic tissue with Trypsin decellularization (Bader, 2000; Kasimir, 2003; Teebken, 2000). It has typically been enhanced with EDTA to chelate Ca2+ thus increasing the efficiency of Trypsin. Teebken developed an acellular vascular xenograft matrix from porcine thoracic aortas for the purpose of seeding them with human endothelial cells (Teebken, 2000). Little evidence has been given to correlate results from the seeding in vitro and in vivo repopulation. This group used 0.1% Trypsin plus EDTA followed by additional biological enzymes, ribonuclease (RNase) and deoxyribonuclease (DNase). The idea is that these enzymes are capable of removing cell components as well as cellular antigens, lipids, and to some extent glycosaminoglycans with limited toxicity. After two 24 hour extractions at 37° C. in Trypsin and EDTA interrupted by incubation with RNase and DNase, light microscopy showed no cell nuclei or intracellular components in cross-sections of the aortic wall. Immunohistochemical stains for fibroblasts (α-actin) and endothelial cells (factor VIII-related antigen, CD31) were negative and the matrix appeared well preserved. No mechanical testing or quantitative matrix analysis was performed.

A study with allogeneic valve grafts decellularized with 0.05% Trypsin for 0.5 to 1.5 hrs showed complete loss of cells except in the media (Grauss, 2003). When followed by Triton for a 24 hour incubation period, the entire matrix was acellular. In both groups, severe damage to the leaflets was noted with histology. Another study using porcine aortas with 0.1% Trypsin for 24, 48, 72 or 96 hours contrasts these findings (Bader, 2000). This group found that cell removal was time-dependent with a majority of the cells removed at 48 hours with only minimal damage with an increasing microporous structure, as assessed by SEM. Reider found incomplete cell removal of porcine aortic roots at the same concentration of Trypsin combined with EDTA with a 48 hour incubation time (Rieder, 2004). In vitro cell seeding revealed cobblestone morphology on the luminal surface, indicating a confluent endothelial cell layer while cells in the media attached in a patchy distribution and starting to synthesize collagen.

Biological Assessment:

Rat aortas have been grafted as autografts, decellularized autografts, allografts or decellularized allografts with an SDS protocol (Allaire, 1994). After two months, the grafts were explanted and examined for structural and cellular changes. All autografts retained patency while 3 of the 13 allografts thrombosed (78% patency). The untreated autograft showed an intact media with no intimal thickening but was surrounded by thick adventitial fibrosis. The decellularized autograft produced a compacted acellular media. The external elastic lamina was thinner and adventitial fibrosis was visible. Intimal thickening did occur but did not contain inflammatory cells. The lumen was covered with endothelial cells. Unlike the autograft, the intima contains cells that stained positive for α-actin. Cellular and fibrillar elements were equally distributed over the length of the graft.

The decellularization of the allograft material did prevent dilation from occurring and the vessel appeared macroscopically similar to the untreated autografts. The untreated allografts were slightly dilated throughout the length compared to the autografts. There was reduced adventitial inflammatory infiltration and the elastin was preserved. Just as with the treated autograft, the treated allograft had a compacted acellular media. Although, it was noninflammatory and significantly thinner and richer in elastin than the untreated allografts. The internal elastic lamina was approximately 90% preserved along the length but the external elastic lamina was thinner and embedded in adventitial fibrosis. The intima of the treated allograft showed thickening with no inflammatory cells and a higher smooth muscle cell and collagen density than untreated allografts. The lumen was covered with endothelial cells with equal distribution of the extracellular matrix.

The media of the untreated allografts was dislocated and significantly thinner with fewer smooth muscle cells and less elastin. It contained inflammatory infiltrates. The internal elastic lamina was fragmented over more than half of its length and the interlamellar fibers were disrupted. There was intimal thickening containing inflammatory cells and lymphocytes with leukocytes adhering to the endothelium. The adventitia contained large cellular and fibrous inflammatory cells.

Wilson used a multistep detergent-enzymatic extraction process with hypotonic and hypertonic solutions on canine iliac and carotid arteries (Wilson, 1995). These grafts were implanted into the carotid and femoral arteries of dogs, foregoing anticoagulant and antiplatelet therapy. After four years, they found no aneurism formation, no calcification, an intact elastin network and no degradation of the collagen in the wall. The luminal surface was completely endothelialized and there was no evidence of chronic rejection. The cumulative patency rate was 95% compared to 100% occlusion in three months with synthetic material. In a follow up study, this group compared autograft canine saphenous veins to decellularized allograft canine carotid arteries for a CABG model. After 6 months, 4 out of 7 saphenous vein grafts had wide patency with the remaining three occluded at the 2 week angiogram. The grafts having patency showed substantial endothelial cell coverage on the lumen. For the allografts, 4 of 9 had wide patency with the remaining 5 thrombosed by the first 2 weeks. There was no inflammation, but minimal cell repopulation and no evidence of endothelialization except near the anastomoses. The same group at the University of Toronto used canine iliac and carotid arteries for femoral interposition bypass grafts (Courtman, 2001). At 4 weeks, the grafts had wide patency with some cells on the lumen consistent with endothelial cells. The media was found to be acellular.

A study using allograft pulmonary artery for a patch reconstruction to repair great vessels in sheep also compared cryopreserved allograft and cryopreserved decellularized allografts as well as fresh decellularized allografts (Ketchedjian, 2005). After 20 weeks, all patches incorporated into the great vessel repairs without aneurism formations or infection. There was no statistical difference in the explant and implant dimensional ratios. The cryopreserved allografts became acellular over time and developed a fibrous sheath consisting of layers of fibroblast cells that line the luminal side and encapsulating the adventitia. This is similar to the foreign body response seen in surgical implants. The decellularized tissue showed time-dependent recellularization at 10 weeks and 20 weeks. There was partial endothelialization along the lumen and cells infiltrating the elastin bands within the wall.

Staining for α-actin indicated that most of the infiltrating cells were biologically active myofibroblasts. The cryopreserved grafts were positive for calcification while none was evident in the decellularized tissue.

Grauss compared cellular and acellular valve grafts in the descending aorta of a rat for 21 days (Grauss, 2003). All cellularized explants showed leaflet deformation with a considerable decrease in collagen and a slight decrease in elastin. There was a complete loss of smooth muscle cells in the media of the aortic root accompanied by multifocal disruption of elastin fibers. On the other hand, all of the decellularized explants showed leaflet preservation with elastic fibers in the media normally arranged and similar collagen content when compared to the nontransplanted tissue. The media of the acellular allograft was also void of smooth muscle cells.

Hilbert evaluated the morphologic characteristics in a small-diameter freeze-dried decellularized carotid artery of a goat treated with a nonionic detergent solution (Hilbert, 2004). This solution contained inhibitors, such as proteoase, reactive oxygen species and other free radicals. Histological analysis showed complete endothelial removal while preserving the basement membrane. Additionally, no cells were seen in the intima, media or adventitia. Although, there were remnants of smooth muscle cells in the media without nuclei. The extracellular matrix seemed well preserved, but oval to circular spaces were occasionally noted in the media. The internal elastic lamina remained intact, as well as layered elastic laminae in the media.

This group evaluated these decellularized freeze-dried grafts as a carotid interposition graft in goats for 6 to 7 months and compared them to autologous cephalic vein grafts. All grafts had patency upon explantation, and no significant dimensional changes or aneurism formations were noted in the allografts. There was marked variability in the thickness of the neointima within as well as between the allografts. There was also great variation along the length of the autografts. Although, the neointimal thickness of the allografts were comparatively thin at 133±234 µm (1 to 640 µm) compared to a thickness of 249±224 µm (8 to 800 µm) for the autografts. The autografts showed a luminal surface lined with a layer of endothelial cells while the allograft showed a discontinuous layer. Even in these regions of incomplete endothelialization, thrombi were not observed. Both types of grafts showed myofibroblasts, collagen and proteoglycans.

Upon explantation, the allograft appeared relatively acellular in the media. Among the dense collagen and elastic lamellae, there were focal cellular regions containing myofibroblasts of the host. The authors believe that the number of host myofibroblasts in the media may have been significantly limited by the presence of dense collagen bundles and smooth muscle cell remnants. Host cell migration was most apparent close to the anastomoses and was rich in proteoglycans. The variable regions of host cell migration from the neointima in to the media appeared to occur through fenestrations in the internal elastic lamina. Most cell migration appeared to occur in the adventitia along the length of the grafts. The adventitia looked healed and repopulated by connective tissue cells. Histologically, there was no evidence of calcification and inflammatory cells were not present in the graft wall. Electron microscopy showed calcification of minute remnants of cell membranes. Ingrowth of host blood vessels was not observed.

Conklin investigated a small-caliber xenograft with a porcine common carotid artery model (Conklin, 2002). This group followed cell lysis with multiple enzymatic digestions and detergent washes while agitating. Histology and electron microscopy showed complete removal of cellular components while the extracellular matrix appears to remain intact. H&E stain showed no signs of remaining nuclear material in the walls of the vessels and TEM showed complete removal of cellular material from the medial layers. Histology showed an intake internal elastic lamina along with elastin lamellae in the media. TEM showed the basic extracellular microstructure remained intact after processing.

In addition to reducing immune reactions and decreasing thrombogenicity of the luminal surface by decellularization, this group wanted to ensure that the process would maintain a graft with similar mechanical properties to the native vessel, high strength and good handling characteristics. They investigated the compliance and burst strength of the vessels on a custom-built system that measures the diameter changes while increasing the intraluminal pressure. The compliance is expressed as the percentage diameter change per mm Hg change in pressure normalized to the compliance of fresh vessels. The average compliance was calculated as the slope of the linear regression line in the physiological pressure range (70-130 mm Hg).

The mechanical analysis was performed on decellularized vessels, decellularized and heparin-treated vessels, fresh vessels, alcohol preserved vessels, and ePTFE prosthetic grafts. The ePTFE grafts were the least compliant (0.025% and the decellularized grafts were slightly more compliant (0.182%) than the fresh vessels (0.172%). Alcohol caused the tissue to stiffen some (0.160%) while the heparin treatment produced a much stiffer graft (0.0975%). During the burst testing, none of the fresh vessels burst within the limit of the pressure transducer (2300 mm Hg). One out of four of the decellularized vessels burst within the limit at 1654 mm Hg. Although there may be some strength loss measured in that one vessel, there still is a high safety of margin over ten times the physiological pressure. Only four samples were tested in this group. Additionally, there was no difference found in the average suture retention strength between the fresh and the alcohol and heparin treated specimens. This only gives pre-implantation mechanical result with evidence of some effect. Once implanted and the cellular and remodeling response occurs, there could be an exaggerated effect on the samples that may cause minute damage in the vascular wall.

This group examined their decellularized process with heparin cross-linking on a carotid artery bypass in dogs. Two animals each were euthanized at 24 and 67 days and the explants were prepared similarly for histology and stained with H&E or immunohistochemically for α-actin or Factor VIII. At 24 days, fibroblast-like cells appeared to densely populate the media and there were few endothelial-like cells lining the lumen. After two months, the dense α-actin staining suggested smooth muscle cells densely populated the vessel wall and Factor VIII staining confirmed that endothelial cells lined the lumen.

In a clinical study by Hawkins, 14 children (8.5±7.9 years) received decellularized, cryopreserved allografts, 6 were patch insertions and 8 with valved pulmonary allografts (Hawkins, 2003). These groups were compared to 20 historical control subjects (1.7±2.4 years), 8 with valved and 12 with allograft patch insertions. There was no attempt to match ABO blood types in either group. The effect on the immunogenicity was measured at 1, 3 and 12 months by frequency of panel-reactive HLA alloantibodies (PRA): class I (HLA-A, HLA-B, and HLA-C) and class II (HLA-DR/DQ). A flow cytometry technique was used to calculate the percentage of fluorescent positive beads, indicative of the percentage of PRA. Antibody levels were significantly higher from the percentage levels for both classes at all time points. The antibody levels were significantly lower in the decellularized allograft. There was a marked reduction in staining for class I and class II histocompatibility antigens. However, there was no work done in this study to determine whether reduced immunogenicity will truly allow tissue ingrowth and improved long-term durability in patients.

Thus, in view of all of the above, there is a long felt need for an effective vascular graft decellularization process. The present invention provides a process which is effective for decellularization of a vascular tissue with maintenance of matrix integrity. In a non-limiting example of this technology, allograft tissue is treated with different cleaning agents (e.g. detergents, enzymes, and/or chelators) at various temperatures for specified times. The level of decellularization is examined histologically and the amount of antigenicity is determined immunohistochemically. The matrix integrity is assessed with an enzyme digestion assay for collagen. This allowed for development of parameters that produce efficient cell and cellular debris removal without damaging the insoluble scaffold.

Although certain cleaning agents are described above, other agents can be used in the process of the present invention. These include, but are not limited to the following, enzymes (such as serine proteases), alcohols, oxidizing agents, and detergents such as cholate, alcohol ethoxylates, alkylphenol ethoxylates, alkyl polyglycosides, polyoxyethylene ethers, polyoxyethylene sorbitans, any of the Triton, Tween or Brij series of detergents, alkyl benzenesulfonates, alkyl sulfonates, alkyl phosphates, and alkyl sulfates; or salts or mixtures thereof. Cholate (sodium deoxycholate) and Triton X-100 are presently preferred as detergents. Various cell lysing agents may be useful as cleaning agents. Phosphate buffered saline (PBS) can also be used for debris removal (rinsing agent).

Biological enzyme cleaning agents include, but are not limited to, trypsin, ribonuclease (RNase), deoxyribonuclease (DNase), papain, collagenase, caseanase, and other proteolytic enzymes.

Furthermore, additional agents that aid in processing may be used in combination with any of the agents described above. These include chelating agents such as EDTA and agents that increase patency such as L-arginine. EDTA increases efficiency of the process by chelating ions and L-arginine is involved in the process of producing NO which assists in keeping the vessel patent by reacting with the smooth muscle cells.

See Example 1 which illustrates a non-limiting example of this technology.

It is a further aspect of the present technology to utilize a two or more step process with the same or different cleaning agents or additional agents. This two or more step process may be referred to as a recipe.

See Examples 4 and 5 which illustrate non-limiting examples of this technology.

Sterilization:

A common disinfection method for allograft or xenograft tissue is an antimicrobial soak in which the tissue is aseptically processed with a cocktail of antimicrobial agents and sometimes antifungal agents. However, tissue treated as such may still harbor harmful organisms. Additionally, some methods for testing sterility on thus-treated tissue may be unreliable (Waterworth, 1974). Specifically, residual antibiotics from the treatment process have been shown to inhibit growth in post-treatment surveillance cultures, producing false-negative results leading to cases of septic arthritis, hepatitis C transmission, *Streptococcus pyogenes* (GAS), and *Clostridium* spp (Hepatitis, 2003). Of note, cases of soft tissue allograft-associated disease transmission by spore-forming organisms that are resistant to antimicrobial solutions have been reported within the last few years (Hepatitis, 2003). Vascular tissue is vulnerable to organisms (including fungi and viruses) inherent in the donor or transmitted during procurement or processing. Such organisms may be resistant to the antimicrobials used for allograft disinfection (Clark, 1998; Reller, 1975; Silver, 1971).

Graft-associated infections can result from an unpredictable source of pathogens. This can make it difficult (but not impossible) to validate a sterilization process. One way to overcome this difficulty is to use a representative bacterium that is more difficult to kill than anything that will be detected on the tissue. The bacterium *Bacillus stearothermophilus* is a spore forming microbe that is resistant to a wide range of temperatures and processing conditions. If a sterilization process provides a 6 log reduction in this spore, this would strongly indicate that the process provides protection against the bacteria typically found on contaminated vascular tissue.

Disinfection and Sterilization Processes:

It is estimated that 60% of all human infections are caused by viruses (Center). Viruses are composed of DNA and RNA, lipids, and a protein membrane for protection. Their physical characteristics are classified as either lipophilic or hydrophilic. Lipophilic viruses have a lipid shell known as an envelope. These viruses are easier to inactivate with removal of the envelope via a disinfectant. Such viruses include HIV, RSV and hepatitis B (HBV). Hydrophilic viruses are known as nonenveloped viruses since they do not have a shell. Instead, they have a very tough protein coat that is difficult for some disinfectants to enter. Such viruses include poliovirus, rhinovirus and hepatitis A (HAV).

Transmission of viruses through blood and blood products has led to efforts in inactivation and removal of endogenous materials and possible contaminants. The most widely used methods are pasteurization, chemical inactivation, irradiation and solvent extraction of lipids. Pasteurization involves destroying or retarding the growth of bacteria without destroying biological activity of the sample by heating to a moderate degree (60° C.-70° C.) for a substantial period of time rather than boiling (Dox, 1993). This process is used to disinfect blood products such as Alpha-1 proteinase inhibitor concentrates from pooled human plasma (Mitra, 1988). Injected samples were maintained at 60° C. for 10 hours and then tested for viral inactivation. The thermolabile viruses, vesicular stomatitis virus, herpes simplex virus-1, visna, and HIV, were inactivated within 1 hour while poliovirus took almost 5 hours. Porcine parvovirus, one of the most thermostable viruses known, was reduced by 3 logs but there was still a 1.7 log infectivity remaining after 10 hours. Clinical data 6 months post-infusion were all negative for hepatitis B (HBV), non-A non-B hepatitis, and HIV.

Solvents and detergents alone or in combination are more effective than pasteurization, with success in disrupting enveloped viruses but nonenveloped viruses are unaffected (Horowitz, 1995). Triton-X 100 used with the organic solvent tri(n-butyl)phosphate (TNBP) was shown to inactivate very large quantities of HBV, BCV and HIV in pooled plasma (Horowitz, 1995; Horowitz, 1992). The samples were incubated for 4 hours at 30° C. in 1% TNBP and 1% Triton-X 100. This process achieved a greater than 6 log reduction in HBV and HIV and a greater than 5 log reduction in HCV. These results were tested in vitro by injecting chimpanzees with the plasma concentrates, and the animals were negative for HBV and HIV.

Alcohols are known effective antiseptic agents used for hand sanitation and thermolabile instrument disinfection (70%) in hospitals worldwide (Block, 2001; van Bueren, 1994). The most widely used alcohol is isopropyl alcohol. In dilutions of 60% to 95% it kills bacteria, mycobacteria, fungi and large or lipid-containing viruses (Block, 2001). However, it is not as effective on hydrophilic viruses. Ethyl alcohol is often used to inactivate hydrophilic viruses. A study compared the effectiveness of 70% alcohol in inactivation of HIV dried on a surface or in suspension (van Bueren, 1994). The remaining 5.5 log titre after drying was completely inactivated within 1 min. This time was affected by an increase of 100% in protein load increasing the inactivation to 4 to 10 min, providing a significant barrier to dried viruses. Alternatively, the high titres of HIV in suspension were rapidly inactivated independent of protein load.

Of all microorganisms, spores are the most resistant to antimicrobial treatment. Spores are small, single-celled reproductive bodies that are highly resistant to heat and are capable of growing into a new organism. Bacteria form spores and this dormant phase is a response to adverse environments as a means of protection. Recently, more attention has been placed on the need to inactivate spore forming bacteria since cross-infection by *Clostridium* spp. (a species found in intestinal contents) has been reported on various soft tissue grafts that has resulted in graft removal or even death (Control, 2002; Huang, 2004).

Oxidative processes involve electrons from a reducing agent (Oxygen) being transferred to the oxidizing agent. This process is used in sterilizing equipment with compounds such as hydrogen peroxide, peracetic acid, peroxysulphates, chlorine dioxide and ozone. Hydrogen peroxide at a concentration of 3% is used as an antiseptic agent and combined with ultraviolet light to disinfect cartons for food products. Its sporicidal activity at higher concentrations has been investigated for medical and dental instruments (Acosta-Gio, 2005). In that study, suspensions of 106 *Bacillus atrophaeus* spores were maintained at room temperature in 7.5% hydrogen peroxide. No growth was detected after a 6 hour incubation period.

Peracetic acid (PAA—CH3C(O)OOH) is an organic oxidant that is highly effective against a wide variety of bacteria, fungi, viruses and spores (Hodde, 2002; Huang, 2004). It has been shown to be an effective antiviral agent for both enveloped and nonenveloped viruses at 0.2 to 0.35%. This chemical rapidly penetrates the microorganisms and interactions result in the release of oxygen free radicals causing the destruction of enzymes (Hodde, 2002; Koivunen, 2005). It has been used for sterilization of bone, heart valves and small intestine without significant adverse effects on the morphology and structure (Hodde, 2002; Huang, 2004). Another advantage is its low toxicity since its residues, oxygen, carbon dioxide and water, are natural and harmless.

PAA combined with ethanol was examined for its effectiveness in inactivating a wide range of microorganisms in allogeneic bone tissue (Pruss, 2001; Pruss, 2003). In one study, nonviable organisms were detected after 2 and 4 hours incubation periods. There was a greater than 5 log reduction in *Staphylococcus aureus, E. faecium, Pseudomonas aeruginosa, B. subitilis, Clostridium sporogenes, Mycobacterium terrae*, and *C. albicans* (Pruss, 2001). The same group tested treatment of bone spongiosa cubes injected with three enveloped and three nonenveloped viruses and then treated with PAA with ethanol (Pruss, 2003). There was more than a 4 log reduction in all viruses except in one of the nonenveloped viruses, HAV. A greater than 7 log reduction was achieved in HAV after implementing a delipidating step.

A porcine-derived scaffold made out of small intestine submucosa (SIS) was treated at room temperature for 5 min to 2 hours with a PAA/ethanol (0.18% in 4.8% mixture) solution to inactivate viruses endogenous to porcine (Hodde, 2002). Relevant enveloped, nonenveloped and model viruses represented different virus families. Enveloped viruses were inactivated more easily with all viruses inactivated within 30 min. In a later study, this group examined the retention of endothelial cells seeded onto the matrix after sterilizing with the PAA/ethanol (0.1%) solution (Hodde, 2002). The proteins present on the matrix that may contribute to site-specific remodeling are type I collagen, type IV collagen and fibronectin (FN). These proteins were well preserved and, therefore, retained their ability to bind cells.

Peracetic acid was compared directly to hydrogen peroxide in a wastewater medium (Koivunen, 2005). PAA has shown good disinfection against enteric bacteria in wastewaters, but viruses and bacterial spores are more resistant. On the other hand, hydrogen peroxide is not typically used alone due to its slow disinfection action and low efficiency. Wastewater-like test medium containing *E. coli, Enterococcus faecalis* or *Salmonella enteritidis* were treated for 10 min in PAA or hydrogen peroxide. PAA dose of 0.3% achieved a 2 to 3 log reduction in enteric bacteria while peroxide doses of 0.3 to 15% achieved below 0.2 log microbial reductions. *Enterococcus faecalis* is one of the organisms recommended for validation of a tissue disinfection process. The higher reactivity of PAA compared to hydrogen peroxide may be due to its ability to better penetrate the cell membrane causing disruption as well as blockage of enzymes and transport systems in microorganisms. Also, hydrogen peroxide may be less effective due to its purity. It is highly reactive due to hydroxyl radicals produced when ferrous iron ($Fe^{2+}$) is added to the solution (Harbor-Weiss/Fenton reaction) (Reinhart, 2004). Additionally, some organisms may be protected against hydrogen peroxide due to catalase enzyme presence. The effectiveness of these oxidants in killing spores has to be balanced by their effect in damaging the tissue matrix. Collagen is the only protein susceptible to fragmentation by hydroxyl radicals.

Huang et al. studied the sterilization of human donor skin with PAA (Huang, 2004). They immersed skin in 0.1% PAA for 3 hours at room temperature under constant agitation. The samples retained their dermal structure and components of the basement membrane. The collagen fibers maintained their normal architecture with fine and wavy elastin fibers located among them in a normal pattern post implantation. The extracellular components were only analyzed qualitatively using histology and degradation was not assessed which can give an indication to the remodeling response. Human bone-patellar tendon-bone (BPTB grafts were treated in a similar mixture at room temperature under low pressure for 4 hours (Scheffler, 2005). The tendons were mechanically tested with no significant difference found in the viscoelastic properties, stiffness or maximum loading properties when compared to untreated controls. Again, no conclusions can be drawn about biological healing or remodeling.

Processing and Determination of Survivors:

Sterilants can fully kill or remove bacteria and viruses to specified sterility levels under appropriate conditions. According to the FDA Guidance document for the use of liquid germicides, sterilization is associated with total absence of viable organisms (Guidance, 1996), though sterilization is used herein to indicate the absence of viable organisms detected using currently available detection technology. Sterilization can be shown by testing which involves challenging a sample graft with a known amount of bacteria or other biological indicator and then determining the log reduction achieved by the sterilization process. In this regard, the log reduction values are frequently used as measures of the effectiveness of the sterilization process being tested. The absence of the biological indicator after the process indicates a sterilized graft has been produced. The first step in evaluating a sterilization process is the selection of an appropriate microorganism(s) as a biological indicator. *Bacillus stearothermophilus* is a species of gram-positive bacteria found in soil, hot springs and spoiled food products. It is not a common contaminate of tissue products, but it is used as an indicator in instrument sterilization equipment since it is the spore which is hardest to kill (at least which is presently known), as it is highly resistant to high temperatures.

The effectiveness of a sterilant is defined in terms of decimal reduction time (D-value). This is the exposure time (t) used under certain conditions to cause one log reduction (n) (90%) of the initial population. A suspension is expected to follow a predictable death rate regarding a plot of the amount of survivors over time. The negative reciprocal of the slope of regression lines of survivor curves gives the D-value where $$t = D \times n$$

$$n = \log(N_o - N_f)$$

A study using *B. stearothermophilus* as one of its biological indicator for PAA and hydrogen peroxide calculated the D-values of vegetative and spore forming bacteria (Mazzola, 2003). PAA was represented by a 1% solution of commercially available Minncare® (0.45% PAA+2.2% hydrogen peroxide, pH 2.3). An initial spore population of 104 to 105 CFU/ml (colony forming units) was placed in either Minncare or 1.5% to 26.5% hydrogen peroxide at 25° C. and removed at regular intervals. For vegetative bacteria samples were removed every minute while samples were removed every 5 minutes for spore forming bacteria. The survivors were analyzed on tryptic soy agar (TSA) pour plates at various dilutions.

The most resistant bacteria against Minncare were *B. stearothermophilus, B. subtilis* and *E. coli* with D-values 2 to 3 times higher than the more sensitive *A. calcoaceticus, E. cloacae* and *S. aureus*. The presence of PAA in Minncare reduced the D-value of *B. subtilis* by a factor of 10 compared to hydrogen peroxide alone (5.9 min vs. 55.2 min). D-value for *B. stearothermophilus* was 4.7 min after being treated at a much higher concentration of hydrogen peroxide (26.5%).

Suitable oxidizing sterilants for use in the present processes include, but are not limited to, peroxides, oxides, hypochlorites, ozone, and percarboxylic acids; or mixtures thereof. Furthermore, percarboxylic include peracetic acid, perpropionic acid, perbutyric acid, peroctanoic acid, perglycolic acid, perglutaric acid, persuccinic acid, perlactic acid, percitric acid and perdecanoic acid; or mixtures thereof. Peracetic acid (PAA) is presently preferred.

Alcohols may also be used as sterilants, including ethanol, propanol (including isopropanol), and butanol (including isobutanol and tert-butyl alcohol). The alcohol may be provided in a solution or mixture.

Agents that enhance the action of the sterilants can also be used. A non-limiting example of these is the use of iron with peroxide. Example 2 is a non-limiting example of this technology.

It is a further aspect of the present technology to utilize a two or more step process with the same or different sterilants or additional agents. This two or more step process may be referred to as a recipe.

See Examples 4 and 5 which illustrate non-limiting examples of this technology.

Combination of Sterilization and Decellularization:

A preferred embodiment of the present invention combines sterilization and decellularization to achieve both effective removal of the cells contained within a vascular tissue matrix and an effective reduction in potential harmful organisms to create grafts suitable for human implantation. As a non-limiting example, human saphenous vein samples are introduced to a sequence of chemicals in a two or more step process with optional mechanical stimulation to provide effective sterilization and decellularization of the tissue. Autograft or xenograft tissue can also be thus treated.

This two or more step process may be referred to as a recipe. The present techniques include using a recipe for the treatment of vascular tissue. Non-limiting examples of recipes were tested in the rat study described in Example 4. These include combinations of two cleaning agents (e.g., sample C), a sample including a cleaning agent, plus further treatments (e.g., sample D) and a recipe including sterilants and cleaning agents (so-called "Prototype recipe": sample G). An exemplary recipe is as follows: 1% Triton 40° C. 20 min; 6% HP (hydrogen peroxide) 40° C. 20 min; 0.25% Cholate/1% Triton 40° C. 2 hrs; 0.1% PAA 40° C. 1 hr; PBS 40° C. 10 min (5×'s rinsing). PBS rinses also occur between each chemical step. The processing was performed in sterile chemicals in tubes on a shaker in an incubator.

It is also within the scope of the present invention to include the use of fixing (cross-linking) agents such as glutaraldehyde in a recipe (see, e.g., sample D in Example 4). Current use of glutaraldehyde is mainly at high concentrations which lead to calcification. When glutaraldehyde is to be used in the present processes, it is preferred that the tissue is essentially decellularized before treatment with glutaraldehyde. A low level of glutaraldehyde (about 0.001% to 0.005%, preferably about 0.0025%) is then used to prevent immune assault that may occur due to low levels of residual cellular debris. A DNA assay can be used to determine whether there is residual DNA after the decellularization process. If glutaraldehyde is used, it is also within the scope of the present invention to couple this with the use of L-arginine. Adding an L-arginine treatment step has two purposes: (1) it is used to neutralize residual glutaraldehyde that was not utilized in cross linking; and (2) it is involved in the process of producing NO which assists in keeping the vessel patent by reacting with the smooth muscle cells.

Further studies (see Example 5) have demonstrated improved results in recipes that have PAA preceding Triton as well as using pressure-induced processing and optionally sonication. Thus, it is also within the scope of the present invention to include the use of oxidizing sterilants before cleaning agents in a recipe. It is additionally within the scope of the invention to use pressure-induced processing and optionally sonication during the course of a recipe.

Specifically, a process for making a vascular graft more suitable for implantation into a recipient is as follows:

(a) contacting a vascular graft with an oxidizing sterilant; and (b) contacting the vascular graft with a cleaning solution;

wherein the contacting steps are at a temperature less than about 45° C. and for a total contact time less than about 8 hours. Preferably, step (a) occurs before step (b).

See Examples 4 and 5 which illustrate non-limiting examples of this technology.

Pressure-Induced Increase in Pore Volume (Pressure-Induced Processing):

Common problems with decellularization methods are the inability to achieve complete removal of cells and cellular debris as well as extensive processing times needed to achieve high levels of decellularization. Without complete removal of cells within the vein wall, an immune response is elicited and in some cases led to evidence of calcification or inhibition of cell migration (Castier, 1999; Conte, 1998; Prager, 2002). Additionally, it is difficult to remove the chemicals that are embedded within the matrix, and embedded chemicals can have a toxic effect leading to cell death and prevention of cell migration once implanted (Hilbert, 2004). Current processing times range from 24 hours to several days under physiological temperatures and continuous agitation.

The present inventors have discovered that a more efficient method to perfuse the venous wall (with optional combination of other treatment steps) allows for shorter treatment times while maintaining physiological temperatures. Additionally, it was discovered that lower processing temperatures can be used when pore volumes are increased.

Numerical models have been used to study the in vivo transport of water and macromolecules in arterial walls under physiological conditions. These methods are used to understand the migration of particles, such as lipoproteins, that occur in atherosclerosis as a function of transmural pressure gradients. Macromolecule transport through healthy and leaky clefts is believed to lead to intimal hyperplasia. As pressure is applied during blood flow, there is a volume and particle flux that is assisted by a stretch of the extracellular matrix. Using these concepts, the effect of applied pressure to the lumen on the transport of a surfactant through the vein was investigated in the process of achieving a more efficient, but also gentler, process for removing cellular material from allograft or xenograft tissue. By pressure-induced stretching and pressure-induced convection, decellularization agents more efficiently penetrate the venous wall to remove endogenous materials.

The effect of transmural pressure gradients on arterial transport of macromolecules and water has been studied to explain the occurrence of intimal hyperplasia and hypertension (Huang, 2004; Kenyon, 1979; Meyer, 1996; Prosi, 2005; Tada, 2001). Meyer et al. investigated the effects of pressure-induced stretch on low-density lipoprotein (LDL) and albumin uptake in the rabbit aortic wall. First, they determined the external diameter as a function of applied pressure. They found that the diameter increased nonlinearly with pressure. Reconstruction of their data showed a perfect polynomial fit ($R^2=1$) to a power of two. A correlation between pressure and macromolecule uptake was also observed. Albumin was shown to follow the same trend as the matrix distension with pressure and when constrained to prevent distension the uptake was not influenced by pressure. Albumin showed a uniform increase across the aortic wall with an increase in pressure from 70 to 120 mm Hg, but little difference was seen with an increase from 120 mm Hg to 160 mm Hg. A maximum distension is achieved at which albumin uptake did not change despite a significant increase in transmural pressure, indicating the importance of distension rather than transmural pressure. The concentration of LDL was much more pronounce in the intima than in the media and levels were lower in comparison to albumin. This was most likely due to the larger size of this molecule in comparison to albumin. The concentration of LDL was linearly dependent on the pressure. Meyer et al. shows an increase in concentration close to the lumen, but the concentration reaches a maximum in the media at 120 mm Hg and is no longer influenced by an increase in pressure (Meyer, 1996). This follows the trend of the distension of the aortic wall as the increase in diameter above 120 mm Hg is small.

Further analysis of the effects of pressure-induced transport was done by Meyer et al. by wrapping the aortas with 4 and 5 mm sleeves. The unwrapped segments had higher concentrations hear the lumen for LDL and higher concentrations almost uniformly across the wall for albumin. Their conclusion is that pressure-induced stretching of the wall is a major determinant of arterial mass transport Pressure-induced vector transport was examined in human saphenous vein (Ander, 2005). Biologically inert microspheres (100 nm) were introduced to the vein wall at 100, 200 and 400 mm Hg and compared to 0 mm Hg. More particles were found along the intima (thickness of 0.1 mm) of vessels perfused at pressures above 0 mm Hg. Nearly twice the area of microspheres was found along the intima at 100 mm Hg and 400 mm Hg than at 0 mm Hg. Although, the percent areas at the intima were not significantly different between 100, 200 and 400 mm Hg. The microspheres in the media (thickness of 0.5 mm) were less than 0.1% on average. Ander et al. hypothesize that at pressures greater than 100 mm Hg, medial tissue components become compacted and the IEL pores collapse (Ander, 2005). The pores of the IEL for arteries are typically around 1 to 2 µm which can be limiting to large particles (Tada, 2001).

There is evidence that an increase to mass transport is indirectly related to a transmural pressure gradient that induces stretching of the matrix. If it is assumed the interstitial fluid and extracellular matrix is incompressible, this induced-stretch is needed to allow for volume change. There is also a limit to the influence of transport at maximum distension where an increase in pressure does not increase the fluid flux and may even inhibit flow due to compaction.

As described in more detail below, a process employing a pressure gradient across a blood vessel was used to more effectively perfuse vascular tissue and remove cells and cellular debris while preserving the integrity of the tissue in order to prevent an immune assault. The process can be employed as for delivering a surfactant (for example, sodium deoxycholoate or Triton X-100), and can be used as a vascular perfusion method. This process has advantages over other processing methods for saphenous vein allografts, which preserve cells to maintain functionality and prevent occlusions. It has been shown the endothelial layer sloughs off and grafts become acellular. During this process cell antigens elicit an inflammatory immune response leading to early stenosis. Attempts at successfully removing cellular antigens have failed unless extensive chemical treatments are applied but these nevertheless lead to vascular occlusion. These attempts are multi-day and often result in matrix damage and/or toxicity. An advantage of the present processes is that it allows for shorter treatment times while still providing tissue with high integrity for implantation.

A device was constructed that allows constant flow of a cleaning agent such as sodium deoxycholate (a preferred cleaning agent for decellularization) at a constant pressure to increase the transport of the surfactant into the saphenous vein wall in order to remove the cellular elements more rapidly than shaking. Results at pressures of 100 mm Hg and 200 mm Hg for one hour and two hours were used to obtain the physical parameters of the system. It was shown that the use of pressure in the process of the present invention allows for more effective decellularization at lower temperatures and in shorter times.

See Example 3 which illustrates a non-limiting example of this technology.

An additional aspect of the present technology is a multi-step process (i.e. recipe) that combines all of the foregoing processes, i.e. sterilization, decellularization and pressure-induced processing.

EXAMPLE 1

Processing Parameters

Cell Removal:

The effectiveness of cell and cellular debris removal was evaluated using two detergent and two enzyme solutions at various concentrations (Table 2). The detergents used in this study were Triton-X 100 at 0.25% (v/v) and 1.0% (v/v) and sodium deoxycholate (Cholate) at 0.25% (w/v) and 1.0% (w/v). Due to viscosity issues with sodium deoxycholate at low temperatures, tests were repeated at 0.5% (w/v). One treatment group combined Triton-X 100 with sodium deoxycholate. Trypsin alone at 0.05% (w/v) or 1.0% (w/v) and in combination with 0.02% (w/v) EDTA were the enzyme solutions used in the decellularization process. EDTA was also combined with Triton for a comparison since the Trypsin samples appeared grossly degraded after treatment.

Samples of human saphenous veins 10 mm in length were placed in each of the test solution at 37° C. or 48° C. for both 6 and 24 hours while continuously shaking. Samples were then rinsed in PBS at room temperature for 10 minutes while continuously shaking. Following the rinse step, the samples were cut in half and either prepared for histology or immunohistochemistry.

TABLE 2

Processing parameters to evaluate decellularization of human saphenous vein.

| Cleaning Agent | Concentrations (%) | |
|---|---|---|
| Trypsin | 0.05 (w/v) | 1.0 (w/v) |
| Trypsin/EDTA | 0.05/0.02 (w/v) | 1.0/0.02 (w/v) |
| Triton | 0.25 (v/v) | 1.0 (v/v) |
| Cholate | 0.25 (w/v) | 1.0 (w/v) |
| Triton/Cholate | 0.25/0.25 | 1.0/1.0 |
| Triton/EDTA | 0.25/0.02 | 1.0/0.02 |

Histology:

Samples were placed in 10% buffered formalin immediately following the rinse step and remained there for at least 24 hours before further preparation. Then, the samples were embedded in paraffin and stained with hematoxylin and eosin (H&E) to determine cellularity.

Immunohistochemistry:

Immunohistochemistry was used to determine the level of antigens remaining in the tissue after treatment. Class I MHC antibodies were used for evaluation since class I antigens are present in a much greater abundance than class II antigens. Samples were prepared in frozen blocks and sectioned with a cryostat. The sections were thawed and then rinsed for blocking and antibody staining. Sections were incubated for 30 minutes in primary antibody (mouse anti-HLA-ABC class I MHC) solution and then for anther 30 minutes in diluted biotinylated secondary antibody (Vector ABC Elite kit) solution. An enzyme substrate, NovaRed (Vector), was used to stain the antibodies red. The counter stain was hematoxylin providing a blue contrast.

Optical Evaluation:

A Zeiss Axiophot 2 microscope with a motorized Ludl scanning stage was used with tile field mapping at 5× to capture the entire image in one frame. Particle analysis was performed in Image J to determine the ratio of antigen staining (red) to the total tissue sample.

Matrix Integrity:

One of the major structural components of the extracellular matrix that gives veins their strength is collagen. Damage to collagen can result in mechanical failures such as increased compliance or aneurism formation. It can also result in a cellular response due the exposure of the triple helix when stability is compromised. The amount of collagen denaturation was assessed to evaluate processing conditions with a quantitative enzyme digestion assay. Saphenous vein samples (0.2 to 0.25 g) were treated with trypsin, a serine protease enzyme that is able to digest only those collagen fibers that possess a break in the helix known as denaturation. Digested and undigested fractions are separated and hydrolyzed with concentrated hydrochloric acid (HCl) to release free amino acids from each fraction. Following neutralization of the acid in 1 N NaOH, levels of hydroxyproline (an amino acid present in high concentrations in collagen) are assessed in each fraction by a calorimetric method at a wavelength of 550 nm (Chloramine T binding, and reduction of the substrate DAB to a colored end product). The level of denatured collagen in a given sample is then expressed as a percent of the trypsin soluble fraction to the sum of both trypsin soluble and trypsin insoluble fractions.

Statistics:

Data was analyzed with a two-sample student's t-test with an $\alpha$ value of 0.05 using Minitab Statistical software. A p-value less than $\alpha$ was considered a significant effect.

Figure 2:
FIG. 2 is a view of the result of the application of a threshold filter that limits the pass of high intensity blues.

Results:

The red staining as a result of the class I MHC antigens on the endothelial cells and the smooth muscle cells ranged from a bright red to a dark brown. A blue and green filter was applied to only allow red to pass. Obvious areas of antigen staining were removed due to this variation in red hue. Therefore, only a blue filter was applied where a threshold value was determined when the blue-stained negative control disappeared while both green and red were allowed to fully pass to capture a greater portion of the antigen staining. All samples were compared to their negatives for a percentage of red staining. FIG. 1 shows a tile mapped image of the a positive control and a negative control. FIG. 2 shows the result after a threshold filter was applied. The negative control on the right is almost completely devoid of any particles, whereas the positive control removes the background stained tissue and retains the stained antigens.

Figure 3:
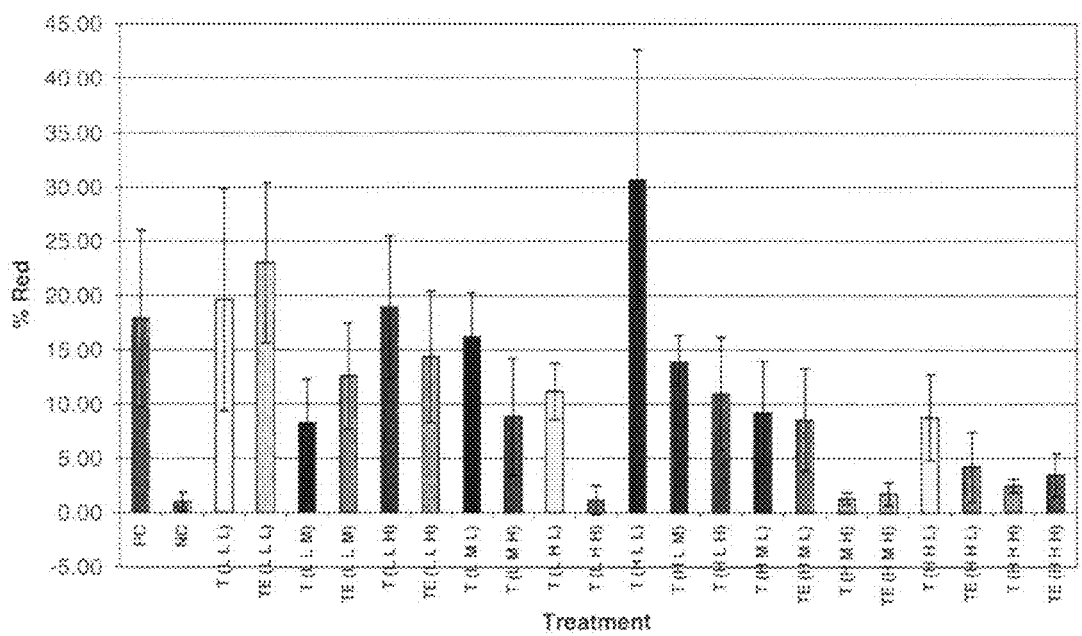
FIG. 3 is a view of the amount of class I MHC remaining in the tissue when compared to a negative control. The treatment group labels are T (Trypsin) and TE (Trypsin+EDTA) and the conditions are in order of concentration (L=0.25%, H=1.0%), temperature (L=37° C., M=48° C., H=55° C.) and time (L=6 hrs, M=17 hrs, H=24 hrs).
Figure 4:
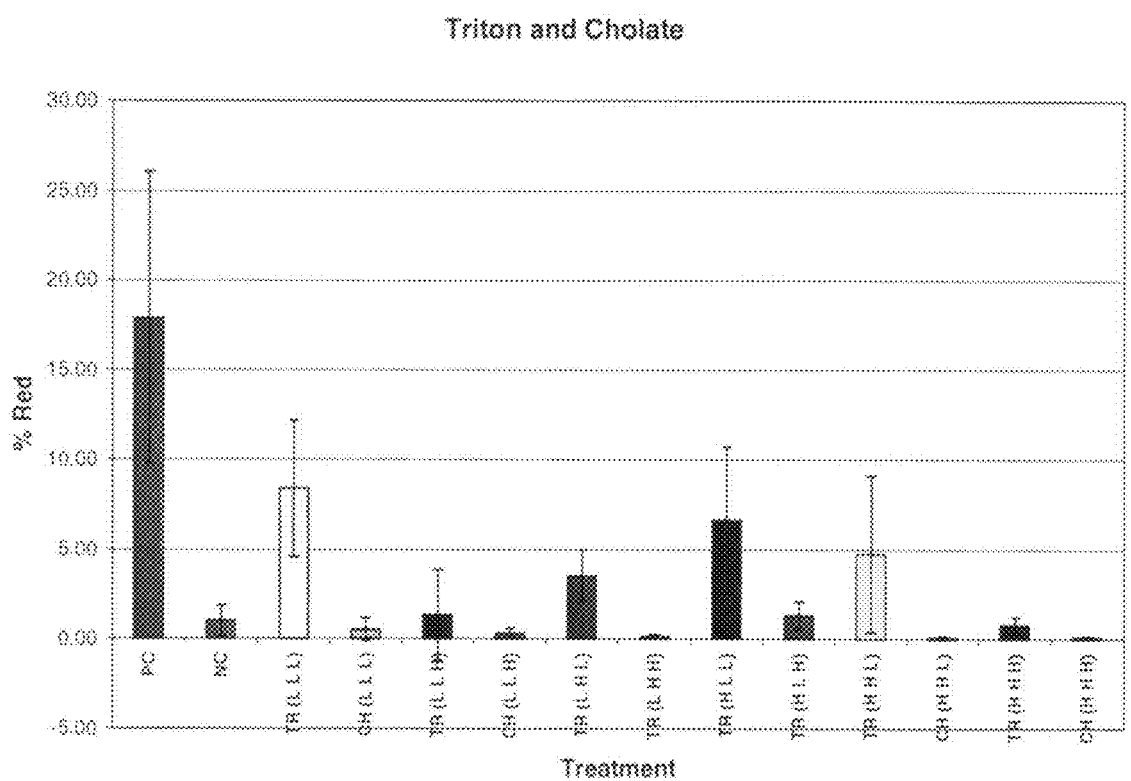
FIG. 4 is a view of the amount of class I MHC remaining in the tissue when compared to a negative control. The treatment group labels are TR (Triton) and CH (cholate) and the conditions are in order of concentration (L=0.25%, H=1.0%), temperature (L=37° C., H=48° C.) and time (L=6 hrs, H=24 hrs).

This procedure was applied to all images. There were three samples per treatment group and the result of each sample was averaged from three sections. The results for the Trypsin and Trypsin+EDTA treatment groups are shown in FIG. 3 and the results for the Triton-X 100 and sodium deoxycholate (cholate) treatment groups are shown in FIG. 4. The treatment groups are labeled according to the detergent or enzyme used followed by the processing conditions. For the Trypsin and Trypsin+EDTA groups, the concentrations ranged from 0.05% (L) to 1.0% (H), the processing temperatures were 37° C. (L), 48° C. (M) and 55° C. (H), and the processing times were 6 hrs (L), 17 hrs (M) and 24 hrs (H). For the Triton and cholate groups, the concentrations ranged from 0.25% (L) to 1.0% (H), the processing temperatures were 37° C. (L) and 48° C. (H), and the processing times were 6 hrs (L) and 24 hrs (H).

The results indicate that increases in processing temperature and in concentrations of the cleaning agents in the solutions had a greater effect on removal of antigenicity than increases in contact time. A significant reduction in red staining at 6 hours was only seen with an increase in temperature and concentration. Six groups in the Trypsin and Trypsin/

EDTA experiments had a less than 5% red staining when compared to the negative controls. Treating the tissue with 1.0% Trypsin or 1.0%/0.02% Trypsin/EDTA at a minimum of 48° C. and 17 hrs significantly reduced the level of antigens. Only at temperatures of 55° C. was there a significant decrease in red staining within 6 hrs. The addition of EDTA has an inconsistent effect on the removal of antigens from the tissue.

Figure 5:
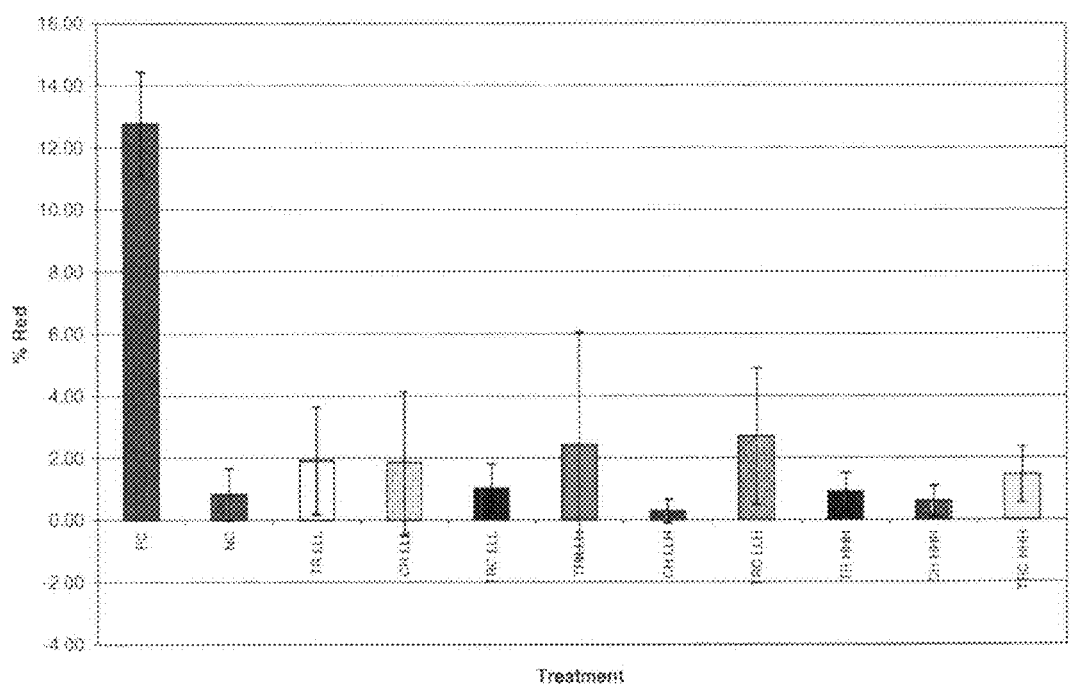
FIG. 5 is a view of the amount of class I MHC remaining in the tissue when compared to a negative control. The treatment group labels are TR (Triton), CH (cholate), and TRC (Triton plus Cholate) and the conditions are in order of concentration (L=0.25%, H=1.0%), temperature (L=37° C., H=48° C.) and time (L=6 hrs, H=24 hrs).
Figure 6:
FIG. 6 is a view of representative samples of tissue treated with Trypsin (left), Triton-X 100 (center) and sodium deoxycholate (right) and stained for class I MHC antigens.

For Triton and Cholate, all but three treatment groups were below 5% staining and all of them were below 10% staining when compared to the controls. Cholate exhibited the least amount of staining with approximately 100% removal (approximately 0% staining) at the high concentrations and high temperatures. There was no statistical difference in samples treated with Triton and Cholate combined compared to individually (FIG. 5). The addition of EDTA to Triton did enhance the removal of cells at 0.25% for 6 hours at 37° C. Representative samples from each group are shown in FIG. 6 for comparison.

Figure 7:
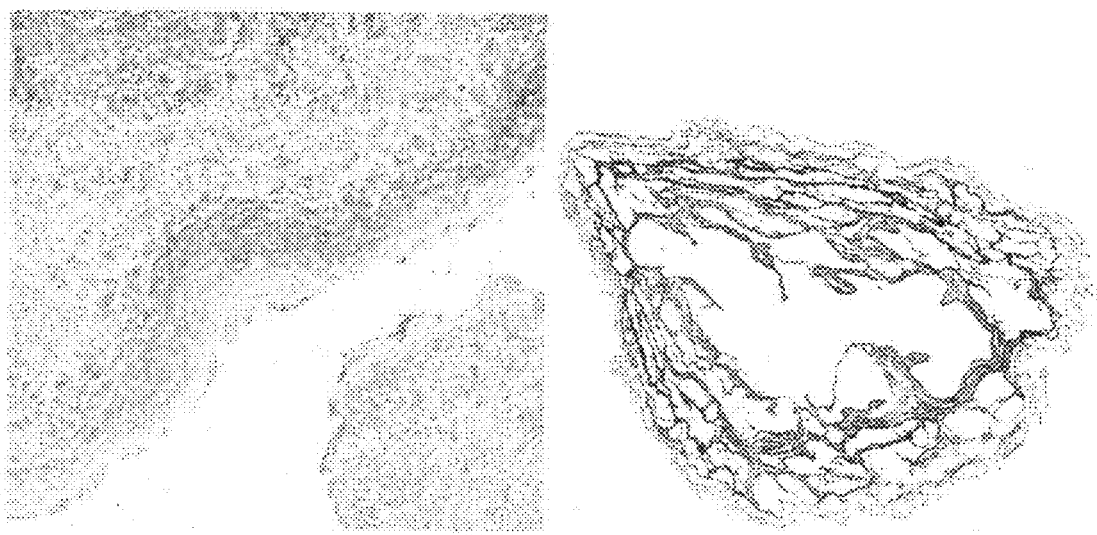
FIG. 7 is a view of a comparison of the amount of cellularity (blue) visible in histology compared to the amount of antigens (red) present in the tissue. The samples were treated with 0.05% Trypsin at 37° C. for 6 hours.
Figure 8:
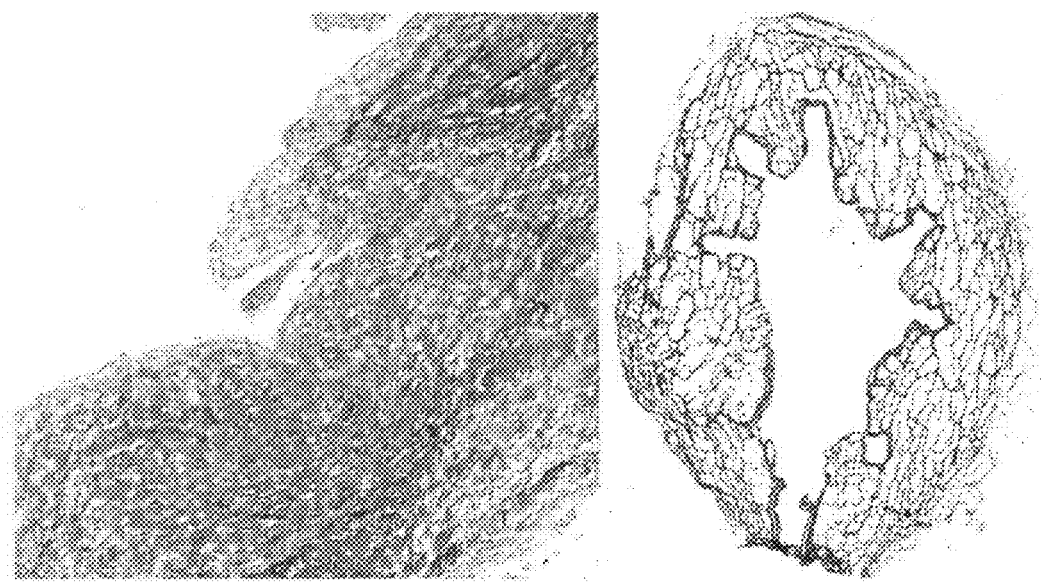
FIG. 8 is a view of a comparison of the amount of cellularity (blue) visible in histology compared to the amount of antigens (red) present in the tissue. The samples were treated with 0.05% Trypsin at 37° C. for 24 hours.
Figure 9:
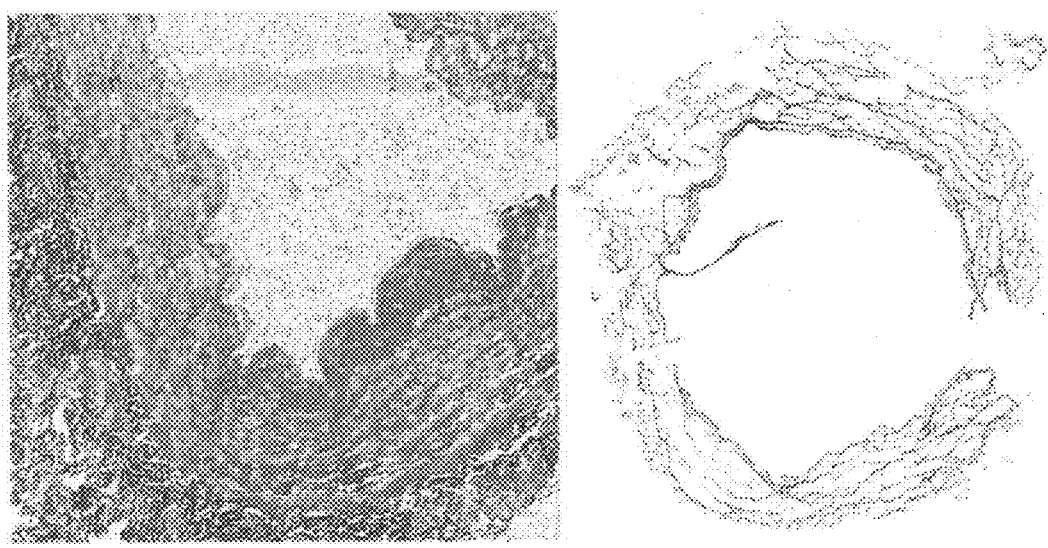
FIG. 9 is a view of a comparison of the amount of cellularity (blue) visible in histology compared to the amount of antigens (red) present in the tissue. The samples were treated with 0.25% Cholate at 37° C. for 6 hours.
Figure 10:
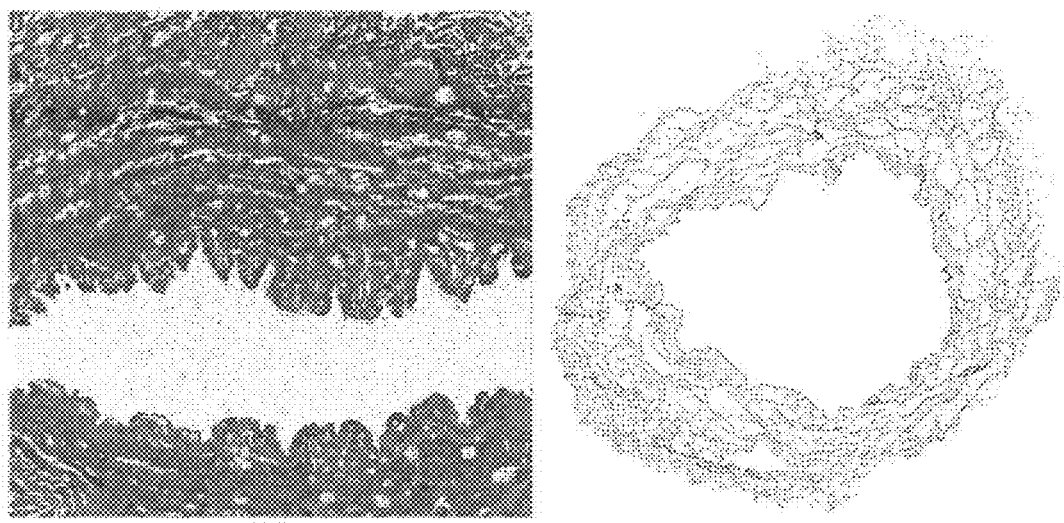
FIG. 10 is a view of a comparison of the amount of cellularity (blue) visible in histology compared to the amount of antigens (red) present in the tissue. The samples were treated with 1.0% Cholate at 48° C. for 6 hours.

The results of the immunohistochemical stain were compared to histology slides stained for cellularity (FIGS. 7 to 10). There is still evidence of cells in the samples treated with Trypsin and that is correlated with red stained tissue in the immunohistochemical slides. FIG. 7 appears to have a reduction in the amount of cellular material present in the matrix, but red stained segment shows a majority of the tissue still contains antigens. The extracellular matrix is preserved in each segment except with 1.0% Cholate at 48° C. There are large holes within the venous wall and separation between the fibers.

Figure 11:
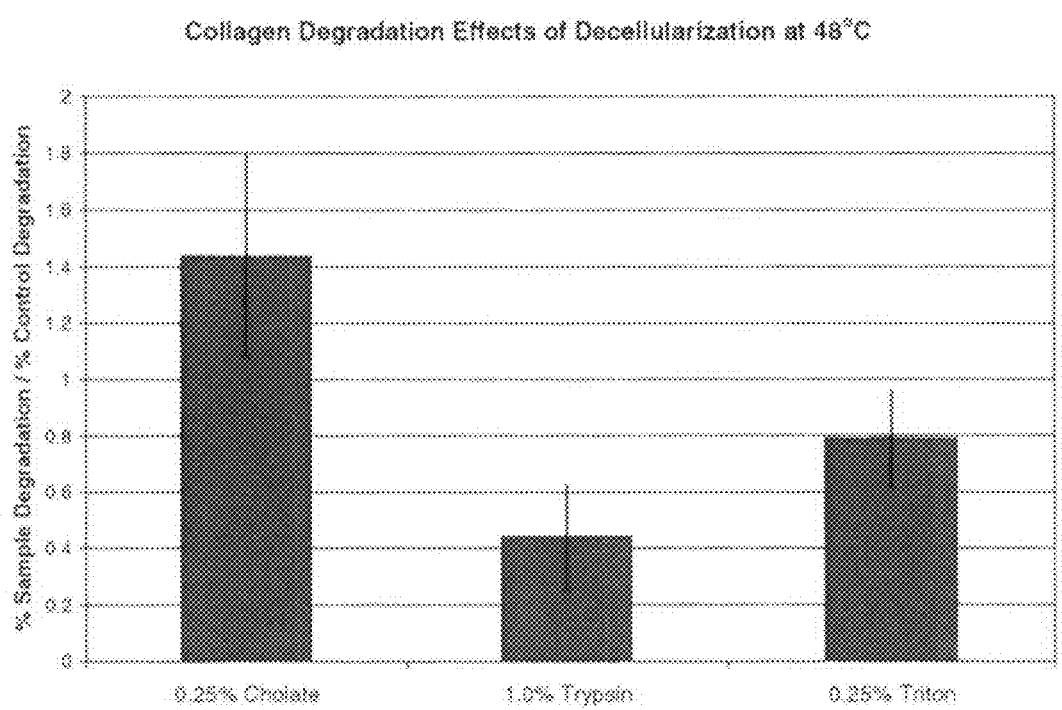
FIG. 11 is a view of results of a collagen degradation assay after decellularization at 48° C. for 24 hours. The samples were donor matched to reduce the inherent variability in tissue.

The conditions for each chemical that produced a reasonable reduction in red staining were analyzed quantitatively for their effect on collagen. Triton at 1.0% and Cholate at 0.25% were contacted with samples at 48° C. for 24 hours under constant agitation. The samples were immediately placed in an ice bath after the 24 hours and then rinsed in cold phosphate buffered saline (PBS) to halt any degradation due to the temperature increase. The results were compared to the natural degradation of the untreated controls and are shown in FIG. 11.

A ratio of one indicates no difference from the untreated controls. A significant degradative effect was not seen with cholate or Triton, although cholate had a more significant effect than Triton on the tissue matrix. The Trypsin showed less than half of the degradation of the untreated controls.

EXAMPLE 2

Reduction Curves (Survivor Curves) for Spores

Figure 12:
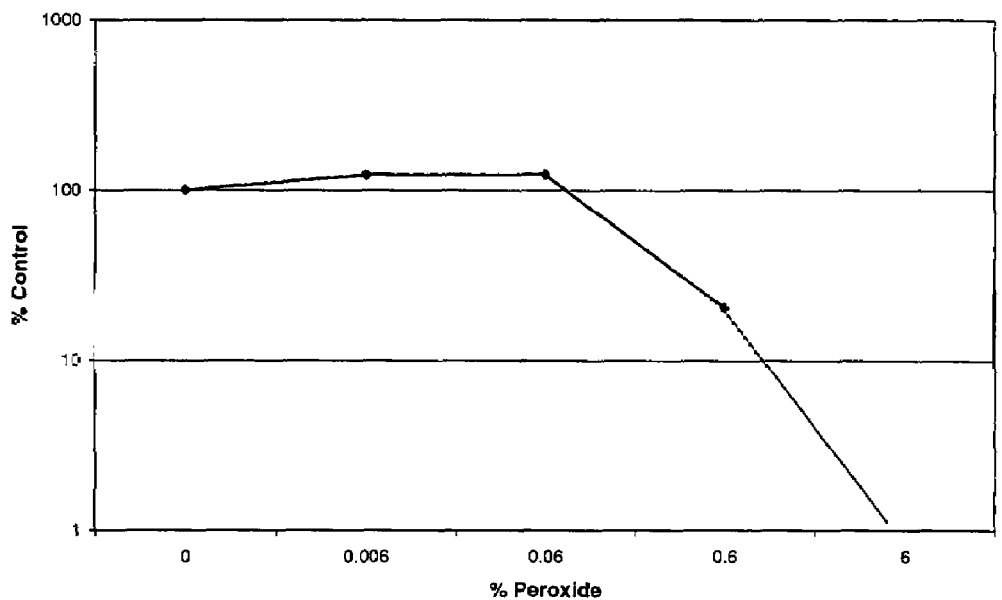
FIG. 12 is a view of *Bacillus stearothermophilus* growth inhibition at different dilutions of hydrogen peroxide on A. TSA and B. blood agar plates.
Figure 12:
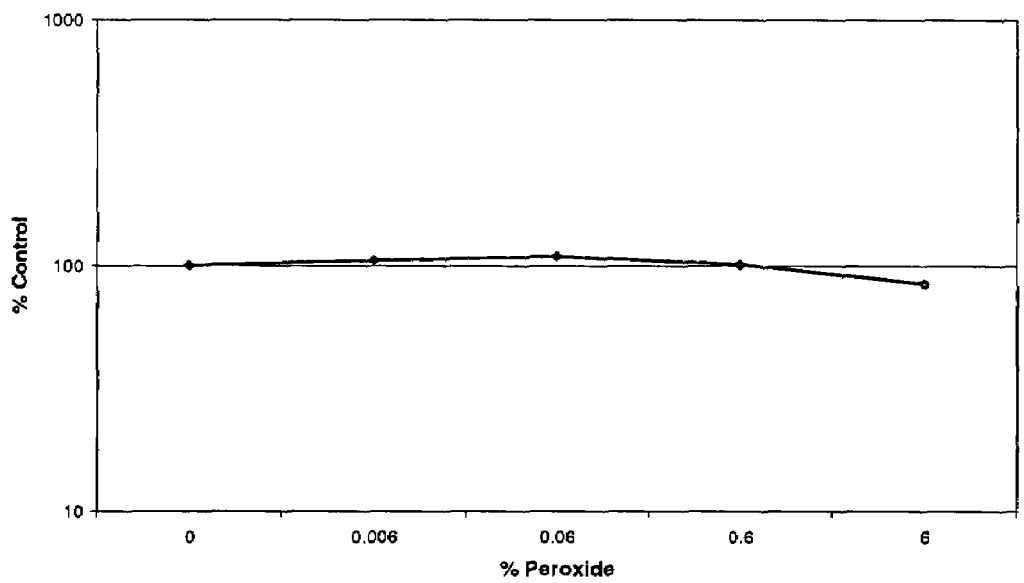
Figure 13:
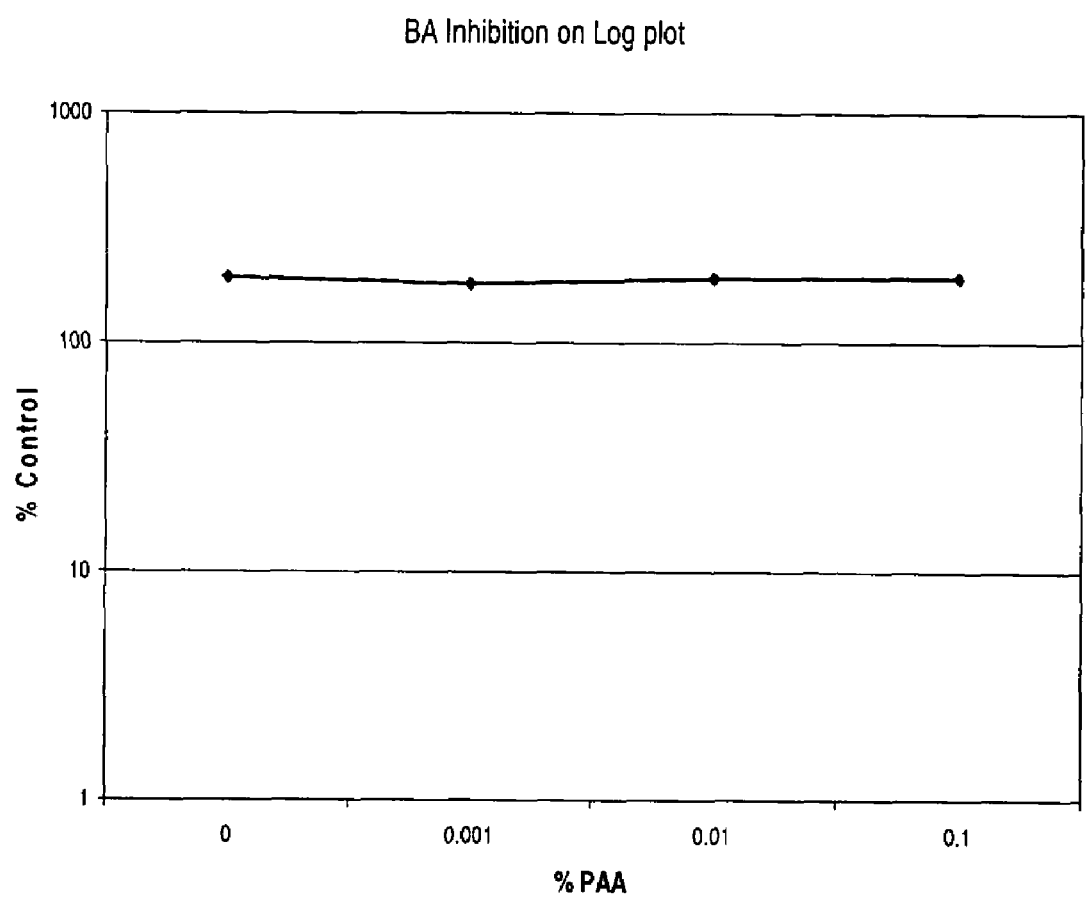
FIG. 13 is a view of *Bacillus stearothermophilus* growth inhibition at different dilutions of peracetic acid on blood agar plates.
Figure 14:
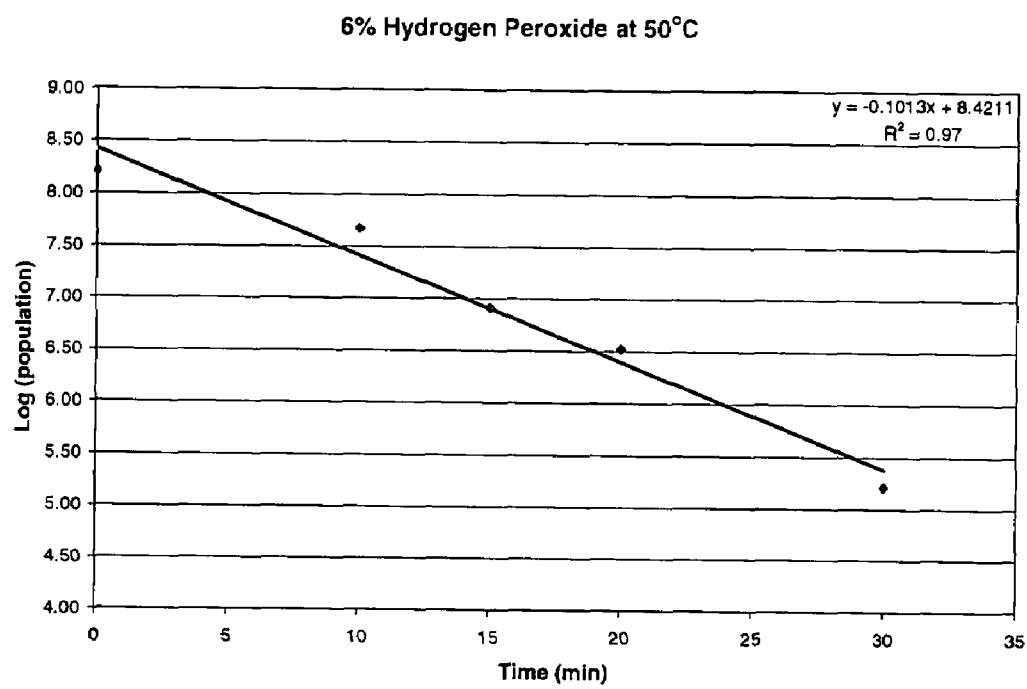
FIG. 14 is a view of the survivor curve for 6% peroxide at 50° C. resulting in a D-value of 9.87.
Figure 15:
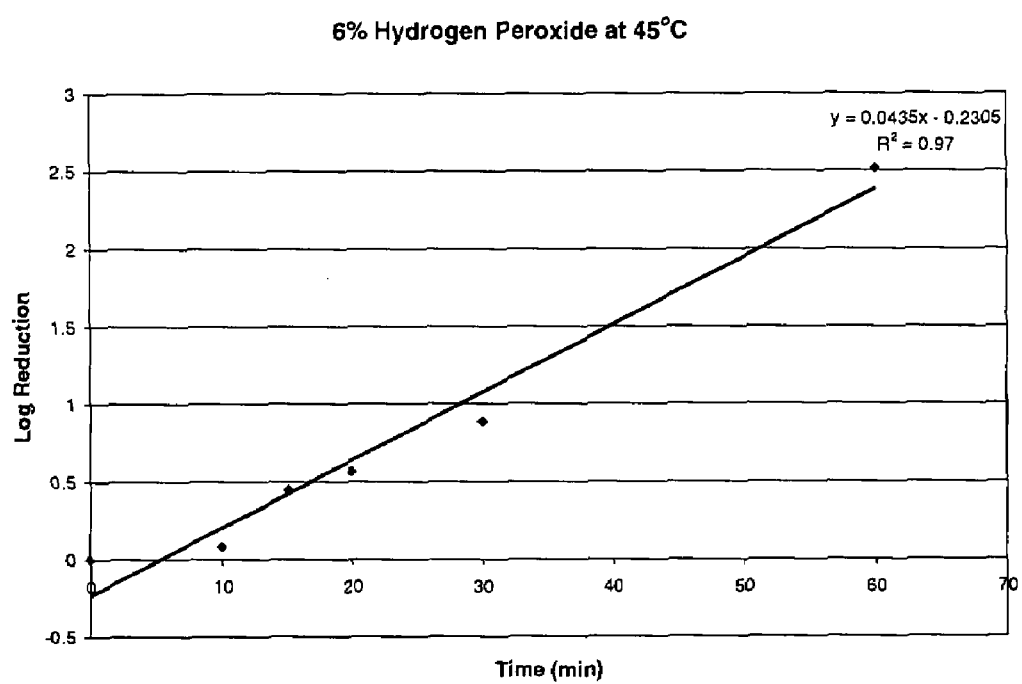
FIG. 15 is a view of the reduction curve for 6% peroxide at 45° C. resulting in a D-value of 23.0.
Figure 16:
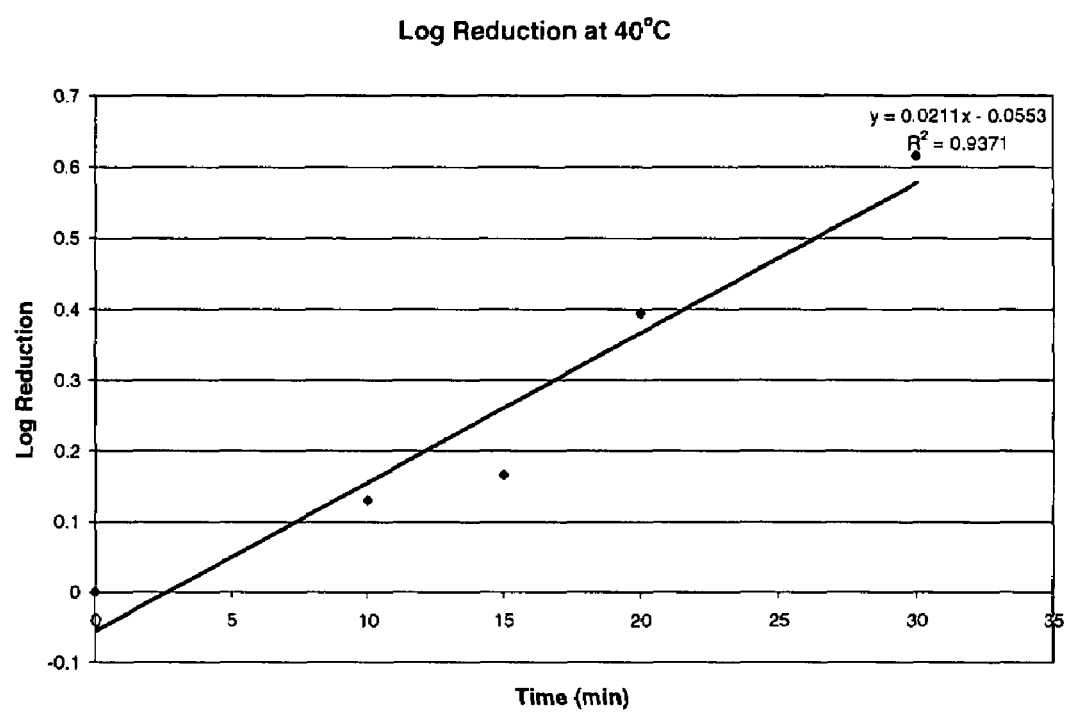
FIG. 16 is a view of the reduction curve for 6% peroxide at 40° C. resulting in a D-value of 47.39.
Figure 17:
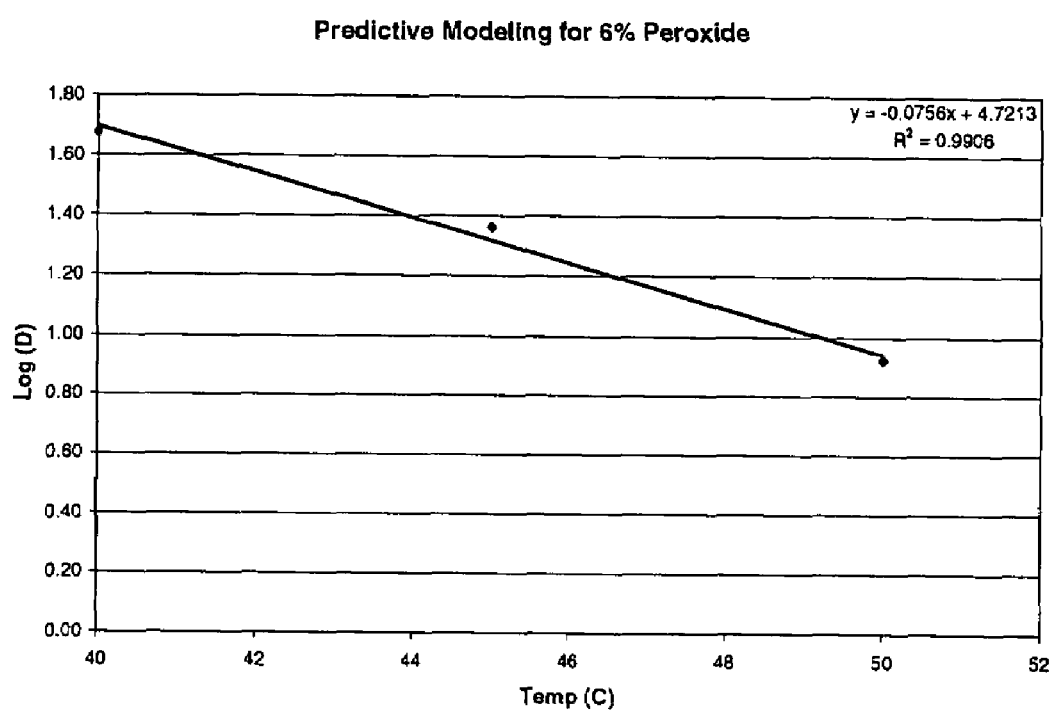
FIG. 17 is a view of the linear regression of the log of the D-values for each temperature. This gives an equation to interpolate and extrapolate the D-values at various temperatures with 6% hydrogen peroxide.
Figure 18:
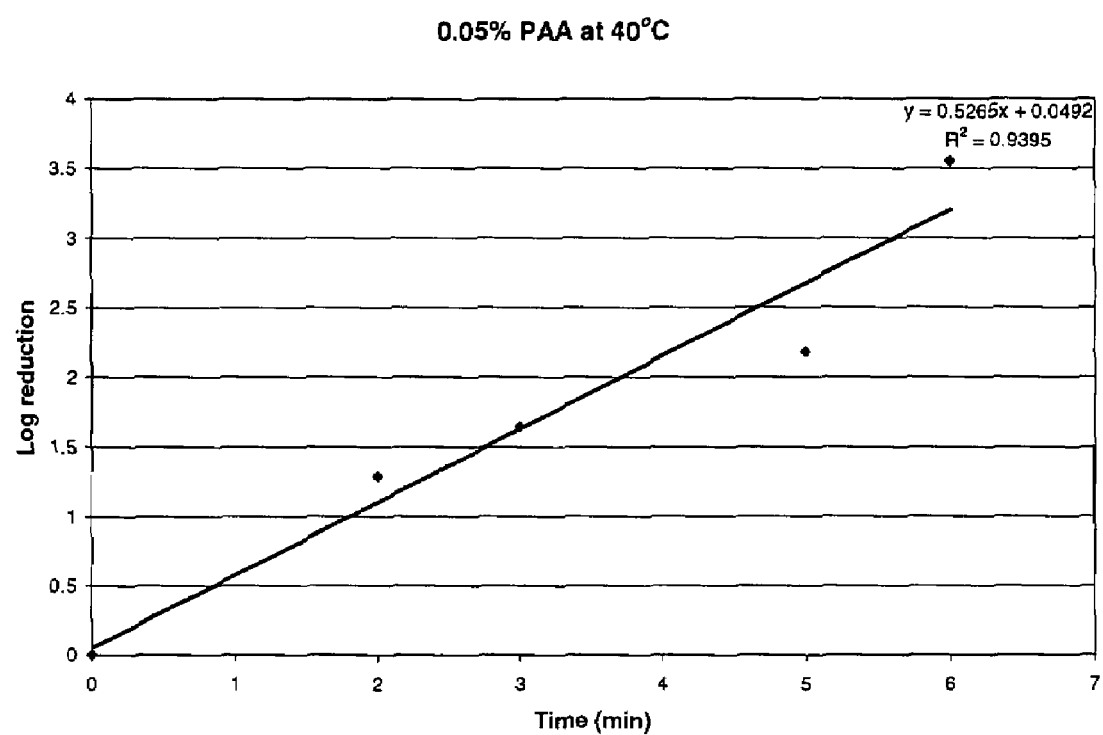
FIG. 18 is a view of the reduction curve for 0.05% PAA at 40° C. resulting in a D-value of 1.90.
Figure 19:
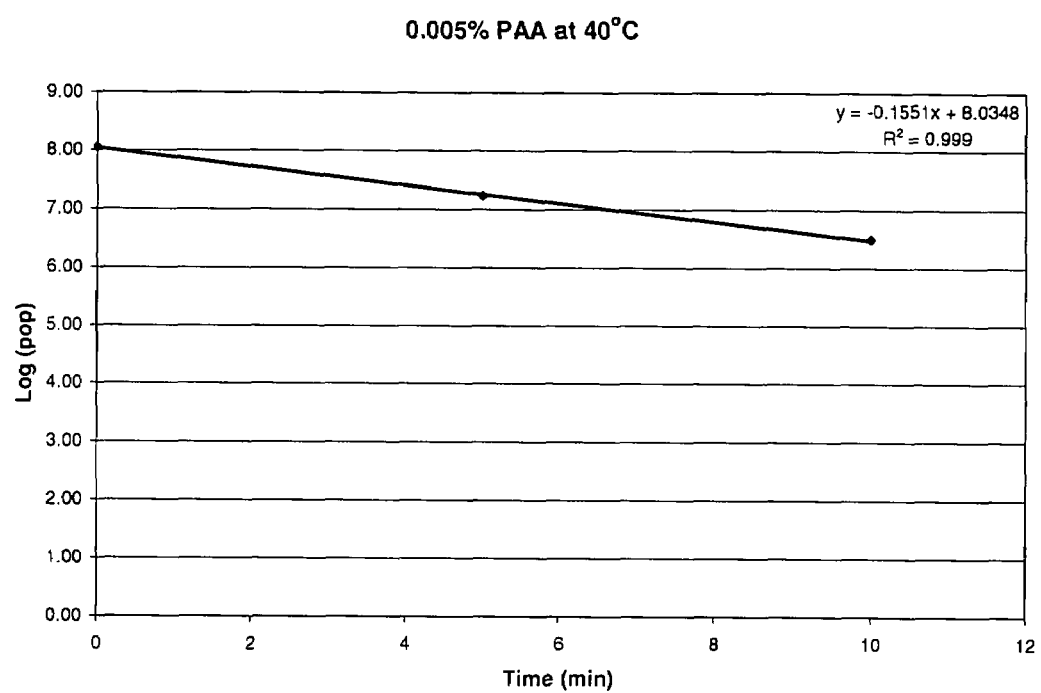
FIG. 19 is a view of the survivor curve for 0.005% PAA at 40° C. resulting in a D-value of 6.45.

In order to determine the reduction in spores after processing with cleaning agents, an effective and consistent method was developed. Initially, a 107 spores/ml titre of *B. stearothermophilus* was used to enumerate the remaining population after treatment on both TSA media plates and sheep's blood agar (BA) plates. It was determined that residual hydrogen peroxide inhibited the growth at concentrations of 0.6% or higher for TSA plates and 6% or higher for blood plates (FIG. 12). It is believed that the catalase contained in the blood agar plates inactivated the hydrogen peroxide. A similar investigation was performed on PAA, but no inhibition was observed within the processing concentrations (FIG. 13). Even though the blood agar plates allowed for dilutions as low as 1:10, the titre used was too low to detect more than a 3 log reduction in the process limiting the data collection for the survivor curves. Therefore, the titre used in this study was a 109 CFU/ml solution of *B. stearothermophilus*.

To ensure consistency, each vial was vortexed before each replicate and all of the material was removed from the pipette tip onto the plate. Disposable plate spreaders were used to prevent cross contamination. The moisture needed to be maintained at a certain level because the plates would dry out at 60° C., but if there was too much moisture the bacteria would streak across the plate and prevent an accurate count. The first procedure implemented was propping the plates open in a laminar flow hood to allow excessive moisture to dry. The second method employed was placing the plates in a beaker with a porous covering to trap some moisture while allowing the excess to evaporate. This resulted in consistent and evenly spread bacteria on the pour plates.

Hydrogen Peroxide:

Hydrogen peroxide at a concentration of 6% was used at temperatures of 40, 45 and 50° C. to calculate a curve for modeling the temperature effects on spore kill. A vial with 0.9 ml of germicide was prewarmed in a water bath and then injected with 0.1 ml of spore solution (108 spores/ml). Samples were removed and immediately placed in an ice bath at 10, 15, 20 and 30 min. The vial was well-mixed on a vortex, and then diluted 1:10 in series before plating. The plates were placed in an incubator between 55° C. and 60° C. for 20 to 24 hours.

Peracetic Acid:

Peracetic acid at concentrations of 0.1%, 0.05% and 0.005% were used only at 40° C. to calculate a curve for modeling the concentration effects on spore kill. Initial inactivation rates at 50° C. were too rapid to detect. A vial with 0.9 ml of germicide was pre-warmed in a water bath and then injected with 0.1 ml of spore solution (108 spores/ml). Samples were removed and immediately placed in an ice bath at various time points depending on the concentration. The vial was well-mixed on a vortex, and then diluted 1:10 in series before plating. The plates were placed in an incubator between 55° C. and 60° C. for 20 to 24 hours.

Spike and Recovery Method

Before enumerating the population remaining on tissue following chemical processing, the amount recoverable from the tissue must be determined. The recovery process developed involves the use of sonication, mechanical shaking and agitation on a vortex. Veins were cut into 30 mm segments and clamped at one end. The lumen of the vein was injected with 108 spores in a 0.1 ml inoculum. The other end was clamped and the veins were hung at 4° C. for 15 minutes avoiding contact with any surfaces. The samples were then cut from the clamps and split open over a centrifuge tube containing 39.9 ml of Letheen broth to expose the lumen to the recovery process. A new pair of scissors or a new scalpel blade were used for each vein and the segments were cut over the broth to catch anything that may not have adhered to the surface of the tissue.

The tubes were sonicated at room temperature for ten minutes to break the bacteria from the surfaces. The tubes were then placed on a shaker where they were for another 10 min. The Letheen broth containing the tissue sample was then vortexed for 30 s and diluted in a series of 1:10 dilutions with each dilution plated on blood agar plates. The plates were incubated overnight at 60° C.

Reduction Curves:

The procedure for spike recovery was used to collect data for the reduction curves. Vein segments were inoculated and then treated in one of the following conditions. Hydrogen peroxide (6%) was analyzed at 40° C. and 50° C. while peracetic acid (0.1%) was only tested at 40° C. At each time point, three samples were spiked and treated with one control for recovery efficiency.

Data Presentation:

Typically, a survivor curve is constructed with the initial population at time zero and the resultant populations at various time points. Since not all data points could be completed in the same day, some reduction curves were constructed to compare log reduction in the controls for each experiment over time. This normalized the data to its own experimental episode.

Matrix Integrity:

Achieving the appropriate log reduction should not come at the expense of the integrity of the extracellular matrix. The amount of collagen denaturation as a result of chemical treatments was analyzed by a quantitative enzyme digestion assay. The effect of hydrogen peroxide at 6% at 40° C. and 50° C. on collagen was compared to PAA at 0.1% at the same specified temperatures.

Saphenous vein samples (0.2 to 0.25 g) were treated with trypsin, a serine protease enzyme that is able to digest only those collagen fibers that possess a break in the helix known as denaturation. Digested and undigested fractions are separated and hydrolyzed with concentrated hydrochloric acid (HCl) to release free amino acids from each fraction. Following neutralization of the acid in 1 N NaOH, levels of hydroxyproline (an amino acid present in high concentrations only in collagen) are assessed in each fraction by a calorimetric method (Chloramine T binding, and reduction of the substrate DAB to a colored end product). The level of denatured collagen in a given sample is then expressed as a percent of the trypsin soluble fraction to the sum of both trypsin soluble and trypsin insoluble fractions.

Suspension Sterilization:

Temperature greatly influences the germicidal potential of hydrogen peroxide and PAA. The D-value for 6% peroxide was reduced by approximately 80% by an increase in temperature from 40° C. to 50° C. A 6 log reduction at 40° C. would take almost 5 hours where it takes less than an hour at 50° C. Results for PAA were only collected at 0.05% PAA or less and at 40° C. since at higher concentrations and higher temperatures the spore inactivation was too rapid to detect. A 6 log reduction at 0.05% PAA only takes 11 minutes and the D-value at 0.005% PAA at 40° C. is still less than 6% peroxide at 50° C.

Figure 20:
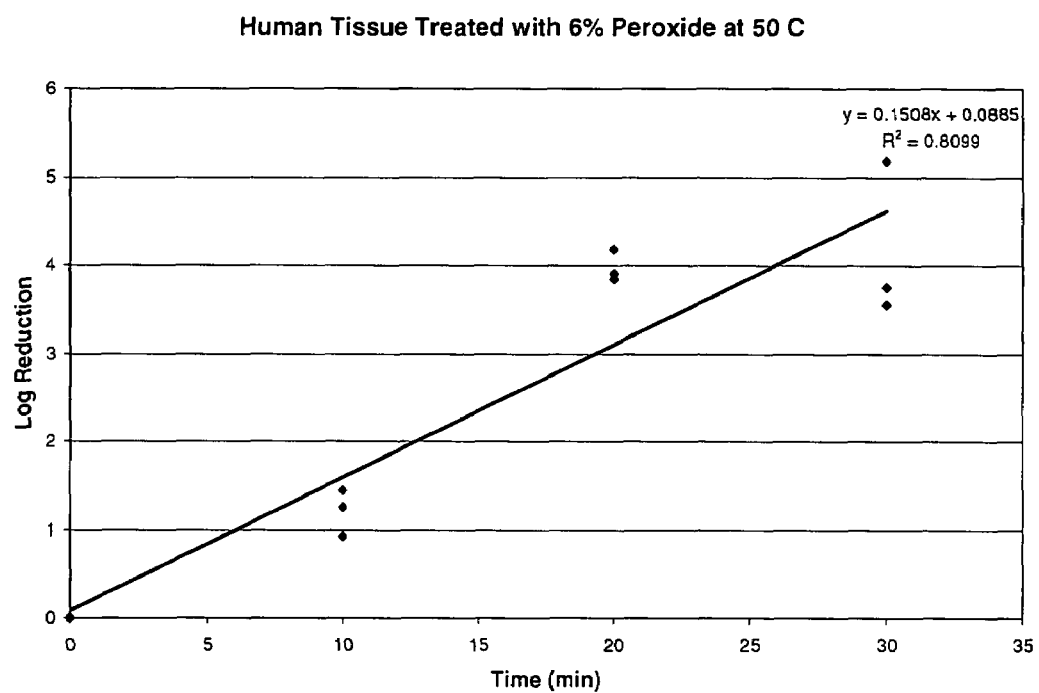
FIG. 20 is a view of the reduction curve for 6% hydrogen peroxide at 50° C. resulting in a D-value of 6.63.
Figure 21:
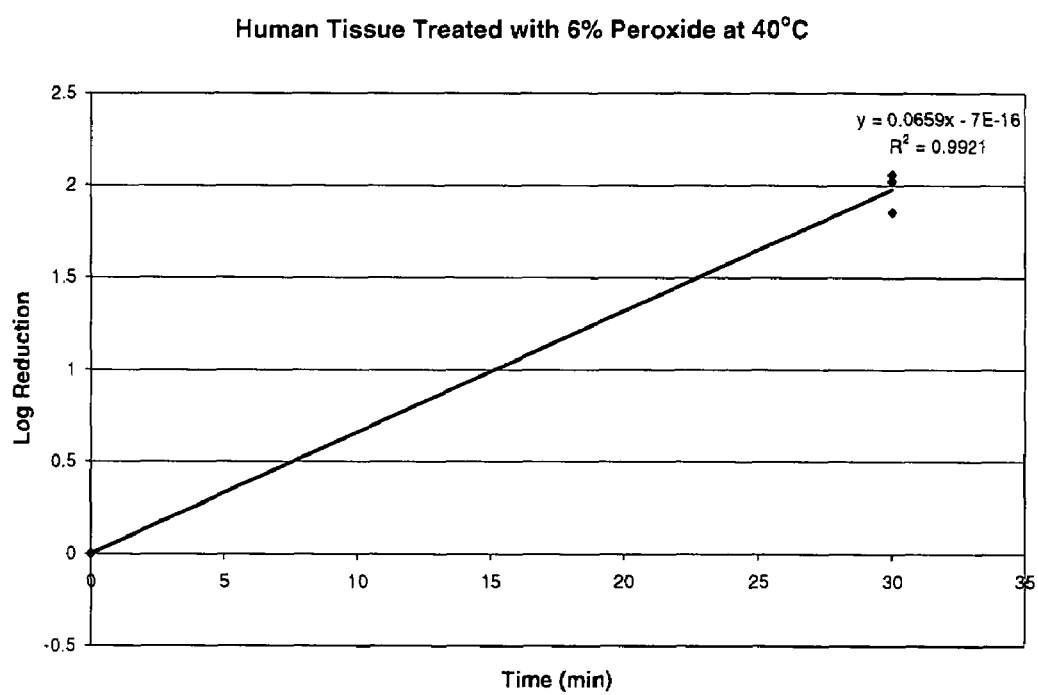
FIG. 21 is a view of the reduction curve for 6% peroxide at 40° C. resulting in a D-value of 15.17.

Tissue Sterilization:

The recovery method developed in the study consistently achieved between 52 and 73% spike recovery. A control was used at each experimental episode to provide a correction factor for the treated samples. The recovered population divided by the correction factor provides the surviving population after treatment. The reduction curves for spiked tissue treated with 6% hydrogen peroxide at 50° C. and 40° C. are shown in FIG. 20 and FIG. 21, respectively. According to the reduction curves, a 6 log reduction can be achieved in 1½ hours at 40° C. and in less than 40 minutes at 50° C. It was noted that the D-values of 6% peroxide with tissue were less than the D-values for spores treated in suspension. The D-value was decreased by approximately 4 minutes to 5.34.

Figure 22:
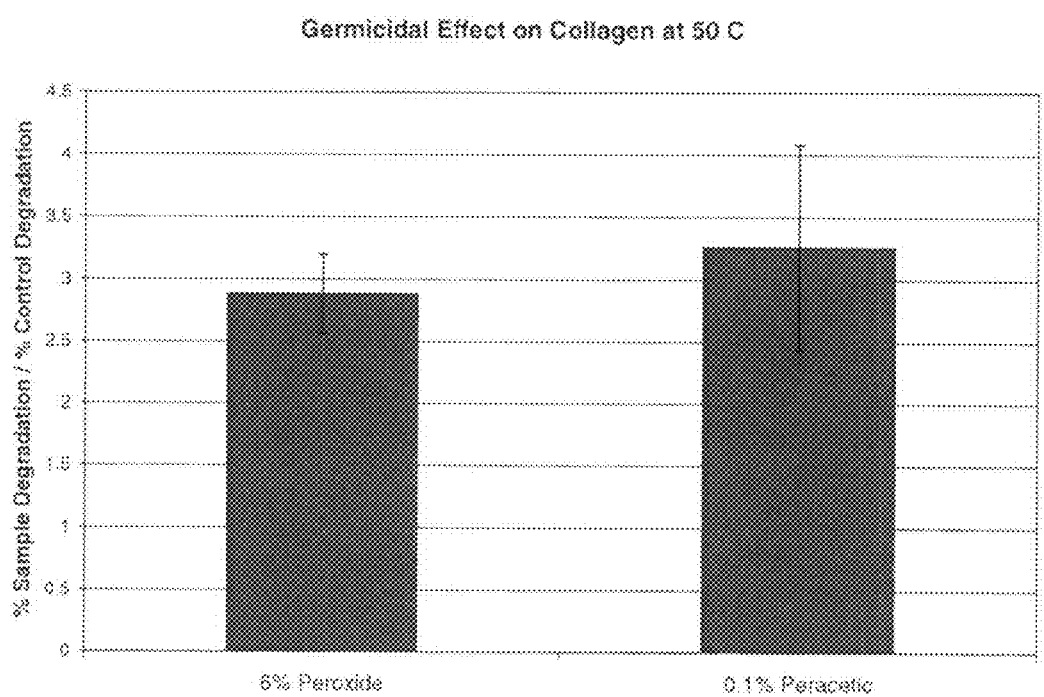
FIG. 22 is a view of a comparison of the germicidal effect on collagen for 6% hydrogen peroxide and 0.1% PAA at 50° C. (compared to a donor matched control).
Figure 23:
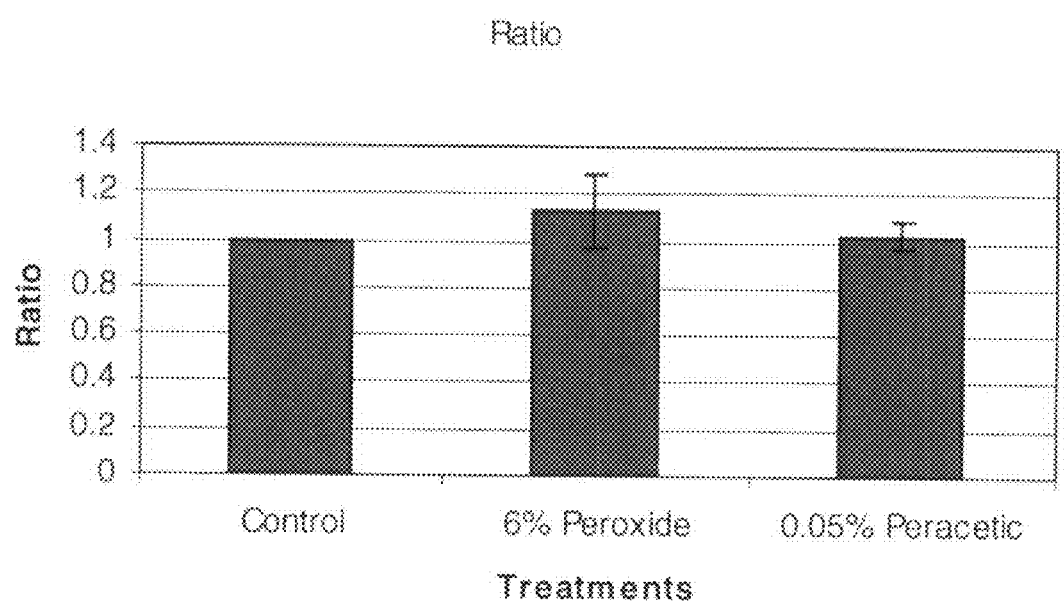
FIG. 23 is a view of a comparison of 6% hydrogen peroxide and 0.05% PAA at 40° C. (compared to a donor matched control).

Better spore kill is achieved at a high concentration of germicide and at a high temperature. The integrity of the tissue may be compromised at these extreme conditions. The ratio of degraded collagen after treatment in 6% hydrogen peroxide and 0.1% PAA at 50° C. for one hour were compared to untreated controls. The results are shown in FIG. 22. There was a statistical difference between peroxide and PAA, but both showed significantly altered matrix properties. A lower concentration of both germicides combined to inactivate the spore inoculum reduces the effects while still achieving the desired level of sterility.

pH Effects on Sterilizing with Hydrogen Peroxide:

In a separate study, 6% hydrogen peroxide was prepared in either DI water, PBS (pH 6) or PBS (pH 7.2). It was then used at 45° C. to treat *B. stearothermophilus* while under sonication. Results show that a buffered solution may be more effective. Thus, it is within the scope of the present invention to use buffered solutions, preferably those from about pH 6 to 8, more preferably about pH 6 to 7.2.

Efficiency of Peracetic Acid (PAA) vs. Hydrogen Peroxide (HP):

In a further study, the efficiency of peracetic acid (PAA) versus hydrogen peroxide (HP) was investigated. Samples were treated in either 0.1% PAA or 6% HP and were exposed for varying lengths of time at varying temperatures. See FIGS. 29-32.

Figure 29:
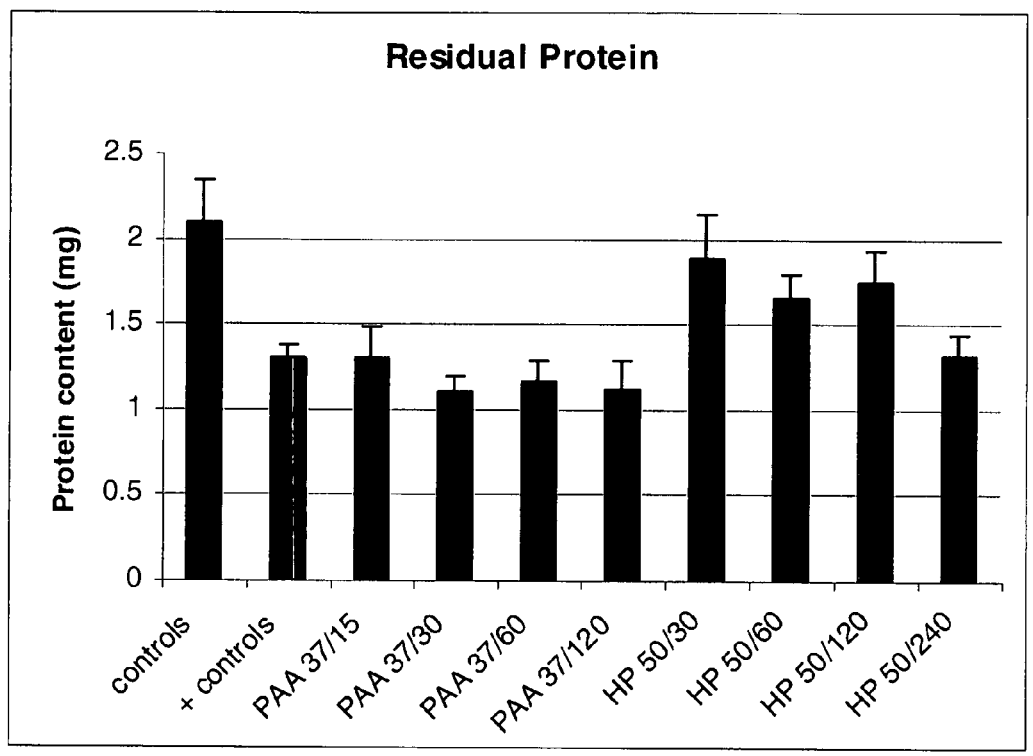
FIG. 29 is a view of samples of saphenous vein treated in 0.1% PAA or 6% HP for specified temperature (° C.) and length of time (min) (temp/time).
Figure 30:
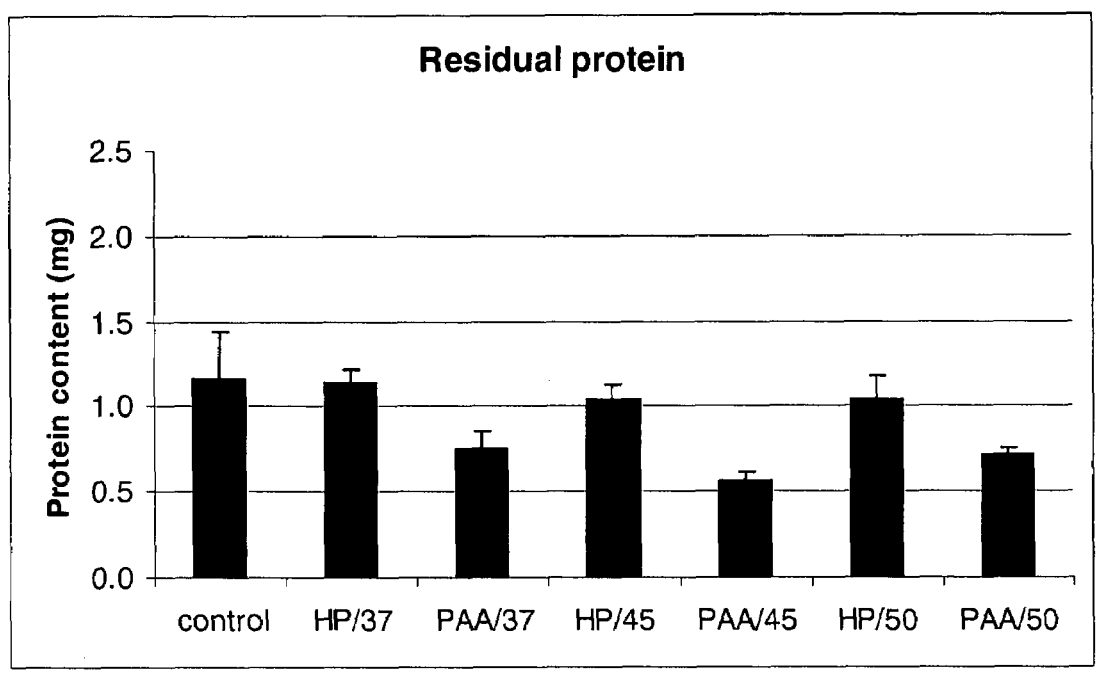
FIG. 30 is a view of samples of saphenous vein treated in 0.1% PAA or 6% HP for 60 min for a specified temperature (° C.).
Figure 31:
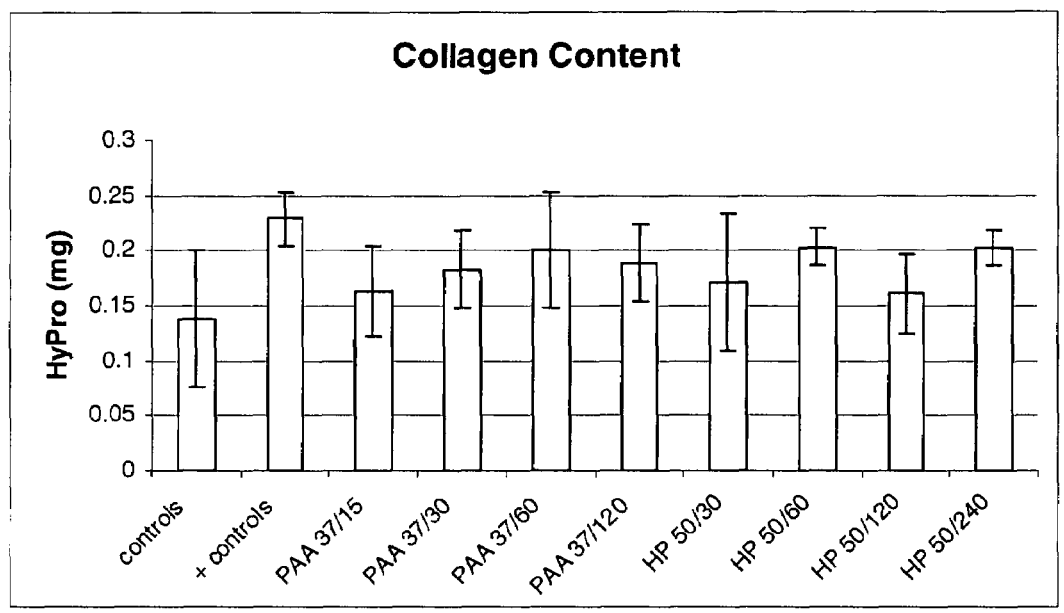
FIG. 31 is a view of samples of saphenous vein treated in 0.1% PAA or 6% HP for specified temperature (° C.) and length of time (min) (temp/time).
Figure 32:
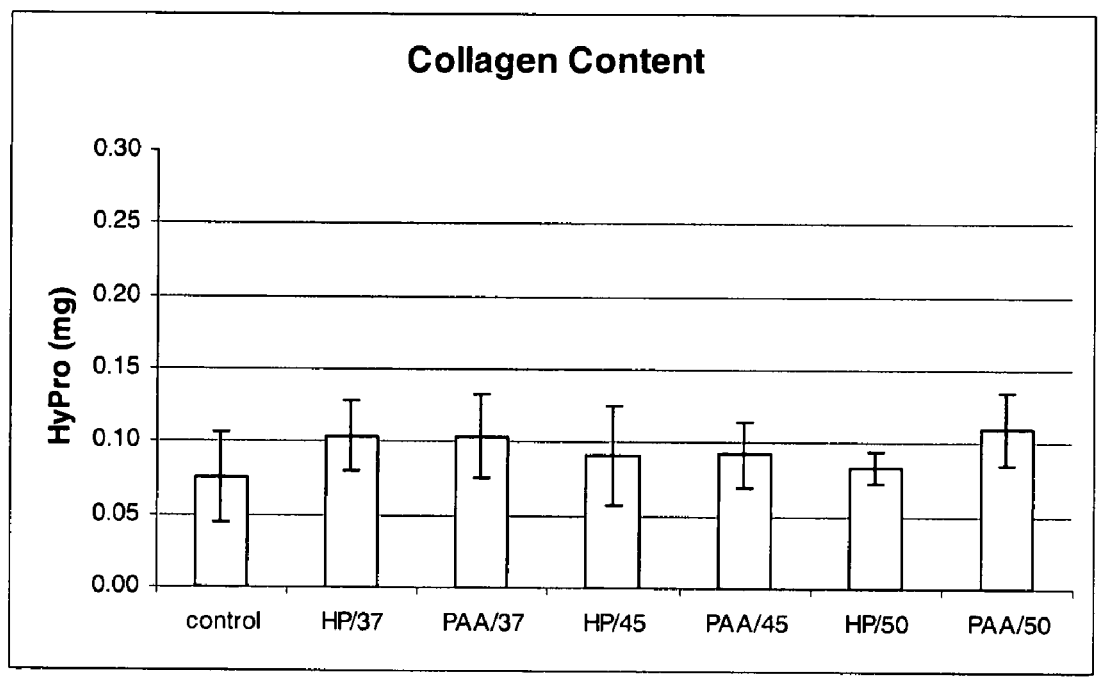
FIG. 32 is a view of samples of saphenous vein treated in 0.1% PAA or 6% HP for 60 min for a specified temperature (° C.).

It was shown that 0.1% peracetic acid is more efficient than 6% hydrogen peroxide in significantly breaking down proteins (FIG. 29 and FIG. 30). Thus the benefit is demonstrated of pretreating the tissue with peracetic acid. Without wishing to be bound by theory, it is believed that the peracetic acid opens the collagen matrix up to allow for greater penetration of the tissue. It also believed to break down the proteins better than hydrogen peroxide. FIGS. 29 and 30 show that 0.1% peracetic acid is more efficient than 6% hydrogen peroxide in significantly breaking down proteins. The Bradford Assay (Bradford, 1976) is used to quantify nonspecific proteins in collagenase digested vein samples. The Bradford Assay is a general protein assay, is based on an absorbance shift in a dye (Coomassie brilliant blue G-250 dye (CBBG)). CBBG has an absorbance shift when bound to arginine and hydrophobic amino acid residues (e.g., tryptophan, tyrosine, histidine and phenylalanine) present in protein. The reduction in antigenicity is correlated in the immunohistochemical staining (e.g., groups L and K from Example 5) and the histopathology scores (e.g., prototype recipe from Example 4). In FIG. 31 and FIG. 32, it can be seen that peracetic acid did not increase the amount of digestible hydroxyproline, therefore, leaving the collagen intact.

EXAMPLE 3

Derivation of Governing Equations

The vein wall is divided into five layers: endothelial cell monolayer, intima, internal elastic lamina (IEL), media and adventitia. Since the endothelial layer acts as an active barrier to transport it is likely to offer more resistance to flow than bulk tissue (Kenyon, 1979). The study mentioned above on rabbit aortic tissue found that removal of the endothelial cells increased the macromolecular uptake at both 70 and 160 mm Hg of applied pressure (Meyer, 1996). The resistance due to this layer will not be a factor in this study since the grafts will be deendothelialized. The layer in contact with the luminal fluid will then be the intima. The intima itself provides very little resistance to flow and it has been shown that it provides no support to matrix stress while consolidation occurs at the interior wall at the border between the intima and rigid IEL (Kenyon, 1979). When it is combined with the IEL there is a greater pressure drop ($\Delta P/L$) than seen in the media. For 70 mm Hg applied pressure in the rabbit aorta, a pressure drop of 23 mm Hg was calculated over an intimal thickness of 0.15

μm and an IEL thickness of 1.0 μm for a 20 mm Hg/μm pressure gradient compared to a pressure gradient of 0.520 mm Hg/μm for the media. Therefore, the intimal layer will be treated as a soft, liquid-like layer and will be modeled as one layer with the IEL. The IEL provides a complexity to the flow between the intima and the media since it is basically an impermeable elastin barrier containing fenestral pores with diameters ranging from 0.4 to 2.1 μm and an area fraction of 0.002 to 0.2 (aorta of rat, sheep and dog) (Tada, 2001). This layer is considered the primary resistance to flow as is evident in the literature above where accumulation of macromolecules was seen in the intima with a large drop in concentration in the media (Meyer, 1996). Although, the size of macromolecules is large compared to sodium deoxycholate, possibly resulting in a greater resistance by the IEL pores. The media will be combined with the adventitia and modeled as a porous medium containing smooth muscle cells.

There are three categories used to model arterial transport (Prosi, 2005). The simplest is the wall-free model which treats the layers as membranes with suitable boundary conditions. The solution to this model requires only a few parameters, such as, diffusivity, overall mass transfer coefficient and filtration velocity. This model cannot provide information on concentration profiles. The most complex model that accounts for each layer and their heterogeneity is the multilayer. This model provides more realistic information on the transport dynamics but requires determination of a large number of parameters for each layer. A compromise is the fluid-wall model which accounts for the venous wall but assumes it is a homogeneous layer. This is the model that is used here.

Flow through a porous media is modeled with Brinkman's equation (Tada, 2001)

$$\nabla P = \mu \Delta u_f - \frac{\mu}{K_p} u_f \quad (1)$$

$$\nabla \cdot u = 0 \quad (2)$$

where the first term is the viscous term accounting for the no-slip boundary conditions over the IEL surfaces and the smooth muscle cells and the second term is Darcy's law which characterizes flow in a porous medium away from the solid boundaries. Equation (2) is the equation of continuity (EOC) that expresses the conservation of matter assuming an incompressible fluid ($\rho u$). It has been assumed herein the viscous flow is limited to the boundary layers on the smooth muscle cells and that these boundary layers are small and decrease over time as the matrix becomes decellularized. It has also been assumed that flow is one-dimensional across the layers in the wall and the interstitial fluid and matrix are incompressible. Therefore, volume change satisfies the diffusion and reduces the flow in the venous wall to Darcy's law for filtration across the layers:

$$\frac{\partial P}{\partial x} = -\frac{\mu}{K_P} u_f \quad (3)$$

where $\mu/K_p$ is the hydraulic resistance, $K_p$ is Darcy's permeability and $u_f$ is the filtration (interstitial) velocity.

Darcy's permeability is a parameter specific to a layer. It was observed with water flux in rabbit thoracic aorta that the permeability of the intima ($K_{Pi}$) is 100-fold greater than the permeability of the media ($K_{Pm}$) (Tada, 2001). The permeability for the media is actually redefined as an effective parameter ($K_{peff}$) that accounts for the permeability of the matrix and the volume fraction of smooth muscle cells occupying the spaces between the matrix fibers. Therefore, equation (3) is rearranged to get the velocity profile of each layer as a function of the transmural pressure:

$$u_{fi} = -\frac{K_{Pi}}{\mu} \frac{\partial P}{\partial x} \quad (4)$$

$$u_f = -\frac{K_{peff}}{\mu} \frac{\partial P}{\partial x} \quad (5)$$

The interstitial velocity is typically very low on the order of $10^{-6}$ cm/s (Tada, 2001). From Wang and Tarbell (Wang, 1995) the effective permeability has the form:

$$K_{peff} = K_p \frac{1 - F - 0.305828 F^4}{1 + F - 0.305828 F^4} + O(F^6) \quad (6)$$

where F is the volume fraction of smooth muscle cell in the media. A typical value of F for aortic tissue is 0.4, reducing equation (6) to:

$$K_{p,eff} = K_p \frac{1-F}{1+F} \quad (7)$$

resulting in an effective permeability value that is 42% of the permeability of the matrix. In models of arterial wall transport, the effective permeability is assumed to be constant. Smooth muscle cells are removed from the matrix in these experiments, therefore, the effective permeability will change over time:

$$K_{p,eff} = K_p \frac{1-F(t)}{1+F(t)} \quad (8)$$

Figure 24:
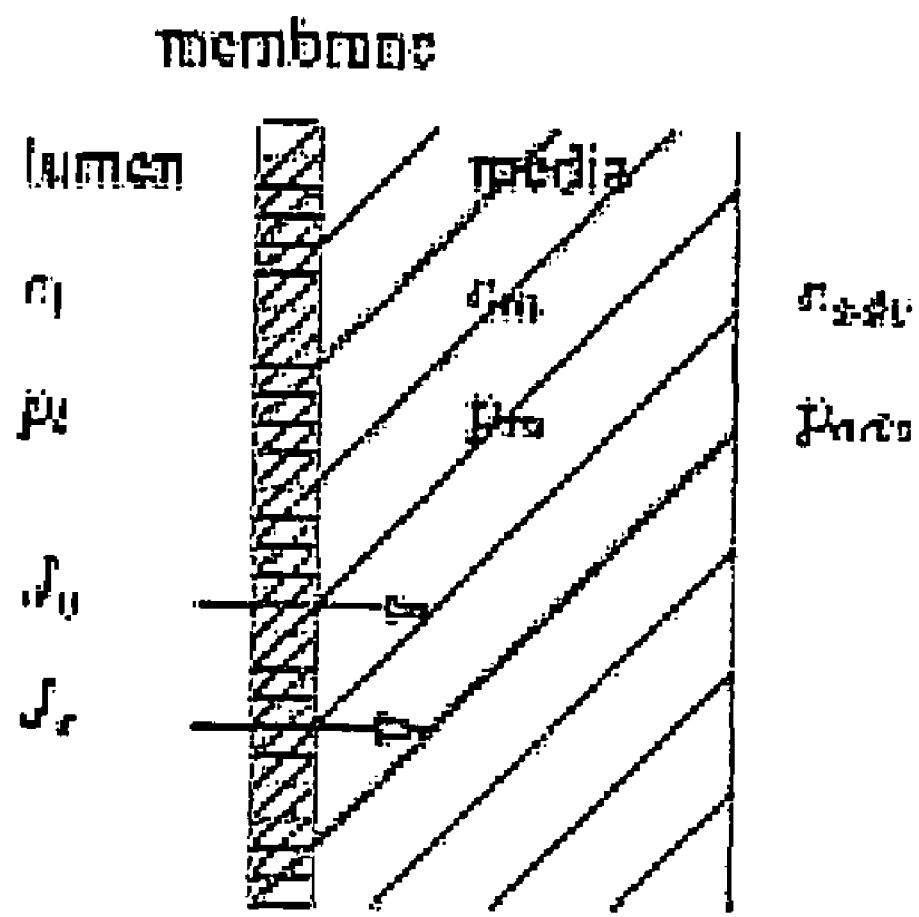
FIG. 24 is a view of the approximation of the vascular wall structure with the fluid-wall model where the subscripts i, m and adv indicate the lumen, media and adventitia, respectively. The concentration is ci and the pressure is pi (Prosi, 2005).

It is also desirable to consider the chemical dynamics through the wall which are governed by convection-diffusion equations. Mass transport occurs by an external force, such as pressure, that causes fluid motion (convection) and/or movement of a fluid from an area of higher concentration to an area of lower concentration (diffusion). The volume flux and mass flux define the transport and are coupled by the Kedem-Katchalsky equations. In the case of the fluid-wall model (FIG. 24), these equations describe the flux of fluid ($J_v$) and the flux of chemicals ($J_s$) between two solutions with different concentrations and different pressures separated by a semipermeable membrane. The flux equations are then:

$$J_v = L_{peff}(\partial p - \partial \Pi) \quad (9)$$

$$\partial \Pi = \sigma RT \partial c \quad (10)$$

$$J_s = P_{eff} \partial c + s_{eff}(c_1, c_2) J_v \quad (11)$$

where $L_{peff}$ is the hydraulic conductivity (cm/s mm Hg), $\partial \Pi$ is the osmotic pressure difference, $P_{eff}$(cm/s) is the permeability and $s_{eff}$ is the sieving coefficient. The effective parameters depend on the porosity of each medium. The sieving coefficient is an effect when the endothelial layer is present, so it will be neglected ($s_{eff}$~1). When the concentration of a single solute is high it creates a large osmotic pressure difference and contributes to solvent flow. The concentrations used in this study will be assumed to be low enough to neglect the effects of osmotic pressure.

Figure 25:
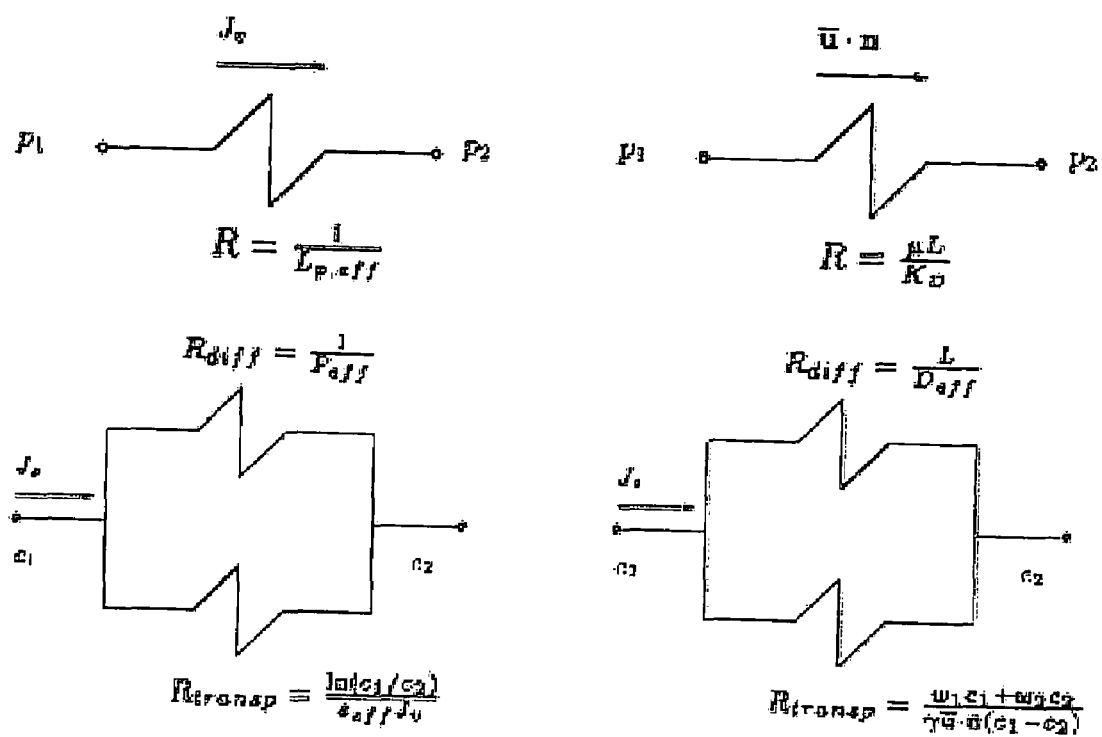
FIG. 25 is a view of the electrical analog of the filtration for the membrane (top-left) and for the wall (top-right). Electrical analog of the mass transfer processes for the membrane (bottom-left) and for the wall (bottom-right) (Prosi, 2005).
Figure 26:
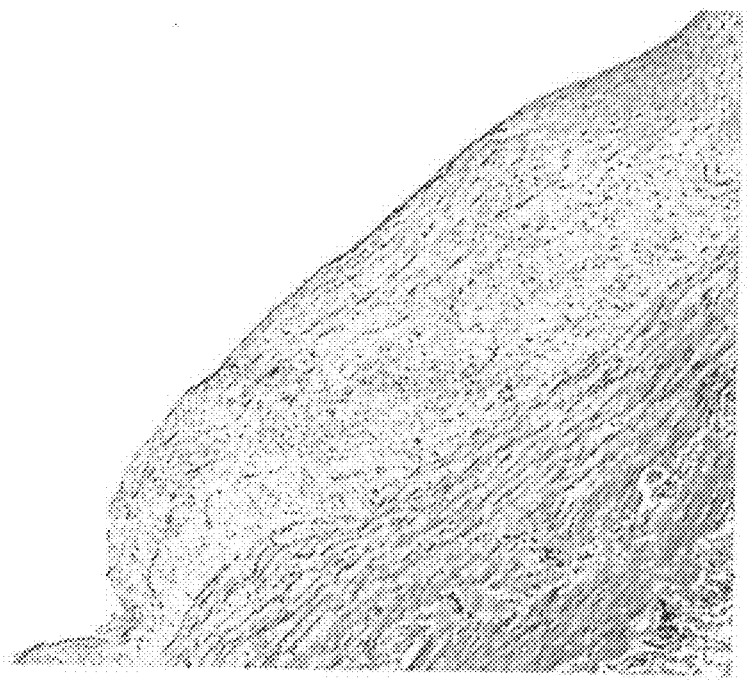
FIG. 26 is a view of histology of a vein pressurized at 100 mm Hg with 0.25% Cholate.

Equations (9) and (11) are redefined using a modified electric analogy derived by Prosi et al. (Prosi, 2005). Mass transfer is described as a potential flow due to pressure and concentration differences with parameters used to describe the resistances across the membrane (IEL) and across the porous layers in the wall (media). FIG. 25 gives a graphical representation of the electric analogy for volume and mass flux. For the volume flux across a membrane with one solute we have:

$$J_v = L_{peff}(p_1 - p_2) \tag{12}$$

and for the filtration velocity through a porous layer we have:

$$u_f \cdot n = \frac{K_{peff}}{\mu L}(p_1 - p_2) \tag{13}$$

with L as the wall thickness. Thus, the resistance to flow through the membrane is $R = 1/L_{peff}$, while the resistance in the porous layer is $R = \mu L / K_{peff}$.

The solute dynamics are driven by the concentration gradient across a membrane coupled with equation (12) and described below as:

$$J_s = P_{eff}(c_1 - c_2) + f_m(c_1, c_2)J_v \tag{14}$$

with the average concentration within the membrane, $f_m$, defined by theoretical results by Kedem and Katchalsky as:

$$f_m = \frac{(c_1 - c_2)}{\ln(c_1/c_2)} \tag{15}$$

The chemical filtrating in a porous layer in the direction normal to the layer surface is coupled with equation (13) and defined by the mass flux as:

$$J_s = \frac{D_{eff}}{L}(c_1 - c_2) + u_f \cdot nf_w(c_1, c_2) \tag{16}$$

where $f_w$ is the average concentration within the wall. The immunohistochemical stain used to determine class I MHC antigens previously was used to calculate the average concentration in the wall. It is determined digitally by subtracting the number of particles that stained red from the total number of particles and then dividing the product of the total tissue area and a unit volume with the assumption that the concentration only varies in the direction normal to the wall surface. It is also assumed that the concentration gradient is greatest within a small boundary layer with the bulk of the unstained tissue region representing the bulk concentration ($c_1$) of sodium deoxycholate.

The resistances to mass flux across a membrane and across the porous media are defined as an electrical circuit with two resistances connected in parallel (FIG. 25) and are defined as:

$$J_s = \left[\frac{D_{eff}}{L} + \frac{u_f \cdot nf_w}{(c_1 - c_2)}\right](c_1 - c_2) \tag{18}$$

$$J_s = \left[\frac{1}{R_{diff}} + \frac{1}{R_{transp}}\right](c_1 - c_2) \tag{19}$$

$$R_{tot} = \frac{R_{diff} R_{transp}}{(R_{diff} + R_{transp})} \tag{20}$$

$R_{diff}$ is the resistance to diffusion and $R_{transp}$ is the resistance associated with the transport processes (Prosi, 2005).

The effect of applied luminal pressure on the transport of a surfactant through the vein wall was investigated to achieve a more efficient, less destructive decellularization process. The surfactant sodium deoxycholate was flowed into human saphenous vein segments from cadaver tissue for one hour at varying pressures in the following manner. Human saphenous vein from a cadaver was sectioned into 50 mm segments and placed on cannulas. The cannulas were attached to a frame that suspended the tissue in an ultrasonic bath containing 0.25% sodium deoxycholate set to 37° C. The inlet cannula, determined by the direction of the vein valves, was attached to a tube inline with a pressure gage and a peristaltic pump. The outlet cannula was attached to tubing with an adjustable clamp that drained into a sink. The pump pulled sodium deoxycholate from a heated bell jar through the vein submerged in the ultrasonic bath. Pressure was monitored with the gage and adjusted by either changing the flow rate or adjusting the clamp at the end. The pressure was pulsatile with a range of ±10 mm Hg around the target applied pressure.

Figure 27:
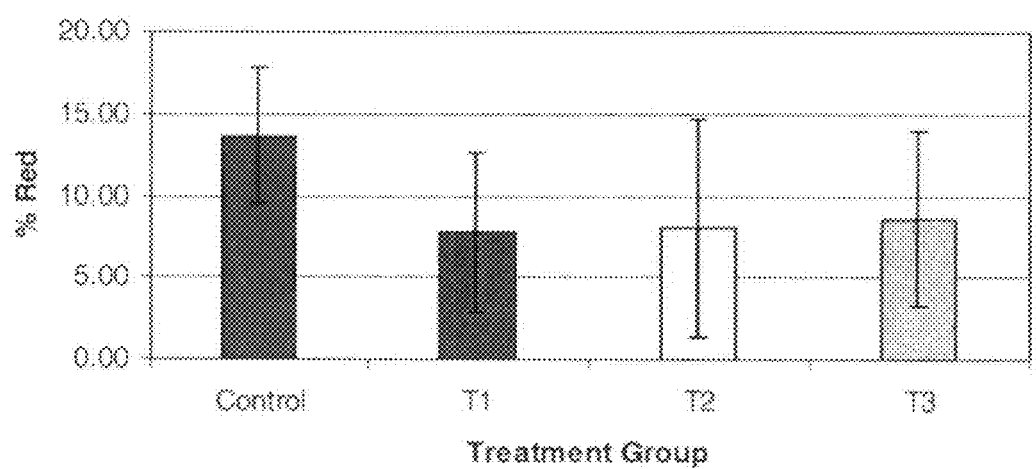
FIG. 27 is a view of the percentage of tissue stained red after treating at 0, 100 and 200 mm Hg for one to two hours at 37° C.

In the first study, there were three treatment groups with two veins per group. The first treatment group (T1) maintained an average pressure of 100 mm Hg at 37° C. for one hour. The second treatment group (T2) was pressurized at 100 mm Hg for two hours. The pressure was increased to 200 mm Hg and maintained for two hours at 37° C. for the third group (T3). A control group was treated at the same temperature for two hours with no pressure applied to the lumen (0 mm Hg). See FIG. 27.

Figures 28A, 28B:
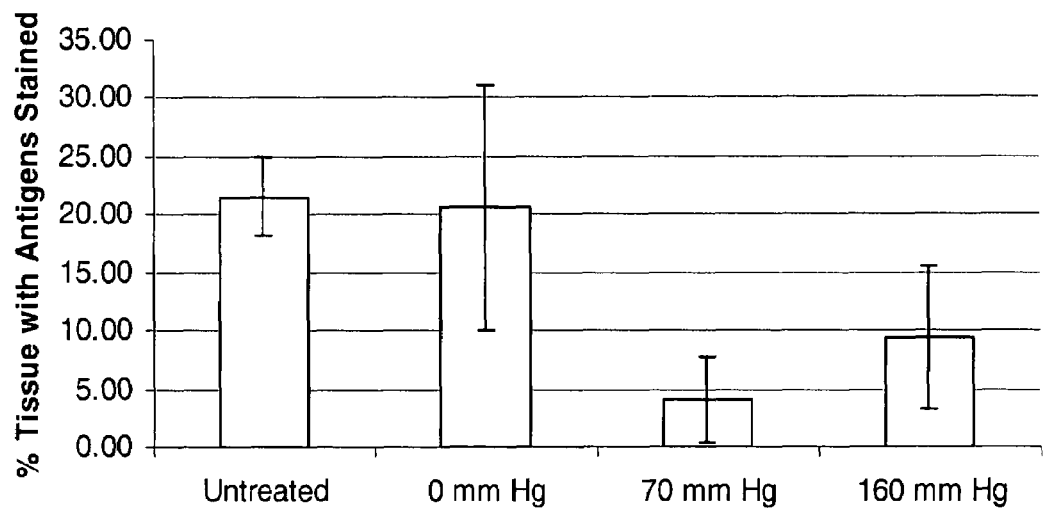
FIG. 28A is a view of the percentage of tissue stained red after treating at 0, 70 and 160 mm Hg for one to two hours at 37° C.
FIG. 28B shows the numerical values associated with FIG. 28A.

In a second study, there were four treatment groups: untreated, 0 mm Hg, 70 mm Hg and 160 mm Hg with 5, 3, 6 and 6 veins in each group, respectively. Veins were pressurized at 37° C. for two hours. See FIGS. 28A & 28B. This study had a pressure tolerance of ±4 mm Hg.

Following each treatment, the veins were flushed at the same pressure for 10 min. Each vein was sectioned into three segments for histology and three segments for immunohistochemical staining for class I MHC antigens.

Histology:

Samples were placed in 10% buffered formalin immediately following the rinse step and remained there for at least 24 hours before further preparation. Then, the samples were embedded in paraffin and stained with hematoxylin and eosin (H&E) to determine.

Immunohistochemistry:

Immunohistochemistry was used to determine the level of antigens remaining in the tissue after treatment as a function of pressure and time. Class I MHC antibodies were used for evaluation since class I antigens are present in a much greater abundance than class II antigens. Samples were prepared in frozen blocks and sectioned with a cryostat. The sections were thawed and then rinsed for blocking and antibody staining. Sections were incubated for 30 minutes in primary antibody (mouse anti-HLA-ABC class I MHC) solution and then for another 30 minutes in diluted biotinylated secondary antibody (Vector ABC Elite kit) solution. An enzyme substrate, NovaRed (Vector), was used to stain the antibodies red. The counter stain was hematoxylin providing a blue contrast.

Optical Evaluation:

A Zeiss Axiophot 2 microscope with a motorized Ludl scanning stage was used for tile field mapping at 5× to capture the entire image in one frame. Particle analysis was performed in Image J to determine the ratio of antigen staining (red) to the total tissue sample.

Results:

Experimental results demonstrate the finding that an increase in transmural pressure induces stretching of the matrix allowing for an interstitial volume change increasing mass transport of water, macromolecules and microspheres. Both studies demonstrated an increase in macromolecule flux across the rat aortic wall when pressure increased up to about 70-100 mm Hg, but a negligible difference was observed with elevated pressures of 160 mm Hg or 200 mm Hg. Pressure-induced vector transport in human saphenous veins showed a two-fold increase in microsphere area within the wall, but the area in the media was only 0.1% greater. At maximum distension transportation becomes limited, and a further increase in pressure may influence the fluid flux and may even restrict flow due to compaction. Thus there is a point of maximum distension where the concentration of the chemical in the tissue plateaus off and no increase in pressure will enhance the decellularization efficiency (due to compaction of the tissue). This point of maximum distension is at about 120 mm Hg for the samples studied.

A significant reduction in antigens was observed at pressures above 0 mm Hg and compaction occurred above about 120 mm Hg. DNA staining was still visible on the luminal surfaces as well as within the matrix for all groups. Even so, there was a reduction in the amount of red stained tissue in all treatment groups compared to the control group. In the first study, an increase in time from one hour to two hours at 100 mm Hg or an increase in pressure to 200 mm Hg did not significantly reduce the mean amount of antigens detected. In the second study, a similar effect was observed, with greatest antigen reduction at a pressure of 70 mm Hg and no increase at the higher pressure point (160 mm Hg).

Suitable pressure gradients for use in the present processes include, but are not limited to, pressure gradients in the range of from about 25 mm Hg to about 1000 mm Hg, preferably about 50 mm Hg to about 500 mm Hg, preferably about 100 mm Hg to about 400 mm Hg, more preferably from about 70 mm Hg to about 300 mm Hg. The pressure gradient can be less than 2300 mm Hg, alternatively less than 1654 mm Hg, alternatively less than 1200 mm Hg, alternatively less than about 200 mm Hg, alternatively less than about 120 mm Hg.

However, the endothelial cells that were still present on the tissue could have provided a barrier that was resistant to flow; removal of these cells could increase the efficiency of this process. Thus, removal of some or all of the endothelial cells prior to processing is also another aspect of the present invention.

EXAMPLE 4

An in-vivo study in rats was conducted. Human saphenous vein was prepared for intramuscular implantation into Sprague Dawley rats. The implants were 10 mm in length, cut longitudinally and either untreated or treated by one of the methods described below. The specified chemicals for each treatment group was sterile filtered. After each process, the tissue was rinsed in excess sterile PBS for one hour. The implant treatment groups are as follows:

A: Control: Untreated human saphenous vein (Aseptic—untreated)

B: Sodium deoxycholate (0.25% at 37° C. for 24 hours)

C: Sodium deoxycholate (0.25% at 37° C. for 24 hours); Trypsin (1.0% at 37° C. for 6 hours)

D: Sodium deoxycholate (0.25% at 37° C. for 24 hours); Trypsin (1.0% at 37° C. for 6 hours); Gluteraldehyde (0.0025% at 4° C. or room temperature for 24 hours); L-Arginine (neutralize—1 mM at room temperature for 1 hr)

E: Sodium deoxycholate (0.25% at 37° C. for 24 hours); Heat treated (PBS at 100° C. for 10 min). Data not shown.***

F: Sodium deoxycholate (0.25% at 37° C. for 24 hours); Heat treated (PBS at 100° C. for 10 min)→Trypsin (1.0% at 37° C. for 6 hours). Data not shown.***

***Groups E and F were included in this animal study to investigate the importance of collagen integrity for saphenous vein grafts. Group E showed massive calcification while group F was completely resorbed within the six week study period (data not shown).

G: Prototype recipe: 1% Triton 40° C. 20 min; 6% HP (hydrogen peroxide) 40° C. 20 min; 0.25% Cholate/1% Triton 40° C. 2 hrs; 0.1% PAA 40° C. 1 hr; PBS 40° C. 10 min (5×'s rinsing). PBS rinses also occur between each chemical step.

| Treatment | N |
|---|---|
| A. Aseptic-untreated | 4 |
| B. Cholate | 4 |
| C. Cholate-Trypsin | 4 |
| D. Cholate-Trypsin-Gluteraldehyde | 4 |
| E. Cholate-Heat | 4 |
| F. Cholate-Heat-Trypsin | 4 |
| G. Prototype Recipe | 4 |

Four implants from each group go into one rat for a total of 7 rats and 28 implant sites. An eighth rat is injected in four sites with decreasing concentrations of sodium deoxycholate (0.25%, 0.1%, 0.01%, 0.001%) to measure the biocompatibility of the detergent. No response was noted at any of these concentrations at 6 weeks after surgery.

Preimplant evaluation methods include immunohistochemical staining to measure the level of decellularization, collagen degradation assay (separate samples), and 14-day cell culture for any possible contamination during processing. Postimplant evaluation includes hematoxylin-eosin staining for immune cells, fibroblasts and extracellular matrix integrity as well as a calcium stain. The histology slides were examined by an external pathologist. Note: Sample F was completely resorbed therefore the explanted vein was unavailable for analysis.

Figure 33:
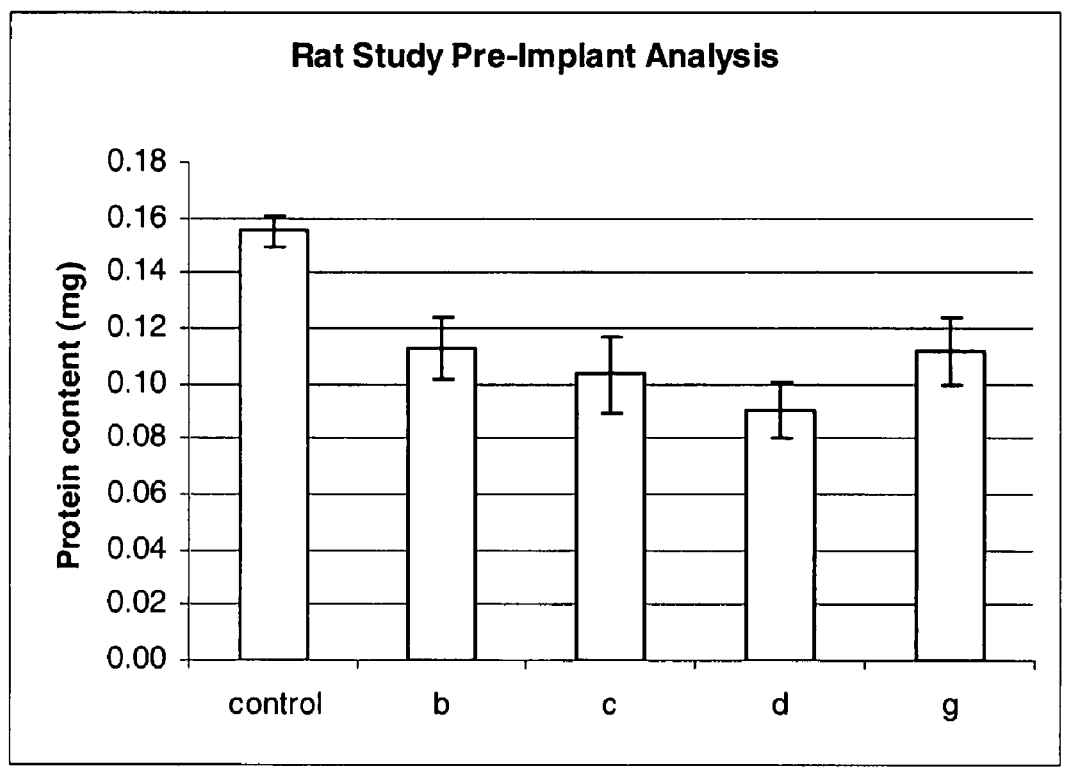
FIG. 33 is a view of the amount of residual class I MHC within the human saphenous vein segments prior to surgery.

Pre-Implantation Analysis:

FIG. 33 shows the reduction in non-specific proteins with the different treatment groups before implantation in the rat. This reduction in proteins is correlated with the reduction in the immune response since the antigens are contained on the protein structures of the cells.

Figure 34:
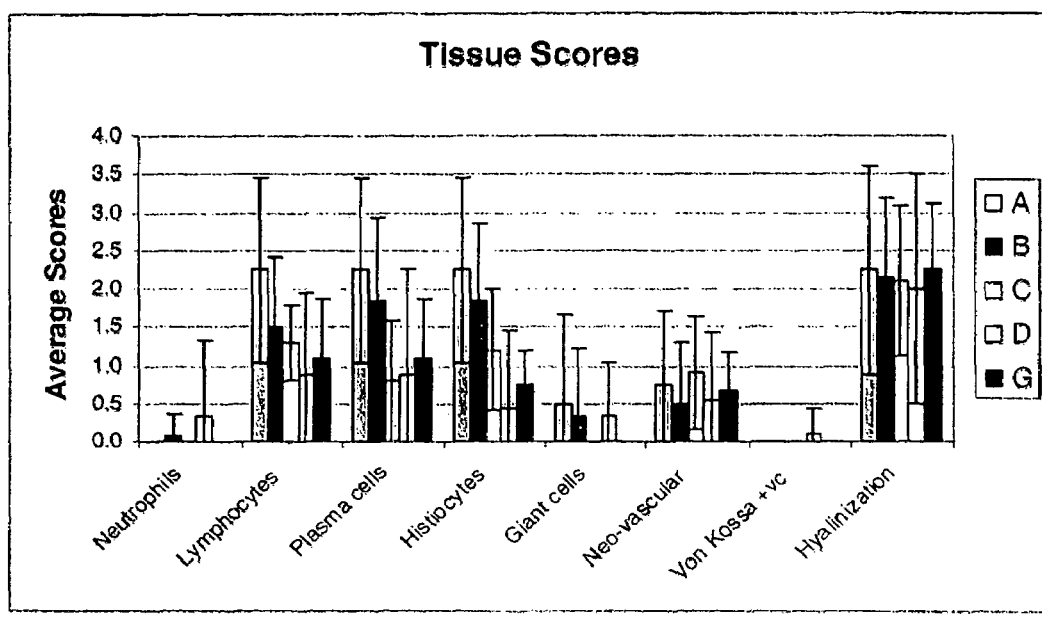
FIG. 34 is a view of the overall histopathology scores by cell type for the tissue from the rat study.
Figure 35:
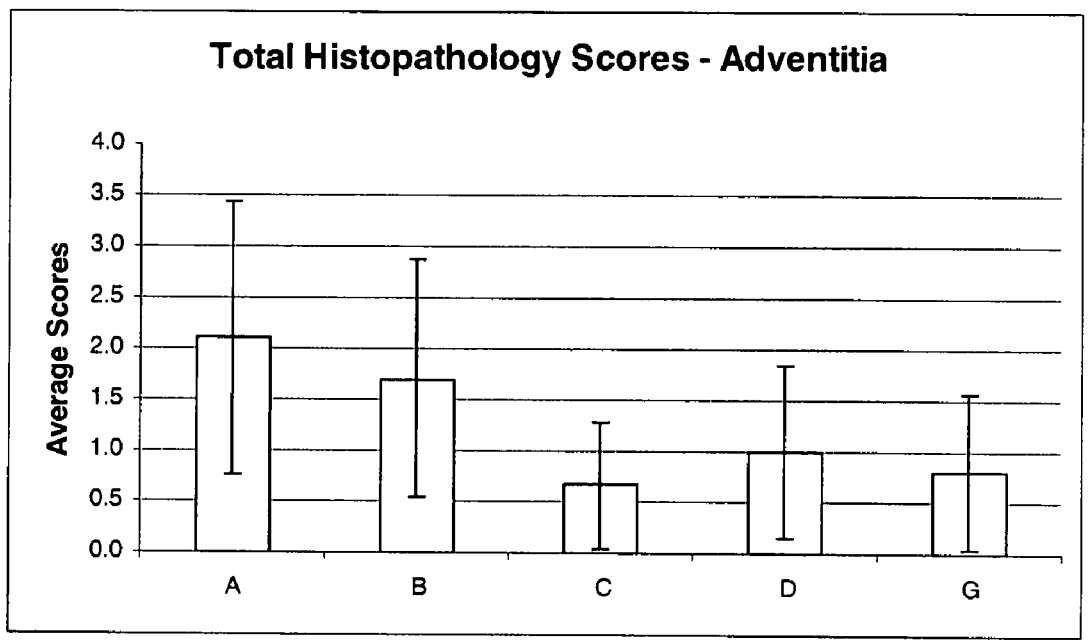
FIG. 35 is a view of the histopathology scores for the adventitia from the rat study.
Figure 36:
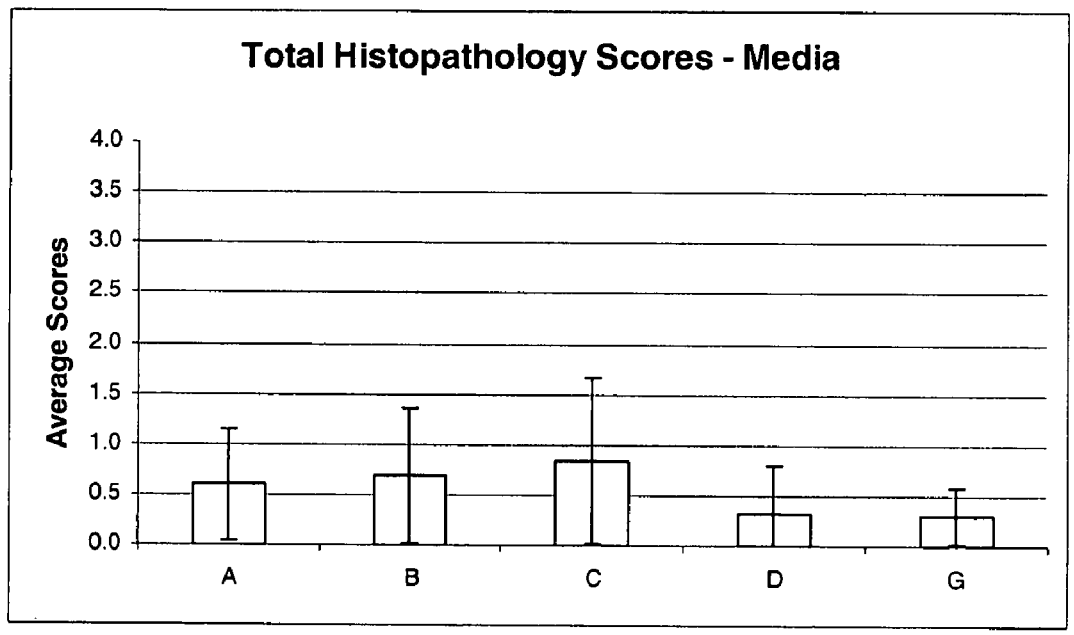
FIG. 36 is a view of the histopathology scores for the media from the rat study.
Figure 37:
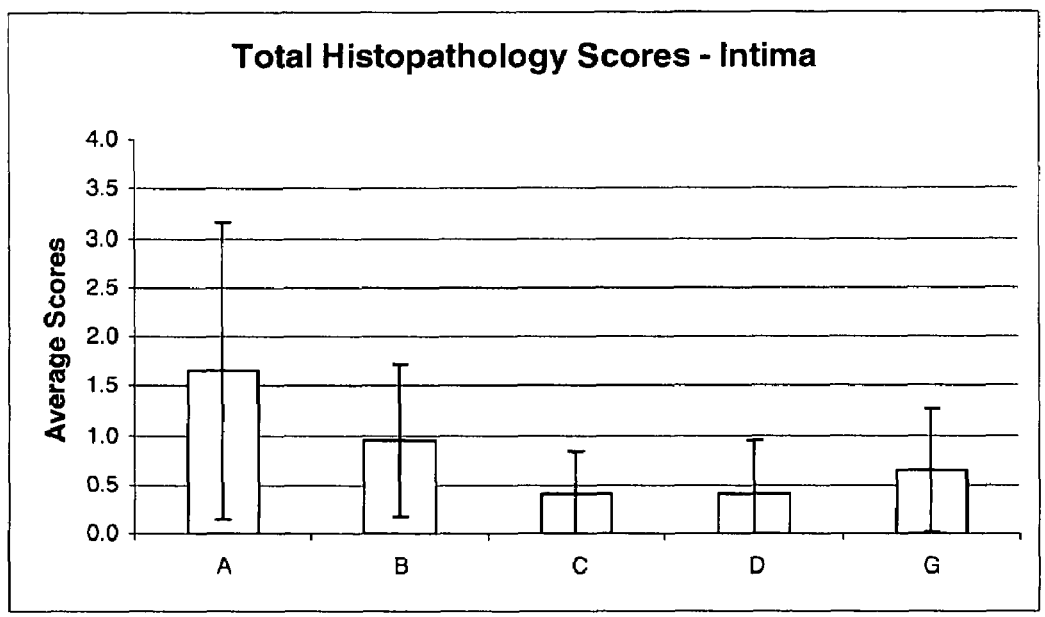
FIG. 37 is a view of the histopathology scores for the intima from the rat study.
Figure 38:
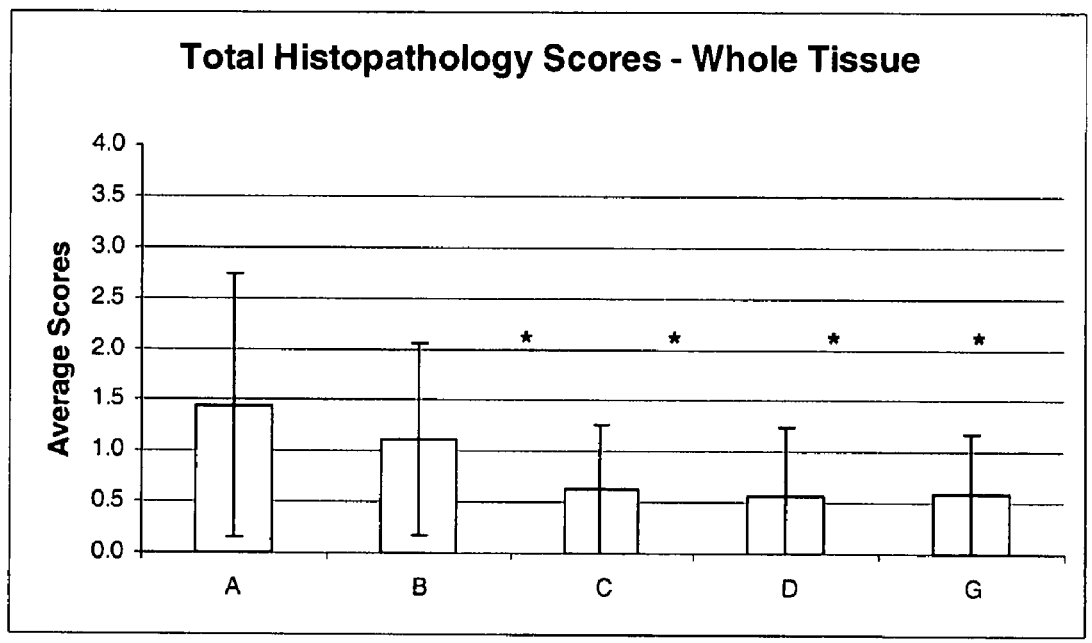
FIG. 38 is a view of the histopathology scores for the whole tissue from the rat study. Asterisks indicate significance.
Figure 39:
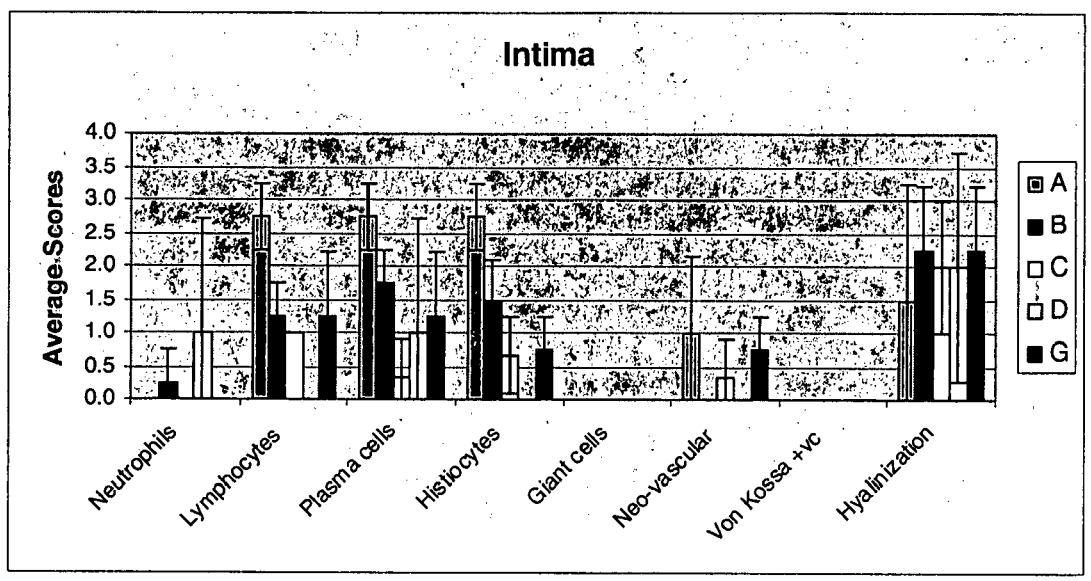
FIG. 39 is a view of the histopathology scores for the intima from the rat study by cell type. A is significantly more reactive than C and G; B is significantly more reactive than C and G.
Figure 40:
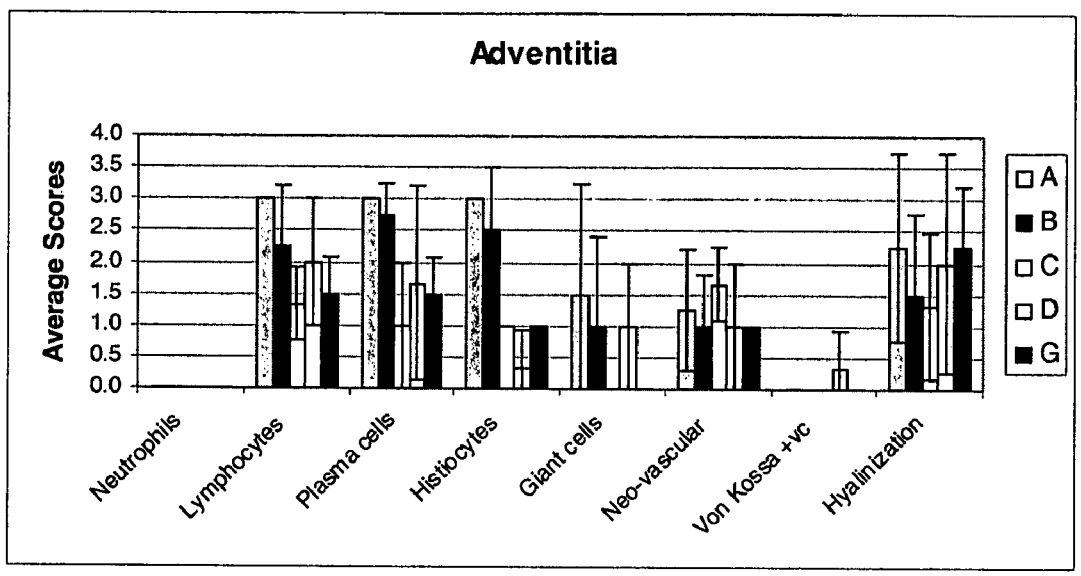
FIG. 40 is a view of the histopathology scores for the adventitia from the rat study by cell type. A is significantly more reactive than all groups.

Histopathology Results:

FIG. 34 shows the average histopathology scores for the entire tissue segment for each group. FIG. 38 shows the results for whole tissue. The scores were evaluated for the intima, media and adventitia. FIGS. 35-37 show the average scores in each layer for each treatment group (n=4). FIGS. 39 and 40 show the specific immune cells that were present and to what extent as well as calcification (von Kossa) in the adventitia and intima. The media showed no significant difference between groups (data not shown). This is most likely due to the fact that it was the only layer that was not in direct contact with the immune system of the rat. The adventitia showed the greatest response followed by the media with the intima revealing the lowest response for treated groups. FIG. 34 also shows mild calcification in only one sample in group D.

EXAMPLE 5

Samples were tested to determine effect of chemical order in recipes. Samples of human saphenous vein were treated first in chemical 1 for a specified time and then in chemical 2 for a specified time as indicated in the chart below. The samples were analyzed for class I MHC antigens with immunohistochemical staining. Groups A, B, K and L were completely removed of class I MHC antigens. Group F was almost significantly removed of antigen material when compare to the controls. Groups K, L and F preceded the surfactant treatment with peracetic acid. Without wishing to be bound by theory, it is believed that acid causes collagen to swell, thereby, allowing the surfactant to penetrate the tissue and remove the debris. It is also believed that peracetic acid breaks down the proteins (see, e.g. protein assay in collagen results) contained within the tissue, thus, assisting in the removal of antigenic debris.

Figure 41:
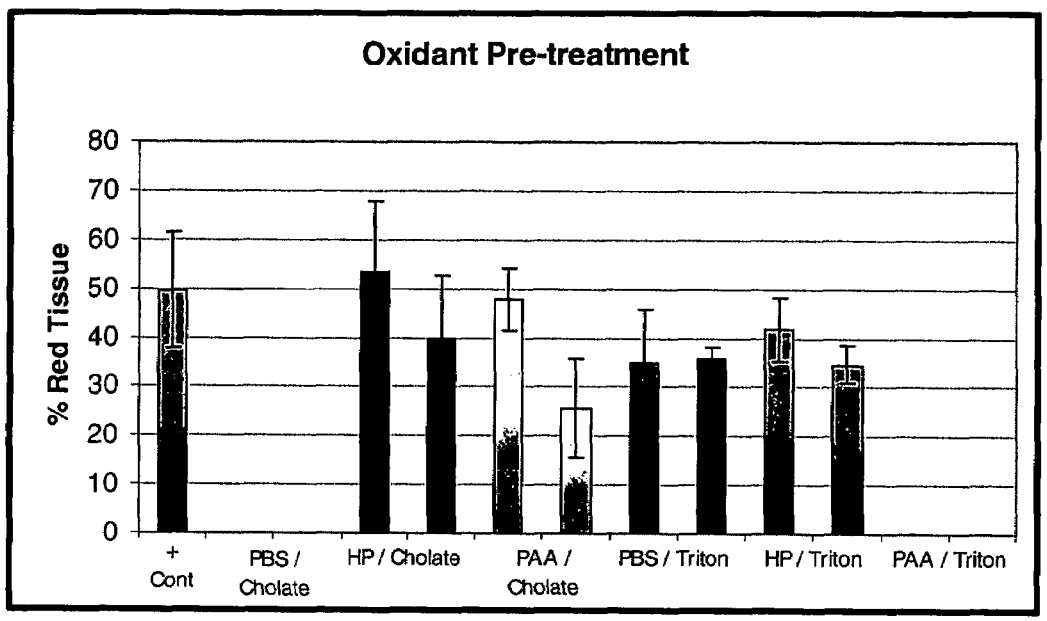
FIG. 41 is a view of samples treated to determine effects of chemical order. Samples were first treated either in PBS, HP or PAA. Then, the samples were treated in either sodium deoxycholate or Triton X-100. The first bar in each group (except control) was treated for 30 min in the first solution and then for one hour in the second treatment. The second bar in each group (except control) was treated for 1 hour in the first solution and then for three hours in the second treatment.

The results from this study show that decellularizing with Triton X-100 is improved when first treating the tissue with peracetic acid. This was important in reducing the immunogenicity and inflammation in the prototype recipe in the rat study (Example 4). Results are shown in FIG. 41.

Treatment Groups:

| Label | 1$^{st}$ Chemical | Time (min) | 2$^{nd}$ Chemical | Time (min) |
|---|---|---|---|---|
| A | PBS | 30 | Cholate | 30 |
| B | PBS | 60 | Cholate | 60 |
| C | HP | 30 | Cholate | 30 |
| D | HP | 60 | Cholate | 60 |
| E | PAA | 30 | Cholate | 30 |
| F | PAA | 60 | Cholate | 60 |
| G | PBS | 30 | Triton | 30 |
| H | PBS | 60 | Triton | 60 |
| I | HP | 30 | Triton | 30 |
| J | HP | 60 | Triton | 60 |
| K | PAA | 30 | Triton | 30 |
| L | PAA | 60 | Triton | 60 |

In all of the foregoing processes, the vascular graft can optionally be contacted with a cleaning agent (e.g., a detergent, enzyme, alcohol, oxidizing sterilant, or other cleaning agent) at a temperature less than about 60° C., alternatively less than about 59° C., alternatively less than about 58° C., alternatively less than about 57° C., alternatively less than about 56° C., alternatively less than about 55° C., alternatively less than about 54° C., alternatively less than about 53° C., alternatively less than about 52° C., alternatively less than about 51° C., alternatively less than about 50° C., alternatively less than about 49° C., alternatively less than about 48° C., alternatively less than about 47° C., alternatively less than about 46° C., alternatively less than about 45° C., alternatively less than about 44° C., alternatively less than about 43° C., alternatively less than about 42° C., alternatively less than about 41° C., alternatively less than about 40° C., alternatively less than about 39° C., alternatively less than about 38° C., alternatively less than about 37° C., alternatively less than about 36° C. The vascular graft can be contacted with a cleaning agent (e.g., a detergent, enzyme, alcohol, oxidizing sterilant, or other cleaning agent) at a temperature greater than about 35° C., alternatively greater than about 36° C., alternatively greater than about 37° C., alternatively greater than about 38° C., alternatively greater than about 39° C., alternatively greater than about 40° C., alternatively greater than about 41° C., alternatively greater than about 42° C., alternatively greater than about 43° C., alternatively greater than about 44° C., alternatively greater than about 45° C., alternatively greater than about 46° C., alternatively greater than about 47° C., alternatively greater than about 48° C., alternatively greater than about 49° C. In some embodiments, it may be desirable to contact a vascular graft with a cleaning agent at a higher or lower temperature. Any minimum temperature and any maximum temperature, as specified above, may be combined to define a range, providing that the minimum selected is equal to or less than the maximum selected. For example, the vascular graft can be contacted with a cleaning agent at a temperature in the range of from about 44° C. to about 48° C.

In all of the foregoing processes, the vascular graft can optionally be contacted with a solution containing a cleaning agent (e.g., a detergent, enzyme, alcohol, oxidizing sterilant, or other cleaning agent) at a desired concentration. For example, the concentration of one or more of the cleaning agents in a solution can be at least about 0.01% (w/v), alternatively at least about 0.025% (w/v), alternatively at least about 0.05% (w/v), alternatively at least about 0.1% (w/v), alternatively at least about 0.25% (w/v), alternatively at least about 0.5% (w/v), alternatively at least about 0.75% (w/v), alternatively at least about 0.9% (w/v), alternatively at least about 1% (w/v), alternatively at least about 1.25% (w/v), alternatively at least about 1.5% (w/v), alternatively at least about 1.75% (w/v), alternatively at least about 2% (w/v), alternatively at least about 2.5% (w/v), alternatively at least about 3% (w/v), alternatively at least about 4% (w/v), alternatively at least about 5% (w/v), alternatively at least about 6% (w/v), alternatively a higher concentration(s) of cleaning agent(s).

All patents, test procedures, and other documents cited herein, including priority documents, are fully incorporated by reference to the extent such disclosure is not inconsistent with this invention and for all jurisdictions in which such incorporation is permitted.

While the present invention has been described and illustrated by reference to particular embodiments, it will be appreciated by those of ordinary skill in the art that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

LIST OF REFERENCES

1. Conte, M. S., *The ideal small arterial substitute: a search for the Holy Grail?* Faseb J, 1998. 12(1): p. 43-5.

2. Conklin, B. S., et al., *Development and evaluation of a novel decellularized vascular xenograft.* Med Eng Phys, 2002. 24(3): p. 173-83.
3. DeMasi, R. J. and S. O. Snyder, *The current status of prosthetic-vein composite grafts for lower extremity revascularization.* Surg Clin North Am, 1995. 75(4): p. 741-52.
4. Stillman, R. M., *Excerpt from infrainguinal occlusive disease,* eMedicine.
5. Prager, M., Holzenbein, T., Aslim, E., Domenig, C., Muhlbacher, F., Kretschmer, G., *Fresh arterial homograft transplantation: a novel concept for critical limb ischemia.* Eur J Vasc Endovasc Surg, 2002. 24: p. 314-321.
6. Timaran, C., Goldman, M H, *Saphenous vein allografts for infrainguinal arterial reconstruction: current role as vascular conduits.* Adv Vasc Surg, 2002. 10: p. 183-197.
7. Bader, A., et al., *Engineering of human vascular aortic tissue based on a xenogeneic starter matrix.* Transplantation, 2000. 70(1): p. 7-14.
8. Kainer, M., *EIS Officer.* 2002, CDC and Prevention: Atlanta, Ga.
9. Administration, U.S.F.a.D., *Human Cells, Tissues, and Cellular and Tissue-Based Products.* 2004.
10. Bastounis, E., et al., *PTFE-vein composite grafts for critical limb ischaemia: a valuable alternative to all-autogenous infrageniculate reconstructions.* Eur J Vasc Endovasc Surg, 1999. 18(2): p. 127-32.
11. Benedetti-Valentini, F., Gossetti, B., Irace, I., Martinelli, O., Gattuso, R., *Composite grafts for critical limb ischemia.* Cardio Vasc Surg, 1996. 4(3): p. 372-376.
12. DeLaurentis, D., Freidmann, P, *Arterial reconstruction about and below the knee: another look.* Am J Surg, 1971. 121(April): p. 392-397.
13. Lord, J. W., Jr., et al., *New technique for construction of coposite Dacron vein grafts for femoro-distal popliteal bypass in the severely ischemic leg.* Ann Surg, 1975. 181 (5): p. 670-5.
14. Oppat, W. F., et al., *Natural history of composite sequential bypass: ten years' experience.* Arch Surg, 1999. 134 (7): p. 754-7; discussion 757-8.
15. Lin, P., Bush, R L, Weiss, V J, Lumsden, A B, *Vascular access: the utility of cryopreserved vein allograft.* Adv Vasc Surg, 2001. 9: p. 109-119.
16. Insight, M., *Safer SVG Interventions,* in *Medtech Insight.* 2001. p. 256-7.
17. Mizell, J., B. Maglish, and R. Matheny, *Minimally Invasive Direct Coronary Artery Bypass Graft Surgery: An Introduction for Critical Care Nurses.* Critical Care Nurse, 1997. 17(3).
18. CryoLife, *Vascular Tissue—CryoVein.* 2002.
19. *Dorland's medical dictionary.* 25th ed. 1995, Philadelphia: W. B. Saunders Company.
20. Linton, R. R., Wirthlin, L. S., *Femoropopliteal composite Dacron and autogenous vein bypass grafts.* Arch Surg, 1973. 107: p. 748-753.
21. Promotion, N.C.f.C.D.P.a.H., 1999 *Diabetes Surveillance Report.* 1999, Centers for Disease Control and Prevention.
22. Promotion, N.C.f.C.D.P.a.H., *Diabetes: Disabling, Deadly, and on the Rise.* 2002, Centers for Disease Control and Prevention.
23. Clark, D., *Enduring and Cost Effective Limb Salvage.* 1998, Hyperbaric Medicine Update.
24. Alexander, J. J., Wells, K. E., Yuhas, J. P., Piotrowski, J. J., *The role of composite sequential bypass in the treatment of multilevel infrainquinal arterial occlusive disease.* Am J Surg, 1996. 172: p. 118-122.
25. Castier, Y., et al., *Early experience with cryopreserved arterial allografts in below-knee revascularization for limb salvage.* Am J Surg, 1999. 177(3): p. 197-202.
26. Faries, P. L., LoGerfo, F. W., Arora, S., Pulling, M. C., Rohan, D. I., Akbari, C. M., Campbell, D. R., Gibbons, G. W., Pomposelli, F. B., *Arm vein conduit is superior to composite prosthetic-autogenous grafts in lower extremity revasculariztion.* J Vasc Surg, 2000. 31(6): p. 1119-1126.
27. Londrey, G. L., Ramsey, D. E., Hodgson, K. J., Barkmeier, L. D., Sumner, D. S., *Infrapopliteal bypass for severe ischemia: comparison of autogenous vein, composite, and prosthetic grafts.* J Vasc Surg, May 1991. 13(5): p. 631-636.
28. Fung, Y. C., *Biomechanics: Mechanical properties of living tissues.* 2 ed. 1993, New York: Springer-Verlag.
29. Martini, F. H., *Fundamentals of anatomy and physiology.* Fifth ed. 2001, Upper Saddle River, N.J.: Prentice-Hall, Inc.
30. Fung, Y. C. and S. Q. Liu, *Determination of the mechanical properties of the different layers of blood vessels in vivo.* Proc Natl Acad Sci U S A, 1995. 92(6): p. 2169-73.
31. McClurken, M., Lipson, D., *Collagen shrinkage and vessel sealing.* 2001 TissueLink Medical, Inc.: Dover.
32. DeWeese, J. A., *Autogenous venous bypass grafts—still the standard.* Cardiovasc Surg, 1994. 2(2): p. 180-6.
33. Gupta, B. S., Kasyanov, V. A., *Biomechanics of human common carotid artery and design of novel hybrid textile compliant vascular grafts.* J Biomed Mater Res., 1997. 34(3): p. 341-349.
34. Gabriel, M., Kostrzewa, A., Sobieska, M., *Immune response after cryopreserved aortic allograft replacement for major vascular infection.* Transplant Proceedings, 2002.34: p. 713-714.
35. *Patient Information Intro,* CryoLife.
36. *Standards for Tissue Banking,* ed. J. E. Woll, Kasprisin, D. 2001, American Association of Tissue Banks.
37. Almond, C. H., et al., *Aortic homograft preservation with dimethyl sulfoxide.* Arch Surg, 1966. 93(4): p. 656-658.
38. Beach, P. M., et al., *Aortic valve replacement with frozen irradiated homografts.* Circulation, 1972. 45(supp I): p. 29-35.
39. Bolooki, H., et al., *A simple method of aortic homograft valve sterilization and preservation.* J Thorac Cardiovasc Surg, 1972. 63(2): p. 249-257.
40. Bowman, F. O., et al., *Further evaluation of aortic valve homografts sterilized by electron-beam energy.* Circulation, 1969. 39(supp I): p. 57-60.
41. Innes, B. J., et al., *Effect of sterilization methods on endothelium of homograft and heterograft valves.* J Surg Res, 1971. 11(3): p. 111-118.
42. Control, C.f.D., *Update: allograft-associated bacterial infections—United States.* MMWR Weekly Report, 2002. 51: p. 207-210.
43. Administratin, F.a.D., *Good Laboratory Practices (GLP) for non-clinical laboratory studies* 21 CFR Part 58. p. Supporting Statement.
44. Alexander, K., *Cadaveric Cardiovascular Tissue Disinfection Performance Qualification.* 2004, AppTec: Marietta, Ga.
45. Waterworth, P. M., et al., *A critical investigation into the antibiotic sterilization of heart valve homografts.* Thorax, 1974. 29: p. 432-436.
46. *Septic arthritis following anterior cruciate ligament reconstruction using tendon allograft—Florida and Louisiana,* 2000. MMWR Weekly, 2001. 50(48): p. 1081-3.

47. *Hepatitis C virus transmission from an antibody_negative organ and tissue donor_United States, 2000-2002.* MMWR Weekly, 2003. 52(13): p. 273-276.
48. *Invasive Streptococcus pyogenes after allograft implantation—Colorado,* 2003. MMWR Weekly, 2003. 52(48): p. 1173-1176.
49. Reller, L. B., et al., *Bacterial endocarditis caused by Oerskovia turbata.* 1975. 83(5): p. 664-666.
50. Silver, M. D., P. G. Tuffnell, and W. G. Bigelow, *Endocarditis caused by Paecilomyces varioti affecting an aortic valve allograft.* J Thorac Cardiovasc Surg, 1971. 61(2): p. 278-281.
51. Pukacki, F., et al., *The mechanical properties of fresh and cryopreserved arterial homografts.* Eur J Vasc Endovasc Surg, 2000. 20(1): p. 21-4.
52. Bellon, J. M., et al., *Arterial damage induced by cryopreservation is irreversible following organ culture.* Eur J Vasc Endovasc Surg, 1999. 17(2): p. 136-43.
53. Faggioli, G. L., et al., *Long-term cryopreservation of autologous veins in rabbits.* Cardiovasc Surg, 1994. 2(2): p. 259-65.
54. Galambos, B., et al., *Preservation of vein allograft viability during long-term storage.* Eur Surg Res, 2005. 37(1): p. 60-7.
55. Pascual, G., et al., *Effect of the thawing process on cryopreserved arteries.* Ann Vasc Surg, 2001. 15(6): p. 619-27.
56. Ruddle, A. C., et al., *Venous allografts prepared from stripped long saphenous vein. Is there a need for antibiotic sterilisation?* Eur J Vasc Endovasc Surg, 1998. 15(5): p. 444-8.
57. Lin, P. H., Brinkman, W. T., Terramani, T. T., Lumsden, A. B., *Management of infected hemodialysis access grafts using cryopreserved human vein allografts.* Am J Surg, 2002. 184: p. 31-36.
58. Mirelli, M., Stella, A., Faggioli, G. L., Scolari, M. P., Iannelli, S., Freyrie, A., Buscaroli, A., De Santis, L., Resta, F., Bonomini, V., D'Addato, M., *Immune response following fresh arterial homograft replacement for aortoiliac graft infection.* Eur J Vasc Endovasc Surg, 1999. 18: p. 424-429.
59. Silverstein, R. L., *The Vascular Endothelium, in Inflammation: Basic Principles and Clinical Correlates,* J. I. G. a. R. Snyderman, Editor. 1999, Lippincott Williams & Wilkins: Philadelphia. p. 207-225.
60. Allaire, E., et al., *Cell-free arterial grafts: morphologic characteristics of aortic isografts, allografts, and xenografts in rats.* J Vasc Surg, 1994. 19(3): p. 446-56.
61. Davies, M. G., et al., *Functional and histological differences in autogenous and allogenic vein grafts: two different vasculopathies?* J Surg Res, 1997. 69(1): p. 14-22.
62. Ketchedjian, A., et al., *Recellularization of decellularized allograft scaffolds in ovine great vessel reconstructions.* Ann Thorac Surg, 2005. 79(3): p. 888-96; discussion 896.
63. Wilson, G. J., et al., *Acellular matrix: a biomaterials approach for coronary artery bypass and heart valve replacement.* Ann Thorac Surg, 1995. 60(2 Suppl): p. S353-8.
64. Posner, M. P., et al., *Early results of infrageniculate arterial reconstruction using cryopreserved homograft saphenous conduit (CADVEIN) and combination low-dose systemic immunosuppression.* 1996. 183(3): p. 208-216.
65. Madden, R., et al., *Decellularized cadaver vein allografts used for hemodialysis access do not cause allosensitization or preclude kidney transplantation.* Am J Kidney Dis, 2002. 40(6): p. 1240-3.
66. Hawkins, J. A., et al., *Class I and class II anti-HLA antibodies after implantation of cryopreserved allograft material in pediatric patients.* J Thorac Cardiovasc Surg, 2000. 119(2): p. 324-330.
67. *End-stage kidney disease,* MedlinePlus. p. Medical dictionary.
68. Hawkins, J. A., et al., *Immunogenicity of decellularized cryopreserved allografts in pediatric cardiac surgery: comparison with standard cryopreserved allografts.* J Thorac Cardiovasc Surg, 2003. 126(1): p. 247-52; discussion 252-3.
69. Girauss, R. W., et al., *Decellularization of rat aortic valve allografts reduces leaflet destruction and extracellular matrix remodeling.* J Thorac Cardiovasc Surg, 2003. 126 (6): p. 2003-10.
70. Kasimir, M. T., et al., *Comparison of different decellularization procedures of porcine heart valves.* Int J Artif Organs, 2003. 26(5): p. 421-7.
71. Hilbert, S. L., et al., *Explant pathology study of decellularized carotid artery vascular grafts.* J Biomed Mater Res A, 2004. 69(2): p. 197-204.
72. Teebken, O. E., et al., *Tissue engineering of vascular grafts: human cell seeding of decellularised porcine matrix.* Eur J Vasc Endovasc Surg, 2000. 19(4): p. 381-6.
73. Schaner, P. J., et al., *Decellularized vein as a potential scaffold for vascular tissue engineering.* J Vasc Surg, 2004. 40(1): p. 146-53.
74. Huynh, T., et al., *Remodeling of an acellular collagen graft into a physiologically responsive neovessel.* Nat Biotechnol, 1999. 17(11): p. 1083-6.
75. Lu, Q., et al., *Novel porous aortic elastin and collagen scaffolds for tissue engineering.* Biomaterials, 2004. 25(22): p. 5227-37.
76. Uchimura, E., et al., *Novel method of preparing acellular cardiovascular grafts by decellularization with poly(ethylene glycol).* J Biomed Mater Res A, 2003. 67(3): p. 834-7.
77. Courtman, D. W., B. F. Errett, and G. J. Wilson, *The role of crosslinking in modification of the immune response elicited against xenogenic vascular acellular matrices.* J Biomed Mater Res, 2001. 55(4): p. 576-86.
78. Courtman, D. W., et al., *Development of a pericardial acellular matrix biomaterial: biochemical and mechanical effects of cell extraction.* J Biomed Mater Res, 1994. 28(6): p. 655-66.
79. Sievers, H. H., et al., *Decellularized pulmonary homograft (SynerGraft) for reconstruction of the right ventricular outflow tract: first clinical experience.* Z Kardiol, 2003. 92(1): p. 53-9.
80. Samouillan, V., et al., *Thermal analysis characterization of aortic tissues for cardiac valve bioprostheses.* J Biomed Mater Res, 1999. 46(4): p. 531-8.
81. Rieder, E., et al., *Decellularization protocols of porcine heart valves differ importantly in efficiency of cell removal and susceptibility of the matrix to recellularization with human vascular cells.* J Thorac Cardiovasc Surg, 2004. 127(2): p. 399-405.
82. Surfactants, D., *Triton X-100 Surfactant: Product Information.* p. 2.
83. Cho, S. W., et al., *Vascular patches tissue-engineered with autologous bone marrow-derived cells and decellularized tissue matrices.* Biomaterials, 2005. 26(14): p. 1915-24.
84. Horowitz, B. and E. Ben-Hur, *Strategies for viral inactivation.* Curr Opin Hematol, 1995. 2(6): p. 484-92.
85. Huang, Q., et al., *Use of peracetic acid to sterilize human donor skin for production of acellular dermal matrices for clinical use.* Wound Repair Regen, 2004. 12(3): p. 276-87.

86. Pruss, A., et al., *Validation of the sterilization procedure of allogeneic avital bone transplants using peracetic acid-ethanol*. Biologicals, 2001. 29(2): p. 59-66.
87. Fideler, B. M., et al., *Effects of gamma irradiation on the human immunodeficiency virus. A study in frozen human bone-patellar ligament-bone grafts obtained from infected cadavera*. J Bone Joint Surg Am, 1994. 76(7): p. 1032-5.
88. Pruss, A., et al., *Effect of gamma irradiation on human cortical bone transplants contaminated with enveloped and non-enveloped viruses*. Biologicals, 2002. 30(2): p. 125-33.
89. Fideler, B. M., et al., *Gamma irradiation: effects on biomechanical properties of human bone-patellar tendon-bone allografts*. Am J Sports Med, 1995. 23(5): p. 643-6.
90. Center, G. P., *Introduction to viruses*, VNAA (Visiting Nurse Associations of America).
91. Dox, I. G., Melloni, B. J., Eisner, G. M., *The HarperCollins Illustrated Medical Dictionary*. 1993, New York: HarperCollins Publisher, Inc.
92. Mitra, G., et al., *Inactivation of viruses in therapeutic products derived from human plasma*. Am J Med, 1988. 84(6A): p. 87-90.
93. Horowitz, B., et al., *Solvent/detergent-treated plasma: a virus-inactivated substitute for fresh frozen plasma*. Blood, 1992. 79(3): p. 826-31.
94. Block, S. S., *Disinfection, Sterilization, and Preservation*. Fifth ed. 2001, Philadelphia: Lippincott Williams & Wilkins.
95. van Bueren, J., D. P. Larkin, and R. A. Simpson, *Inactivation of human immunodeficiency virus type 1 by alcohols*. J Hosp Infect, 1994. 28(2): p. 137-48.
96. Acosta-Gio, A. E., J. L. Rueda-Patino, and L. Sanchez-Perez, *Sporicidal activity in liquid chemical products to sterilize or high-level disinfect medical and dental instruments*. Am J Infect Control, 2005. 33(5): p. 307-9.
97. Hodde, J. and M. Hiles, *Virus safety of a porcine-derived medical device: evaluation of a viral inactivation method*. Biotechnol Bioeng, 2002. 79(2): p. 211-6.
98. Koivunen, J. and H. Heinonen-Tanski, *Inactivation of enteric microorganisms with chemical disinfectants, UV irradiation and combined chemical/UV treatments*. Water Res, 2005. 39(8): p. 1519-26.
99. Pruss, A., et al., *Peracetic acid-ethanol treatment of allogeneic avital bone tissue transplants—a reliable sterilization method*. Ann Transplant, 2003. 8(2): p. 34-42.
100. Hodde, J. P., et al., *Retention of endothelial cell adherence to porcine-derived extracellular matrix after disinfection and sterilization*. Tissue Eng, 2002. 8(2): p. 225-34.
101. Reinhart, D., *Control of odors from construction and demolition (C&D) debris landfills*. 2004, University of Florida: Gainesville.
102. Scheffler, S. U., et al., *Biomechanical comparison of human bone-patellar tendon-bone grafts after sterilization with peracetic acid ethanol*. Cell Tissue Bank, 2005. 6(2): p. 109-15.
103. *Guidance on the Content and Format of Premarket Notification [510(k)] Submissions for Liquid Chemical Germicides*, U.S.D.o.H.a.H. Services, Editor. 1996.
104. Mazzola, P. G., T. C. Penna, and A. M. Martins, *Determination of decimal reduction time (D value) of chemical agents used in hospitals for disinfection purposes*. BMC Infect Dis, 2003. 3(1): p. 24.
105. Kenyon, D. E., *A mathematical model of water flux through aortic tissue*. Bull Math Biol, 1979. 41(1): p. 79-90.
106. Meyer, G., R. Merval, and A. Tedgui, *Effects of pressure-induced stretch and convection on low-density lipoprotein and albumin uptake in the rabbit aortic wall*. Circ Res, 1996. 79(3): p. 532-40.
107. Prosi, M., et al., *Mathematical and numerical models for transfer of low-density lipoproteins through the arterial walls: a new methodology for the model set up with applications to the study of disturbed lumenal flow*. J Biomech, 2005. 38(4): p. 903-17.
108. Tada, S. and J. M. Tarbell, *Fenestral pore size in the internal elastic lamina affects transmural flow distribution in the artery wall*. Ann Biomed Eng, 2001. 29(6): p. 456-66.
109. Ander, S., et al., *Pressure-induced vector transport in human saphenous vein*. Ann Biomed Eng, 2005. 33(2): p. 202-8.
110. Wang, D. M. and J. M. Tarbell, *Modeling interstitial flow in an artery wall allows estimation of wall shear stress on smooth muscle cells*. J Biomech Eng, 1995. 117(3): p. 358-63.
111. Henzler, T. and E. Steudle, *Transport and metabolic degradation of hydrogen peroxide in Chara corallina: model calculations and measurements with the pressure probe suggest transport of H(2)O(2) across water channels*. J Exp Bot, 2000. 51(353): p. 2053-66.
112. Bradford, M. M., *A Rapid and Sensitive Method for the Quantitation of Microgram Quantities of Protein Utilizing the Principle of Protein-Dye Binding*. Anal. Biochem., 1976. 72:248-254.

What is claimed is:

1. A process for making a vascular graft more suitable for implantation into a recipient, the process comprising:
(a) contacting a vascular graft with an oxidizing sterilant; and
(b) contacting the vascular graft with a cleaning solution;
wherein during either step (a) or (b) or both,
a pressure gradient in the range of from about 100 mm Hg to about 400 mm Hg across a wall of said vascular graft is maintained by the flow of said cleaning solution or said oxidizing sterilant through said vascular graft;
wherein the contacting steps are at a temperature less than about 45° C. and for a total contact time less than about 8 hours; and
wherein the vascular graft comprises allograft or xenograft vascular tissue.

2. The process of claim 1, wherein the steps are performed in the order (a), then (b).

3. The process of claim 1, wherein a decellularized graft is produced.

4. The process of claim 1, wherein the oxidizing sterilant is selected from the group consisting of peroxides, oxides, hypochlorites, ozone and percarboxylic acids; or mixtures thereof.

5. The process of claim 1, wherein the oxidizing sterilant is a percarboxylic acid selected from the group consisting of peracetic acid, perpropionic acid, perbutyric acid, peroctanoic acid, perglycolic acid, perglutaric acid, persuccinic acid, perlactic acid, percitric acid and perdecanoic acid; or mixtures thereof.

6. The process of claim 1, wherein the oxidizing sterilant is peracetic acid.

7. The process of claim 1, wherein the cleaning solution is selected from the group consisting of solutions of cholate, alcohol ethoxylates, alkylphenol ethoxylates, alkyl polyglycosides, polyoxyethylene ethers, polyoxyethylene sorbitans, any of the Triton, Tween or Brij series of detergents, alkyl benzenesulfonates, alkyl sulfonates, alkyl phosphates, and alkyl sulfates; or salts or mixtures thereof.

8. The process of claim 1, wherein the cleaning solution is a solution of cholate.

9. The process of claim 1, wherein during either step (a) or (b) or both, the vascular graft is submerged in solution.

10. The process of claim 1, wherein said pressure gradient results in mass transport by fluid convection and/or diffusion through said wall of said vascular graft.

* * * * *

UNITED STATES PATENT AND TRADEMARK OFFICE
CERTIFICATE OF CORRECTION

| | | |
|---|---|---|
| PATENT NO. | : 7,658,706 B2 | Page 1 of 1 |
| APPLICATION NO. | : 11/634436 | |
| DATED | : February 9, 2010 | |
| INVENTOR(S) | : Donna Squillace | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 301 days.

Signed and Sealed this

Thirtieth Day of November, 2010

David J. Kappos
*Director of the United States Patent and Trademark Office*